(12) United States Patent
Bonnette et al.

(10) Patent No.: US 10,806,559 B2
(45) Date of Patent: Oct. 20, 2020

(54) INTRAVASCULAR GUIDEWIRE FILTER SYSTEM FOR PULMONARY EMBOLISM PROTECTION AND EMBOLISM REMOVAL OR MACERATION

(71) Applicant: SurModics MD, LLC, Eden Prairie, MN (US)

(72) Inventors: Michael Bonnette, Minneapolis, MN (US); Richard Prather, St. Michael, MN (US); Eric J Thor, Arden Hills, MN (US); Stephen E Weisel, Brook Park, MN (US); Douglas L Ball, Coon Rapids, MN (US); David B Morris, Anoka, MN (US); Debra M Kozak, Forest Lake, MN (US); Gary Ansel, Columbus, OH (US)

(73) Assignee: Surmodics MD, LLC, Eden Prairie, MN (US)

( * ) Notice: Subject to any disclaimer, the term of this patent is extended or adjusted under 35 U.S.C. 154(b) by 234 days.

(21) Appl. No.: 15/093,916

(22) Filed: Apr. 8, 2016

(65) Prior Publication Data

US 2016/0220346 A1 Aug. 4, 2016

Related U.S. Application Data

(63) Continuation of application No. 12/738,702, filed as application No. PCT/US2008/081310 on Oct. 27, 2008, now Pat. No. 9,827,084.
(Continued)

(51) Int. Cl.
*A61F 2/01* (2006.01)
*A61B 17/221* (2006.01)
(Continued)

(52) U.S. Cl.
CPC ............ *A61F 2/013* (2013.01); *A61B 17/221* (2013.01); *A61B 17/22012* (2013.01);
(Continued)

(58) Field of Classification Search
CPC ...... A61F 2/01; A61F 2/013; A61F 2002/011; A61F 2002/016; A61F 2002/018;
(Continued)

(56) References Cited

U.S. PATENT DOCUMENTS

| 4,425,908 A | 1/1984 | Simon |
| 4,611,594 A | 9/1986 | Grayhack et al. |

(Continued)

FOREIGN PATENT DOCUMENTS

| DE | 2211972 A1 | 9/1972 |
| EP | 0655228 A1 | 5/1995 |

(Continued)

OTHER PUBLICATIONS

"U.S. Appl. No. 12/738,702, Examiner Interview Summary dated Mar. 6, 2015", 3 pgs.
(Continued)

*Primary Examiner* — Tan-Uyen T Ho
*Assistant Examiner* — Chima U Igboko
(74) *Attorney, Agent, or Firm* — Schwegman Lundberg & Woessner, P.A.

(57) ABSTRACT

An intravascular emboli capture and retrieval system for intravascular embolism protection and embolism removal or maceration. Guidewire mounted proximally and distally located multiple opening filters are deployed within the vasculature and used to part, divide and macerate embolic debris and to capture such embolic debris within the confines thereof. A deployable flexible preformed memory shaped capture sleeve is alternatively used to collapse one or
(Continued)

more filters and embolic debris therein for subsequent proximal withdrawal from the vasculature.

18 Claims, 48 Drawing Sheets

Related U.S. Application Data

(60) Provisional application No. 61/000,465, filed on Oct. 26, 2007.

(51) Int. Cl.
*A61B 17/22* (2006.01)
*A61B 17/00* (2006.01)

(52) U.S. Cl.
CPC .......... *A61B 17/22032* (2013.01); *A61B 2017/00778* (2013.01); *A61B 2017/00867* (2013.01); *A61B 2017/22001* (2013.01); *A61B 2017/2212* (2013.01); *A61B 2017/22035* (2013.01); *A61B 2017/22038* (2013.01); *A61B 2017/22042* (2013.01); *A61B 2017/22054* (2013.01); *A61F 2/011* (2020.05); *A61F 2002/016* (2013.01); *A61F 2210/0014* (2013.01); *A61F 2210/0057* (2013.01); *A61F 2210/0061* (2013.01); *A61F 2230/008* (2013.01); *A61F 2230/0008* (2013.01); *A61F 2230/0069* (2013.01); *A61F 2230/0086* (2013.01); *A61F 2230/0093* (2013.01); *A61F 2230/0097* (2013.01); *A61F 2250/004* (2013.01); *A61F 2250/0036* (2013.01); *A61F 2250/0042* (2013.01)

(58) Field of Classification Search
CPC .......... A61B 17/221; A61B 2017/2212; A61B 2017/2215; A61B 2017/2217; A61M 2025/09125
See application file for complete search history.

(56) References Cited

U.S. PATENT DOCUMENTS

| | | | |
|---|---|---|---|
| 4,643,184 A | 2/1987 | Mobin-Uddin | |
| 4,690,672 A | 9/1987 | Veltrup | |
| 5,011,488 A | 4/1991 | Ginsburg | |
| 5,074,871 A | 12/1991 | Groshong | |
| 5,102,415 A | 4/1992 | Guenther et al. | |
| 5,370,609 A | 12/1994 | Drasler et al. | |
| 5,419,774 A | 5/1995 | Willard et al. | |
| 5,688,234 A | 11/1997 | Frisbie | |
| 5,785,675 A | 7/1998 | Drasler et al. | |
| 5,814,064 A | 9/1998 | Daniel et al. | |
| 5,908,435 A | 6/1999 | Samuels | |
| 5,941,871 A | 8/1999 | Adams et al. | |
| 5,968,057 A | 10/1999 | Taheri | |
| 5,971,938 A | 10/1999 | Hart et al. | |
| 5,989,271 A | 11/1999 | Bonnette et al. | |
| 6,001,118 A | 12/1999 | Daniel et al. | |
| 6,059,814 A | 5/2000 | Ladd | |
| 6,066,149 A | 5/2000 | Samson et al. | |
| 6,080,170 A | 6/2000 | Nash et al. | |
| 6,096,001 A | 8/2000 | Drasler et al. | |
| 6,135,977 A | 10/2000 | Drasler et al. | |
| 6,171,327 B1 * | 1/2001 | Daniel ................. | A61F 2/01 606/159 |
| 6,176,844 B1 | 1/2001 | Lee | |
| 6,203,561 B1 | 3/2001 | Ramee et al. | |
| 6,206,868 B1 | 3/2001 | Parodi | |
| 6,221,006 B1 | 4/2001 | Dubrul et al. | |
| 6,238,412 B1 | 5/2001 | Dubrul et al. | |
| 6,245,089 B1 | 6/2001 | Daniel et al. | |
| 6,258,061 B1 | 7/2001 | Drasler et al. | |
| 6,258,115 B1 | 7/2001 | Dubrul | |
| 6,277,139 B1 | 8/2001 | Levinson et al. | |
| 6,290,710 B1 | 9/2001 | Cryer et al. | |
| 6,325,815 B1 | 12/2001 | Kusleika et al. | |
| 6,325,816 B1 | 12/2001 | Fulton, III et al. | |
| 6,338,735 B1 | 1/2002 | Stevens | |
| 6,346,116 B1 | 2/2002 | Brooks et al. | |
| 6,361,546 B1 | 3/2002 | Khosravi | |
| 6,371,969 B1 | 4/2002 | Tsugita et al. | |
| 6,436,120 B1 | 8/2002 | Meglin | |
| 6,443,972 B1 | 9/2002 | Bosma et al. | |
| 6,447,531 B1 | 9/2002 | Amplatz | |
| 6,450,989 B2 | 9/2002 | Dubrul et al. | |
| 6,458,139 B1 * | 10/2002 | Palmer ................. | A61B 17/221 606/113 |
| 6,485,500 B1 | 11/2002 | Kokish et al. | |
| 6,485,502 B2 | 11/2002 | Don Michael et al. | |
| 6,491,660 B2 | 12/2002 | Guo et al. | |
| 6,511,492 B1 | 1/2003 | Rosenbluth et al. | |
| 6,517,551 B1 | 2/2003 | Driskill | |
| 6,524,323 B1 | 2/2003 | Nash et al. | |
| 6,527,746 B1 | 3/2003 | Oslund et al. | |
| 6,544,209 B1 | 4/2003 | Drasler et al. | |
| 6,575,996 B1 | 6/2003 | Denison et al. | |
| 6,605,102 B1 | 8/2003 | Mazzocchi et al. | |
| 6,635,070 B2 | 10/2003 | Leeflang et al. | |
| 6,652,548 B2 | 11/2003 | Evans et al. | |
| 6,676,637 B1 | 1/2004 | Bonnette et al. | |
| 6,679,893 B1 | 1/2004 | Tran | |
| 6,682,546 B2 | 1/2004 | Amplatz | |
| 6,695,813 B1 | 2/2004 | Boyle et al. | |
| 6,695,858 B1 | 2/2004 | Dubrul et al. | |
| 6,712,835 B2 | 3/2004 | Mazzocchi et al. | |
| 6,726,701 B2 | 4/2004 | Gilson et al. | |
| 6,740,061 B1 | 5/2004 | Oslund et al. | |
| 6,758,855 B2 | 7/2004 | Fulton, III et al. | |
| 6,761,727 B1 | 7/2004 | Ladd | |
| 6,773,448 B2 | 8/2004 | Kusleika et al. | |
| 6,805,864 B1 | 10/2004 | Vinson et al. | |
| 6,814,740 B2 | 11/2004 | Mcalister | |
| 6,887,256 B2 | 5/2005 | Gilson et al. | |
| 6,989,019 B2 | 1/2006 | Mazzocchi et al. | |
| 7,011,654 B2 | 3/2006 | Dubrul et al. | |
| 7,163,550 B2 | 1/2007 | Boismier | |
| 7,169,154 B1 | 1/2007 | Que et al. | |
| 7,220,269 B1 | 5/2007 | Ansel et al. | |
| 7,241,304 B2 | 7/2007 | Boyle et al. | |
| 7,241,305 B2 | 7/2007 | Ladd | |
| 7,252,675 B2 | 8/2007 | Denison et al. | |
| 7,344,549 B2 | 3/2008 | Boyle et al. | |
| 7,491,210 B2 | 2/2009 | Dubrul et al. | |
| 7,537,601 B2 | 5/2009 | Cano et al. | |
| 7,717,936 B2 | 5/2010 | Keating et al. | |
| 7,766,936 B2 | 8/2010 | Ladd | |
| 7,780,694 B2 | 8/2010 | Palmer et al. | |
| 7,785,345 B2 | 8/2010 | Ladd | |
| 9,149,609 B2 | 10/2015 | Ansel et al. | |
| 9,827,084 B2 | 11/2017 | Bonnette et al. | |
| 9,943,397 B2 | 4/2018 | Bonnette et al. | |
| 2001/0012951 A1 | 8/2001 | Bates et al. | |
| 2002/0026203 A1 | 2/2002 | Bates et al. | |
| 2002/0026211 A1 * | 2/2002 | Khosravi ................. | A61F 2/01 606/200 |
| 2002/0068954 A1 | 6/2002 | Foster | |
| 2002/0123765 A1 * | 9/2002 | Sepetka ............ | A61B 17/22031 606/192 |
| 2003/0065355 A1 | 4/2003 | Weber | |
| 2003/0114879 A1 | 6/2003 | Euteneuer et al. | |
| 2003/0187475 A1 | 10/2003 | Tsugita et al. | |
| 2003/0229374 A1 | 12/2003 | Brady et al. | |
| 2004/0133232 A1 | 7/2004 | Rosenbluth et al. | |
| 2004/0153117 A1 * | 8/2004 | Clubb ................. | A61F 2/01 606/200 |
| 2004/0215230 A1 | 10/2004 | Frazier et al. | |
| 2005/0119668 A1 | 6/2005 | Teague et al. | |
| 2005/0159772 A1 | 7/2005 | Lowe et al. | |
| 2005/0192620 A1 | 9/2005 | Cully et al. | |
| 2006/0030877 A1 | 2/2006 | Martinez et al. | |

(56) References Cited

U.S. PATENT DOCUMENTS

| | | | |
|---|---|---|---|
| 2006/0135987 | A1 | 6/2006 | Jones et al. |
| 2006/0241676 | A1 | 10/2006 | Johnson et al. |
| 2006/0253145 | A1 | 11/2006 | Lucas |
| 2007/0060942 | A2 | 3/2007 | Zadno-Azizi |
| 2007/0088383 | A1 | 4/2007 | Pal et al. |
| 2007/0167974 | A1 | 7/2007 | Cully et al. |
| 2007/0191878 | A1 | 8/2007 | Segner et al. |
| 2007/0198051 | A1 | 8/2007 | Clubb et al. |
| 2007/0208351 | A1 | 9/2007 | Turner et al. |
| 2008/0234722 | A1 | 9/2008 | Bonnette et al. |
| 2008/0312681 | A1 | 12/2008 | Ansel et al. |
| 2009/0069828 | A1 | 3/2009 | Martin et al. |
| 2010/0268264 | A1 | 10/2010 | Bonnette et al. |
| 2017/0325931 | A1 | 11/2017 | Bonnette et al. |
| 2020/0155293 | A1 | 5/2020 | Morrison et al. |

FOREIGN PATENT DOCUMENTS

| | | |
|---|---|---|
| EP | 1545388 B1 | 8/2009 |
| EP | 2211972 A1 | 8/2010 |
| EP | 2211972 B1 | 12/2015 |
| FR | 2580504 A1 | 10/1986 |
| FR | 2694687 A1 | 2/1994 |
| GB | 2211972 A | 7/1989 |
| GB | 2211972 B | 10/1991 |
| JP | 8187294 | 7/1996 |
| WO | WO-9922673 A1 | 5/1999 |
| WO | WO-0115629 A1 | 3/2001 |
| WO | WO-0117602 A1 | 3/2001 |
| WO | WO-0145590 A2 | 6/2001 |
| WO | WO-0167989 A2 | 9/2001 |
| WO | WO-2008036156 A1 | 3/2008 |
| WO | WO-2008157202 A1 | 12/2008 |
| WO | WO-2009055782 A1 | 4/2009 |

OTHER PUBLICATIONS

"U.S. Appl. No. 12/738,702, Examiner Interview Summary dated Mar. 9, 2016", 3 pgs.
"U.S. Appl. No. 12/738,702, Examiner Interview Summary dated Aug. 9, 2017", 3 pgs.
"U.S. Appl. No. 12/738,702, Final Office Action dated May 17, 2017", 17 pgs.
"U.S. Appl. No. 12/738,702, Final Office Action dated Aug. 15, 2013", 12 pgs.
"U.S. Appl. No. 12/738,702, Final Office Action dated Dec. 19, 2014", 14 pgs.
"U.S. Appl. No. 12/738,702, Non Final Office Action dated Apr. 23, 2015", (9 pgs).
"U.S. Appl. No. 12/738,702, Non Final Office Action dated Jul. 7, 2016", 8 pgs.
"U.S. Appl. No. 12/738,702, Non Final Office Action dated Oct. 3, 2014", 11 pgs.
"U.S. Appl. No. 12/738,702, Non Final Office Action dated Nov. 6, 2012", 11 pgs.
"U.S. Appl. No. 12/738,702, Non Final Office Action dated Dec. 1, 2015", 9 pgs.
"U.S. Appl. No. 12/738,702, Notice of Allowance dated Oct. 18, 2017", 12 pgs.
"U.S. Appl. No. 12/738,702, Response filed Mar. 9, 2016 to Non Final Office Action dated Dec. 1, 2015", 17 pgs.
"U.S. Appl. No. 12/738,702, Response filed Mar. 13, 2015 to Final Office Action dated Dec. 19, 2014", 11 pgs.
"U.S. Appl. No. 12/738,702, Response filed May 6, 2013 to Non Final Office Action dated Nov. 6, 2012", 9 pgs.
"U.S. Appl. No. 12/738,702, Response filed Jun. 1, 2015 to Non Final Office Action dated Apr. 23, 2015", 5 pgs.
"U.S. Appl. No. 12/738,702, Response filed Aug. 2, 2017 to Final Office Action dated May 17, 2017", 12 pgs.
"U.S. Appl. No. 12/738,702, Response filed Aug. 24, 16 to Non Final Office Action dated Jul. 7, 2016", (14 pgs).
"U.S. Appl. No. 12/738,702, Response filed Sep. 28, 2012 to Restriction Requirement dated Jun. 28, 2012", 9 pgs.
"U.S. Appl. No. 12/738,702, Response filed Nov. 11, 2014 to Non Final Office Action dated Oct. 3, 2014", 10 pgs.
"U.S. Appl. No. 12/738,702, Response filed Nov. 14, 2013 to Final Office Action dated Aug. 15, 2013", 7 pgs.
"U.S. Appl. No. 12/738,702, Restriction Requirement dated Jun. 28, 2012", 8 pgs.
"U.S. Appl. No. 15/667,984, Non Final Office Action dated Oct. 19, 2017", 11 pgs.
"U.S. Appl. No. 15/667,984, Notice of Allowance dated Dec. 6, 2017", 11 pgs.
"U.S. Appl. No. 15/667,984, Response filed Oct. 23, 2017 to Non Final Office Action dated Oct. 19, 2017", 7 pgs.
"European Application Serial No. 08840818.2, Communication Pursuant to Article 94(3) EPC dated Nov. 11, 2011", 4 pgs.
"European Application Serial No. 08840818.2, Extended European Search Report dated Mar. 4, 2011", 6 pgs.
"European Application Serial No. 08840818.2, Intention to Grant dated Mar. 26, 2015", 101 pgs.
"European Application Serial No. 08840818.2, Response filed May 18, 2012 to Communication Pursuant to Article 94(3) EPC dated Nov. 22, 2011", 11 pgs.
"European Application Serial No. 08840818.2, Response filed Jul. 6, 2010 to Communication pursuant to Rules 161(2) and 162 EPC dated Jun. 4, 2010", 3 pgs.
"European Application Serial No. 08840818.2, Response filed Sep. 29, 2011 to Extended European Search Report dated Mar. 4, 2011", 17 pgs.
"International Application Serial No. PCT/US2004/036451, International Search Report dated Aug. 26, 2005", 1 pg.
"International Application Serial No. PCT/US2008/081310, International Preliminary Report on Patentability dated Apr. 27, 2010", 10 pgs.
"International Application Serial No. PCT/US2008/081310, International Search Report dated Jan. 6, 2009", 1 pg.
"International Application Serial No. PCT/US2008/081310, Written Opinion dated Jan. 6, 2009", 9 pgs.
"International Application Serial PCT/US2008/066644, International Preliminary Report on Patentability dated Dec. 17, 2009", 6 pgs.
"International Application Serial PCT/US2008/066644, International Search Report dated Dec. 12, 2009", 1 pg.
Henkes, H., et al., "A New Device for Endovascular Coil Retrieval from Intracranial Vessels: Alligator Retrieval Device", American Journal of Neuroradiology, vol. 27, Issue 2, (Feb. 2006), 327-329.
U.S. Appl. No. 12/738,702 U.S. Pat. No. 9,827,084, filed Apr. 19, 2010, Intravascular Guidewire Filter System for Pulmonary Embolism Protection and Embolism Removal or Maceration.
U.S. Appl. No. 15/667,984 U.S. Pat. No. 9,943,397, filed Aug. 3, 2017, Intravascular Guidewire Filter System for Pulmonary Embolism Protection and Embolism Removal or Maceration.
U.S. Appl. No. 12/152,367 U.S. Pat. No. 9,149,609, filed May 14, 2008, Catheter for removal of an organized embolic thrombus.
U.S. Appl. No. 16/742,662, filed Jan. 14, 2020, Intra Vascular Guidewire Filter System for Pulmonary Embolism Protection and Embolism Removal or Maceration.
"Alligator Retrieval Device (ARD), Instructions for Use", Chestnut Medical Technologies, Inc., (Accessed 2010), 1 pg.
"U.S. Appl. No. 12/152,367, Examiner Interview Summary dated Nov. 15, 2012", 3 pgs.
"U.S. Appl. No. 12/152,367, Final Office Action dated Aug. 28, 2014", 10 pgs.
"U.S. Appl. No. 12/152,367, Final Office Action dated Dec. 6, 2011", 11 pgs
"U.S. Appl. No. 12/152,367, Final Office Action dated Dec. 6, 2012", 10 pgs.
"U.S. Appl. No. 12/152,367, Non Final Office Action dated Mar. 13, 2015", 10 pgs.
"U.S. Appl. No. 12/152,367, Non Final Office Action dated Apr. 1, 2011", 12 pgs.
"U.S. Appl. No. 12/152,367, Non Final Office Action dated Jun. 18, 2012", 10 pgs.

(56) References Cited

OTHER PUBLICATIONS

"U.S. Appl. No. 12/152,367, Notice of Allowance dated Jun. 17, 2015", 7 pgs.
"U.S. Appl. No. 12/152,367, Response filed Apr. 24, 2015 to Non Final Office Action dated Mar. 13, 2015", 16 pgs.
"U.S. Appl. No. 12/152,367, Response filed May 6, 2013 to Final Office Action dated Dec. 6, 2012", 11 pgs.
"U.S. Appl. No. 12/152,367, Response filed May 7, 2012 to Final Office Action dated Dec. 6, 2011", 7 pgs.
"U.S. Appl. No. 12/152,367, Response filed Sep. 26, 2011 to Non Final Office Action dated Apr. 1, 2011", 11 pgs.
"U.S. Appl. No. 12/152,367, Response filed Nov. 19, 2012 to Non Final Office Action dated Jun. 18, 2012", 12 pgs.
"U.S. Appl. No. 12/152,367, Response filed Nov. 19, 2014 Final Office Action dated Aug. 28, 2014", 10 pgs.
"International Application Serial PCT/US2008/066644, Written Opinion dated Oct. 9, 2008", 5 pgs.

* cited by examiner

INTRAVASCULAR GUIDEWIRE FILTER SYSTEM FOR PULMONARY EMBOLISM PROTECTION AND EMBOLISM REMOVAL OR MACERATION

CROSS REFERENCE TO RELATED APPLICATIONS

This application is a continuation of U.S. patent application Ser. No. 12/738,702, filed on Apr. 19, 2010, which is a 371 national phase application of PCT International Application No. PCT/US08/81310, filed on Oct. 27, 2008, and designating the United States of America, which claims the benefit from the earlier filed U.S. Provisional Application No. 61/000,465 filed Oct. 26, 2007, entitled "Intravascular Macerating Filter," and is hereby incorporated into this application by reference as if fully set forth herein.

This patent application is related to patent application Ser. No. 12/152,367 filed on May 14, 2008, entitled "Catheter for Removal of an Organized Embolic Thrombus."

BACKGROUND

The present disclosure relates to a guidewire system and, more particularly, is for an intravascular guidewire filter system for pulmonary embolism protection and embolism removal or maceration.

DESCRIPTION OF THE PRIOR ART

Prior art devices have been used for embolization protection during treatment involving an intravascular intervention where it is not uncommon for large pieces of embolic debris to become dislodged during the debulking of vessels. In the case of deep vein thrombosis (DVT), the interventional treatment of deep vein thrombosis is accomplished by various methods. Historically, deep vein thrombosis has been treated with heparin since it was shown to reduce the occurrence of pulmonary embolism (PE). However, this modality of treatment often leaves the patient with long term debilitations since the underlying deep vein thrombosis is not treated, such debilitations including open sores, swelling, and continuous leg pain. Some physicians aggressively treat deep vein thrombosis by using either thrombectomy devices or fibrinolytics. In either case, such deep vein thrombosis treatment can result in pieces of thrombus debris being dislodged and which pieces can move to the lungs. If the thrombus debris is large enough to effectively inhibit a pulmonary function, it is classified as a pulmonary embolism. Institutions and physician practice for preventing pulmonary embolisms while performing deep vein thrombosis interventions vary. The current option for preventing a pulmonary embolism while performing a deep vein thrombosis intervention is to place a filter in the inferior vena cava (IVC). However, IVC filters come with their own set of shortcomings. IVC filters have been associated with thrombosis (they clot up on their own), filter migration, perforation of the IVC, and the like. IVC filters have been associated with increased mortality. Currently, some IVC filters are available as a removable type filter. Typically, a patient would come in a short time after the intervention for removal of the filter. However, if the patient neglects to make the follow-up visit in time, the filter can become difficult or impossible to remove. Furthermore, there is the expense of these filters. Given this choice of an IVC filter versus the risk of pulmonary embolism with no filter, some physicians view the treatment of deep vein thrombosis as problematic.

The purpose of the devices set forth in the present disclosure is to remove some of the obstacles for providing embolic protection during the treatment of deep vein thrombosis. The devices of the present disclosure do not have the hooks that penetrate the wall of the IVC. For a permanent or removable IVC filter, these hooks are needed to prevent filter migration. However, with a filter on a guidewire as used in the devices of the present disclosure, the risk of migration is mitigated by the fact that the physician can monitor the filter location throughout the intravascular procedure. The lack of hooks reduces the risk of injury or perforation of the IVC. Furthermore, the filter of the present disclosure is on a guidewire that must be removed at the end of the intravascular procedure. Therefore, there is considerably less risk that the filter of the present disclosure would become thrombosed since it is in the body while the patient is under a large amount of anti-thrombotics. Finally, the ease of installation and removal of the filter of the present disclosure is viewed as superior to implantable IVC filters. Extreme caution must be used when implanting a permanent or removable IVC filter since many of the IVC filters are not effective unless placed precisely. The removal of an IVC filter involves snaring the IVC filter and pulling it away from the wall of the IVC. Both are difficult. In the case of the devices set forth in the present disclosure, the filters of the device are merely unsheathed, the position of which can be proximal to the IVC if that is desired. The placement of the filter of the present disclosure is not as critical since it is only used throughout the intervention. The removal of the filter of the present disclosure is simpler since there is no snaring needed and the device has no hooks or ingrowth to the vessel.

One purpose of the devices set forth in the present disclosure is to provide easily deployed pulmonary embolism protection during a deep vein thrombosis intervention while simultaneously avoiding the need for long debulking times in the IVC with an AngioJet® thrombectomy device and catheter, thereby resulting in a lower hemolysis. The devices set forth in the present disclosure accomplish the same level of filter protection as a removable IVC filter during the procedure. The devices of the present disclosure overcome some of the associated risks with using IVC filters since it does not have the same migration prevention design features and does not have the complexity associated with snaring a filter device for retrieval. The filter device of the present disclosure is simpler to manufacture and easier to deploy than other marketed IVC filters. Furthermore the macerating aspect of the filter device of the present disclosure minimizes the run time of an AngioJet® thrombectomy device and catheter in the IVC. This minimization of the run time should be associated with less hemolysis. Thus, the designs set forth in the present disclosure provide a safer means for providing distal protection during a deep vein thrombosis intervention.

Another purpose of the devices of the present disclosure is to provide a nonocclusive retrieval device for pulling embolic debris proximally and removing it from the vasculature. With respect to a difficult and tough embolic debris removal, there are few or no effective interventional embolectomy tools. Sometimes, a Forgarty balloon is used via a surgical cutdown for debris removal. Some physicians try to use snares to pull tough embolic debris back into large guide catheters or even the interventional sheath. Nevertheless, bench testing reveals that large debris will be stripped off of snares as they are pulled into guides or interventional sheaths. In order to provide a successful embolectomy, the devices of the present disclosure provide for the use of a cooperatively flexible nitinol mesh as part of a capture sleeve and a means for pulling the debris into the nitinol mesh capture sleeve. In the case of some prior art embolectomy devices, the debris was brought into a nitinol mesh capture sleeve with an occlusion balloon on a wire. However, testing reveals that if the vessel diameter changes dramatically distal to the embolic debris to the mesh location, the thrombus debris may slide past the occlusion balloon since the occlusion balloon will not change in size dramatically. Furthermore, in a highly bifurcated anatomy, an occlusive balloon will encourage the embolic debris to float down alternative branches as the occlusion balloon is pulled proximally. A nitinol filter on a guidewire shown in the present disclosure is not occlusive and it changes size more dramatically than an occlusion balloon, thereby being more effective. The nitinol filters are shaped and designed for stiffness during pulling, but may be collapsed by compression interaction with a capture/delivery sheath and/or nitinol mesh capture sleeve, whereby the debris can be formed into smaller pieces (macerated) by the inwardly forced structure of the filter. The smaller pieces can then be more readily sized and compressed by the capture/delivery sheath and/or nitinol mesh capture sleeve for proximal removal through the capture/delivery sheath.

In general, the devices of the present disclosure are used to capture or trap embolic debris, either passively or actively, without the need for stopping blood flow. The trapped or pulled embolic debris is then either compressed in a simple tube sheath and/or expandable mesh sleeve and removed or can be minimized/macerated to a manageable size and treated by an AngioJet® thrombectomy device and catheter or lytics or can be of a clinically insignificant size so as to be resorbed by the body. The guidewire of the present disclosure is utilized for passage of devices over it, such as an AngioJet® thrombectomy catheter or other useful devices, in order to debulk or remove debris or to provide for the use of a stent or other devices.

SUMMARY OF THE DISCLOSURE

The general purpose of the devices set forth in the present disclosure is to provide an intravascular guidewire filter system for pulmonary embolism protection and embolism removal or maceration, i.e., the breaking down of embolic debris into smaller pieces. The Primary and alternative embodiments consist of all or a plurality of basic components in combination, generally including one or more operator devices, a flexible 0.014" to 0.035" diameter guidewire, collapsible filters secured over and about the guidewire, a capture/delivery sheath, and a flexible mesh capture sleeve secured to the distal end of a capture sleeve positioning tube; many of the components are arranged telescopically.

The preferred embodiment of the present disclosure features a guidewire having a flexible proximal filter and a flexible distal filter located in tandem and proximal to a distal flexible tip. The flexible proximal filter and the flexible distal filter are constructed to provide for a gross filtration of embolic debris and are generally open in a proximal direction to accept the inflow of embolic debris and the like, whereas a filter end at the distal portion of the filter structure is structured with less porosity to capture pieces of embolic debris. The proximal ends of the proximal filter and the distal filter are fixed to the guidewire while the distal ends are free to traverse along, over and about the guidewire to facilitate the collapsing of each filter when the capture/delivery sheath or the capture/delivery sheath and the flexible mesh capture sleeve in sequence are advanced by operating devices over the proximal filter and the distal filter whereby the filters interface with and process debris in several ways. The capture/delivery sheath and the capture sleeve together can cause the filters to lengthen and cause the filters to easily collapse therein. At this conjuncture, two forms of embolic debris removal or treatment are used, one form is the direct physical engagement of the filters with the embolic debris and the other forum is the direct physical engagement of the filters with the embolic debris in combination with thrombolytics. In the first form, large embolic debris is trapped. If the embolic debris is proximal to the proximal filter, a thrombectomy catheter, such as an AngioJet® thrombectomy device or potentially an aspiration catheter may be used to remove the embolic debris. If the embolic debris resides within one or more of the filters, then, as the filters are sheathed for retrieval, soft embolic debris will be macerated by one or more of the filters as they are sheathed. The distal filter is a backup to catch any larger soft embolic debris that is not caught by the proximal filter. Thus, as both proximal and distal filters are sheathed, all soft embolic debris is macerated into smaller pieces where some debris may be trapped and some debris of inconsequential size may flow distally, if not captured. In the case where the thrombus debris in the filters is tougher and organized, sheathing will capture the thrombus debris within the filters for debris removal. Situations where this form of debris destruction is a viable means of protection involve venous interventions where the small debris is resolved by the lungs. In the other form, arterial interventions using the above mentioned method and when used in combination with thrombolytics, the soft thrombus is broken into smaller debris which is readily dissolved by the thrombolytics.

According to one or more embodiments of the present disclosure, there is provided an intravascular guidewire filter system for pulmonary embolism protection and embolism removal or maceration including a flexible guidewire, a distal filter and a proximal filter each firmly and slideably affixed to the guidewire where each filter includes a proximally located open end and a distally located filter end, a capture/delivery sheath attached at its proximal end to a capture/delivery sheath operator which can be extended over a greater portion of the flexible guidewire, a flexible capture sleeve being open in a distal direction, and a capture sleeve positioning tube which is aligned within the capture/delivery sheath where the distal end of the capture sleeve positioning tube is attached to the proximal end of the capture sleeve and where the proximal end of the capture sleeve positioning tube is attached to a capture sleeve operator.

The devices of the present disclosure provide an intravascular emboli capture and retrieval system for intravascular embolism protection and embolism removal or maceration.

One significant aspect and feature of the devices of the present disclosure is the use of an intravascular guidewire filter system for pulmonary embolism protection and embolism removal or maceration which system comprises a telescoping capture mechanism having (a) a capture/delivery sheath and a capture/delivery sheath operator; (b) a guidewire having flexible distal and proximal filters with a preformed memory shape, and (c) a flexible capture sleeve (mesh), a capture sleeve positioning tube and a capture sleeve operator.

One significant aspect and feature of the devices of the present disclosure is a device that is used to capture, trap or macerate embolic debris either passively or actively without the need for stopping blood flow.

Another significant aspect and feature of the devices of the present disclosure is a device having one or more of nitinol filters mounted on a conventional guidewire.

Another significant aspect and feature of the devices of the present disclosure is a device having one or more nitinol filters which can be used to trap embolic debris.

Another significant aspect and feature of the devices of the present disclosure is a device having one or more nitinol filters which can be used to macerate embolic debris.

Another significant aspect and feature of the devices of the present disclosure is the use of filters which are designed for stiffness during embolic debris pulling use but which filters are collapsible for removal.

Another significant aspect and feature of the devices of the present disclosure is a device having one or more nitinol filters which can be used to remove embolic debris.

Another significant aspect and feature of the devices of the present disclosure is a device that uses filters which have an expanded memory position.

Another significant aspect and feature of the devices of the present disclosure is a device where the proximal end of a nitinol filter is fixedly and directly attached to guidewire.

Another significant aspect and feature of the devices of the present disclosure is a device where the distal end of a nitinol filter slideably engages a guidewire in order to allow collapsing or expanded deployment of the nitinol filter.

Another significant aspect and feature of the devices of the present disclosure is a device that uses filters which are deployed, such as, from the lumen of a capture/delivery sheath.

Another significant aspect and feature of the devices of the present disclosure is a device that uses filters which are deployed, such as, from the lumen of a delivery sheath and then retrieved through a separate capture sheath that has been exchanged with the delivery sheath over the guidewire.

Another significant aspect and feature of the devices of the present disclosure is a device that uses filters which are compressible for proximal retraction, such as by the action of a capture/delivery sheath and/or a mesh capture sleeve.

Another significant aspect and feature of the devices of the present disclosure is a device having one or more filters generally open in a proximal direction to accept the inflow of embolic debris and a distal portion of the filter having a structure with a closer weave in order to capture pieces of embolic debris but which allows the flow of blood there through.

Another significant aspect and feature of the devices of the present disclosure is a device where proximal/distal configurations can use as many filters as needed and in any shape and size as desired.

Another significant aspect and feature of the devices of the present disclosure is the use of a flexible mesh capture sleeve which can be all nitinol or which can be nitinol with a polymer interwoven therein to interface with embolic debris.

Another significant aspect and feature of the devices of the present disclosure is a device having filter diameters from 2 mm to 48 mm.

Another significant aspect and feature of the devices of the present disclosure is a device where regular treatment devices can be passed over the proximal portion of the guidewire for use as a regular guidewire.

Another significant aspect and feature of the devices of the present disclosure is a device having the ability to capture large organized embolic debris.

Another significant aspect and feature of the devices of the present disclosure is a device having the ability to capture large and small embolic debris.

Another significant aspect and feature of the devices of the present disclosure is a device having the ability to temporarily capture debris which may later be removed by manual aspiration or by the use of an AngioJet® thrombectomy device and catheter or which may be treated by thrombolytics.

Another significant aspect and feature of the devices of the present disclosure is a device having the ability to macerate debris to a clinically insignificant size (depending on the area of the body) or to a size which can be pharmacologically treated or removed by another device, such as an AngioJet® thrombectomy device and catheter.

Another significant aspect and feature of the devices of the present disclosure is a device having the ability to macerate non-embolic debris, such as a stationary thrombus, by pulling the device through such an obstruction.

Having thus briefly described one or more embodiments of the present disclosure, and having mentioned some significant aspects and features of the devices of the present disclosure, it is the principal object of the present disclosure to provide an intravascular guidewire filter system for pulmonary embolism protection and embolism removal or maceration or for use with other medical devices.

BRIEF DESCRIPTION OF THE DRAWINGS

Other objects of the present disclosure and many of the attendant advantages of the devices set forth in the present disclosure will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
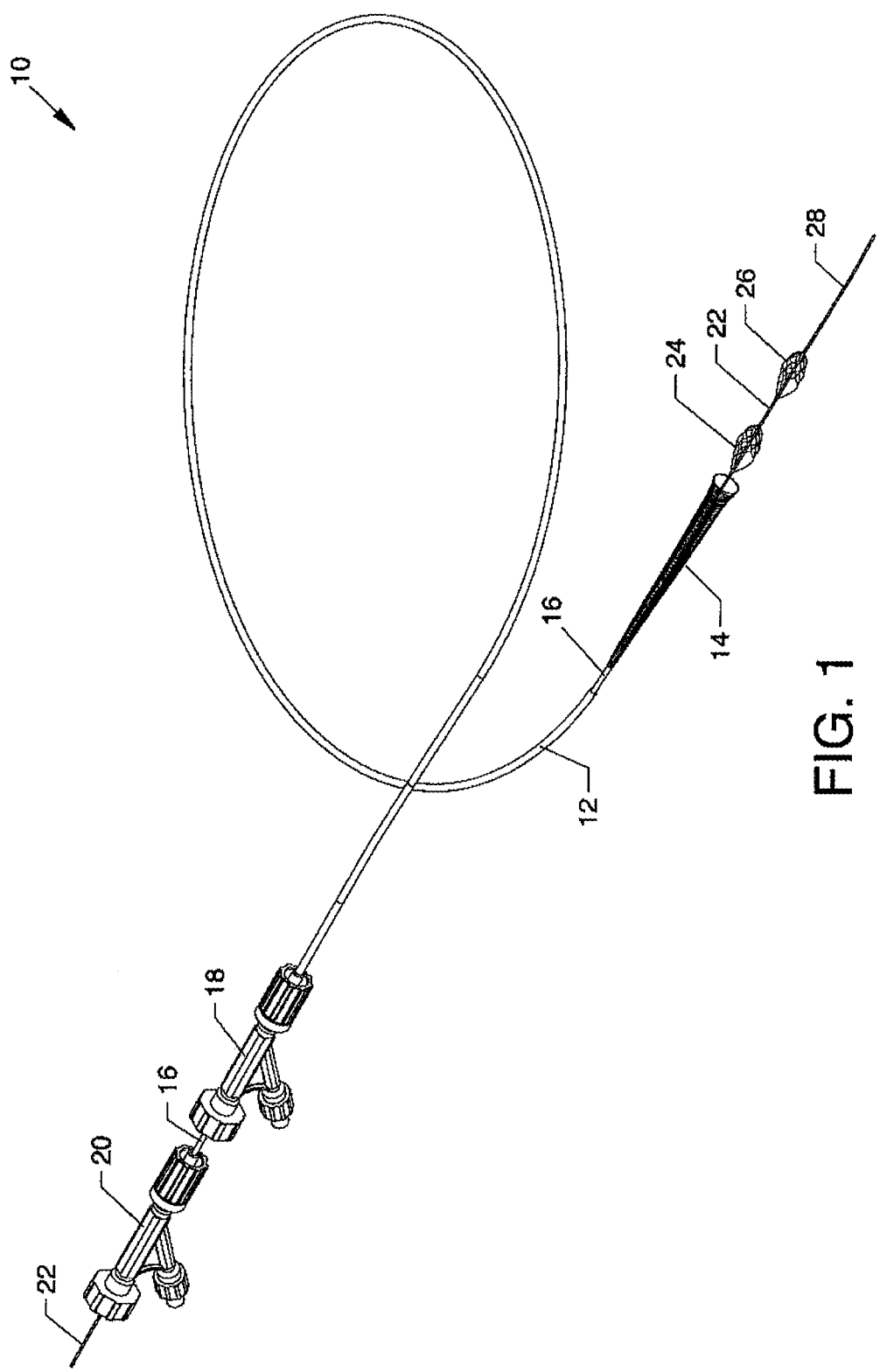
FIG. 1 is an isometric overview of the intravascular emboli capture and retrieval system for intravascular embolism protection and embolism removal or maceration.

FIG. 1 is an isometric overview of the intravascular emboli capture and retrieval system for intravascular embolism protection and embolism removal or maceration, 10. Generally, this preferred embodiment is useful in blood vessels of 8 mm or less to capture embolic debris, although maceration of such is also associated therewith. For vessels of larger than 8 mm in size, appropriate modifications to the sizing of the components of this embodiment, as known to those of skill in the art, are able to be freely substituted in order to capture or macerate emboli as dictated by each individual patient and scenario. Fully or partially visible components of the devices set forth in the present disclosure include a multiple function flexible capture/delivery sheath 12, a flexible distally located capture sleeve 14 shown in memory shape consisting of a nitinol and polymer mesh (shown in FIG. 3) secured to the distal end of a flexible capture sleeve positioning tube 16, the latter of which is shown extending distally from within the capture/delivery sheath 12, a capture/delivery sheath operator 18 in the form of a manifold attached to the proximal end of the capture/delivery sheath 12, a capture sleeve operator 20 in the form of a manifold in general longitudinal alignment with the capture/delivery sheath operator 18, a flexible guidewire 22 aligning with and extending through the capture sleeve operator 20, the capture/delivery sheath operator 18, the capture/delivery sheath 12, the capture sleeve positioning tube 16, through the capture sleeve 14 and through a flexible preformed memory shaped proximal filter 24 and a flexible preformed memory shaped distal filter 26. The guidewire 22 also includes a distally located flexible tip 28. The guidewire 22 can also be coated with a Teflon® coating.

Multiple function capture/delivery sheath 12 is depicted here as one aspect of the present disclosure. Those of skill in the art, however, are aware of the need to have a delivery sheath as small as possible in order to place filters 24 and 26 past the embolic debris. A large sheath is then required to act as the capture sheath since it also now contains embolic debris within the filters. It is well known in the art to perform an exchange of sheaths over a guidewire in order to facilitate specific actions during the procedure. All embodiments of the present disclosure should be read as including either a combination capture/delivery sheath or separately sized capture and delivery sheaths for these purposes.

Figure 2:
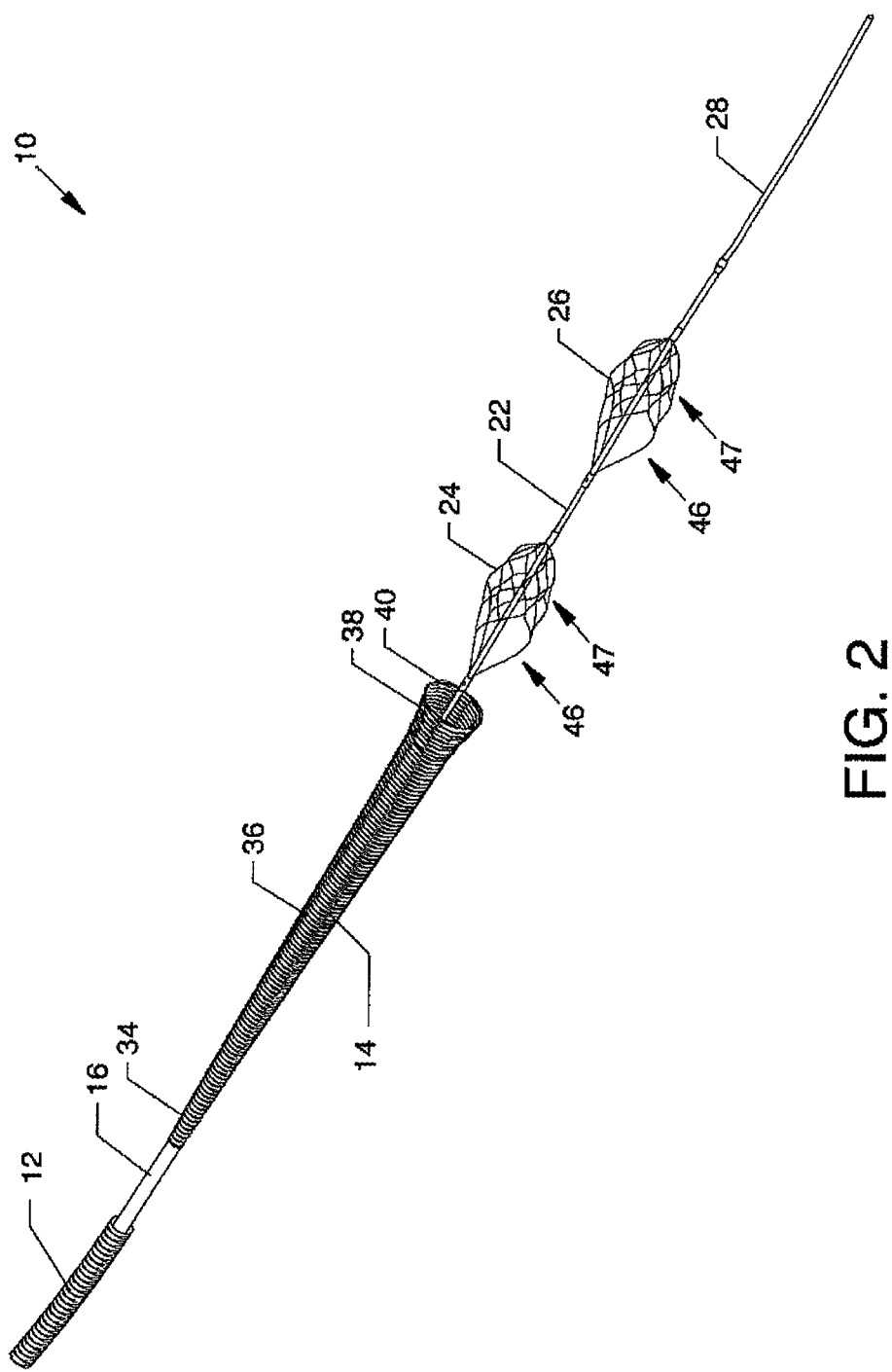
FIG. 2 is an isometric view of the components of the filter system located at the distal region of FIG. 1.

FIG. 2 is an isometric view of the components located at the distal region. The components maintain a coaxial relationship along and about the greater portion of the longitudinal axis comprising of inner, middle and outer components. The inner components consist of the guidewire 22, the proximal filter 24, the distal filter 26, and the flexible tip 28, the middle components consist of the capture sleeve 14 and the attached capture sleeve positioning tube 16, and the outer component consists of a capture/delivery sheath 12 made of a flexible spiral or woven flexible plastic material or other suitable flexible material. The inner, middle and outer components maintain a coaxial relationship. Some of the outer and middle components are also attached to the capture/delivery sheath operator 18 and the capture sleeve operator 20, respectively. More precisely, the capture sleeve 14 is attached to the capture sleeve operator 20 by a mutually attached capture sleeve positioning tube 16, and the capture/delivery sheath 12 is connected directly to the capture/delivery sheath operator 18. Preferably, the capture/delivery sheath 12 includes a hydrophilic coating to enhance deliverability along the vasculature or other structures and can be made of a flexible plastic material such as Pebax® plastic or another suitable flexible material.

Figure 3:
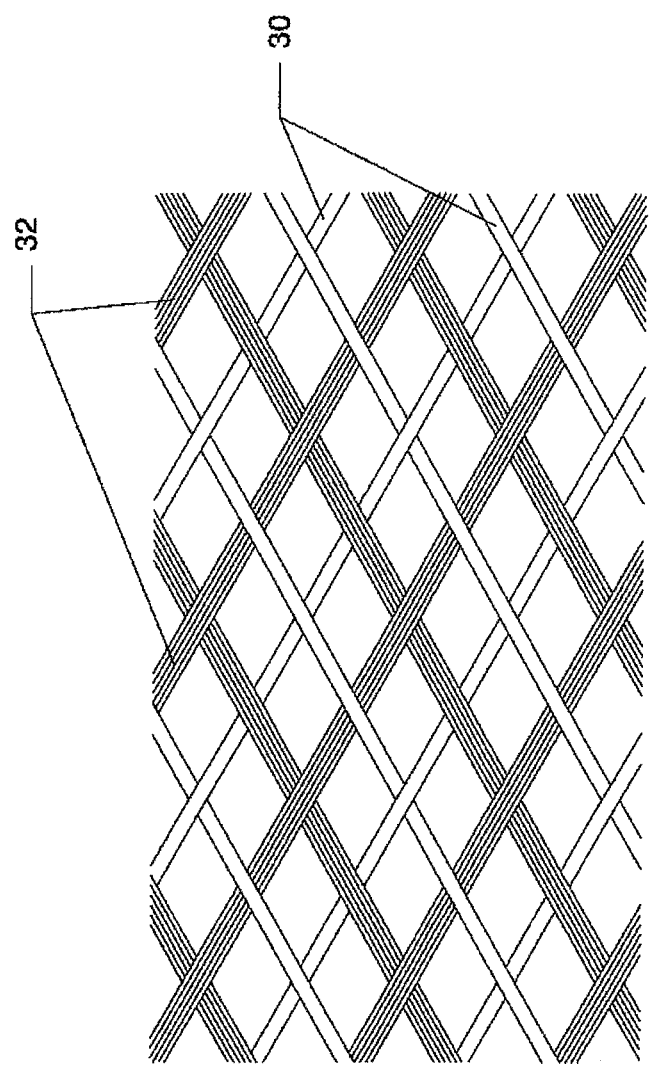
FIG. 3 is a view of the woven mesh comprising a flexible capture sleeve.

The geometrically configured flexible capture sleeve 14 is generally of a flared tubular shape and consists of a woven mesh preferably consisting of single nitinol strands 30 and multiple polymer strands 32, shown in a representative section in FIG. 3. The capture sleeve 14 is heat treated or otherwise treated to have an expanded memory shape. A substantially constant diameter proximal section 34 of the capture sleeve 14 is attached to the distal end of the flexible capture sleeve positioning tube 16 of braided polyimide, or alternatively of flexible stainless steel, by an adhesive, a weldment, or other suitable method. The capture sleeve 14 also includes a flared midsection 36 extending distally from the proximal section 34 to a flared distal section 38 where, preferably, the degree of flare of the flared distal section 38 exceeds the flare of the flared midsection 36 in order to readily accommodate entry of embolic debris or of a filter into the capture sleeve 14. Preferably, the flared midsection 36 and the flared distal section 38 can assume a memory expanded flare shape, but are conformal within a confine and are expandingly conformal to embolic debris which may be urged therethrough. The distal annular edge 40 of the capture sleeve 14 is prevented from fraying by melting the ends of the polymer strands 32 with a thermal or laser source or some other suitable method. The structure of the similarly constructed proximal filter 24 and the distal filter 26 are described in FIG. 4 and other figures.

Figure 4:
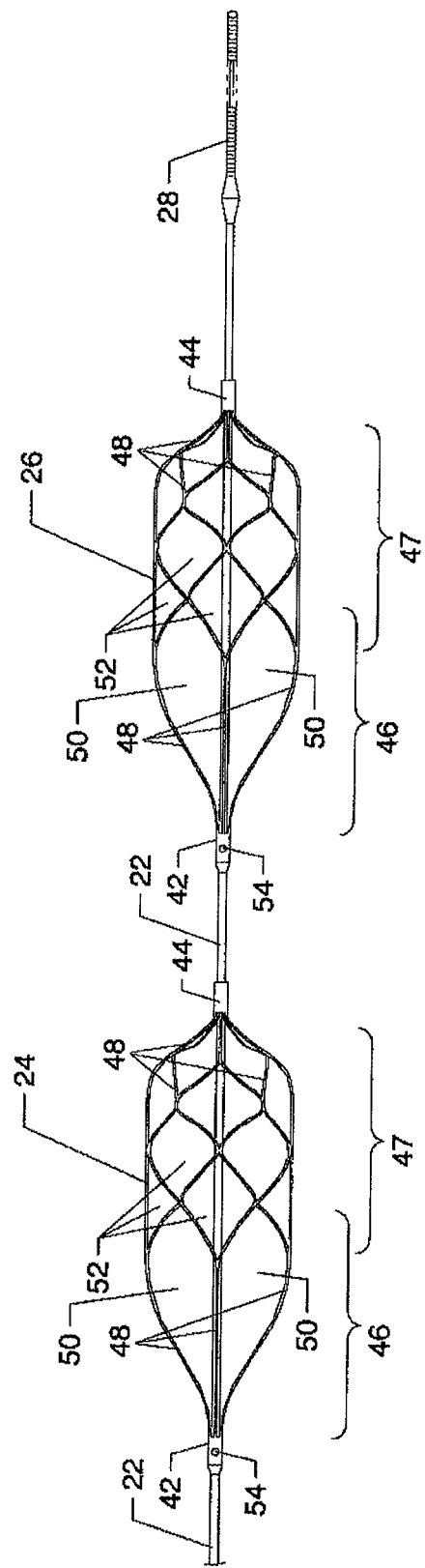
FIG. 4 is a side view of the distal end of the guidewire filter system including the similarly constructed preformed memory shaped proximal filter and distal filter.

FIG. 4 is a side view of the distal end of the guidewire 22 including the similarly constructed proximal filter 24 and distal filter 26. The preformed memory shaped proximal filter 24 and distal filter 26 are preferably formed as a one-piece structure where a configured multiply slotted nitinol tube has been expanded and heat treated in order to maintain a filter shape. The proximal tube 42 of the proximal filter 24 (and distal filter 26) is aligned over and about the guidewire 22 and is affixed and anchored thereto, preferably by the use of an adhesive which is applied through one or more holes 54 extending through the proximal tube 42 which, preferably, is or are aligned to one or more corresponding holes (not shown) in the guidewire 22. The distal tube 44 aligns over and about and slidingly engages the guidewire 22. The use of the fixed proximal tube 42 and the slideable distal tube 44 enables the proximal filter 24 and distal filter 26 to be flexibly and expandingly deployed and to be flexibly, compressingly and elongatingly collapsed along and about its longitudinal axis and along the guidewire 22, whereby a lower filter profile is provided in order to facilitate removal. Collapsing of the proximal filter 24 and distal filter 26 is assisted by engagement of the capture sleeve 14, the capture/delivery sheath 12, or both, as later described in detail. The proximal end of the proximal filter 24 (and distal filter 26) including the proximal tube 42 and the distal end of the proximal filter 24 (and distal filter 26) including the distal tube 44 have multiple strands of nitinol 48 extending therefrom and are distributed therebetween forming an angulated circumferential structure to provide openings which are substantially diamond shaped. For example, three widely spaced diverging nitinol strands 48 extend distally from the proximal tube 42 in order to form a proximally located open end 46 having multiple large openings 50. The nitinol strands 48 are further divided and then converge to form a plurality of small openings 52 in a band which are offset from and alternating with the band of the large openings 50. The division and convergence is repeated one or more times in a distal direction to create additional bands of small openings 52. The size of the small openings 52 is convergingly reduced adjacent the distal tube 44. The bands of small openings 52 forms the distally located filter end 47 which is in the shape of a tubular-like elongated web.

The large openings 50 are utilized for entry of an embolism or embolic or other debris into the proximal filter 24 and the distal filter 26. Depending on the size of the embolism or embolic debris, maceration may be partially accomplished by the initial impingement thereof on the nitinol strands 48 forming the large openings 50 at the open end 46. Subsequently, such macerated or appropriately sized embolisms or embolic or other debris can be filteringly captured by the plurality of small openings 52 forming the distally located filter end 47 to be further processed such as by compression, further macerated or a combination thereof using previously described components and features set forth herein. Although the large and small openings 50 and 52 are substantially diamond shaped, other shaped openings or configurations could also be used. The distal filter 24 and the proximal filter 26 and filters of alternative embodiments are shaped and designed for stiffness during use, but are flexible enough to be collapsed by compression during interaction with the capture/delivery sheath 12 and/or the nitinol mesh capture sleeve 14.

Figure 5:
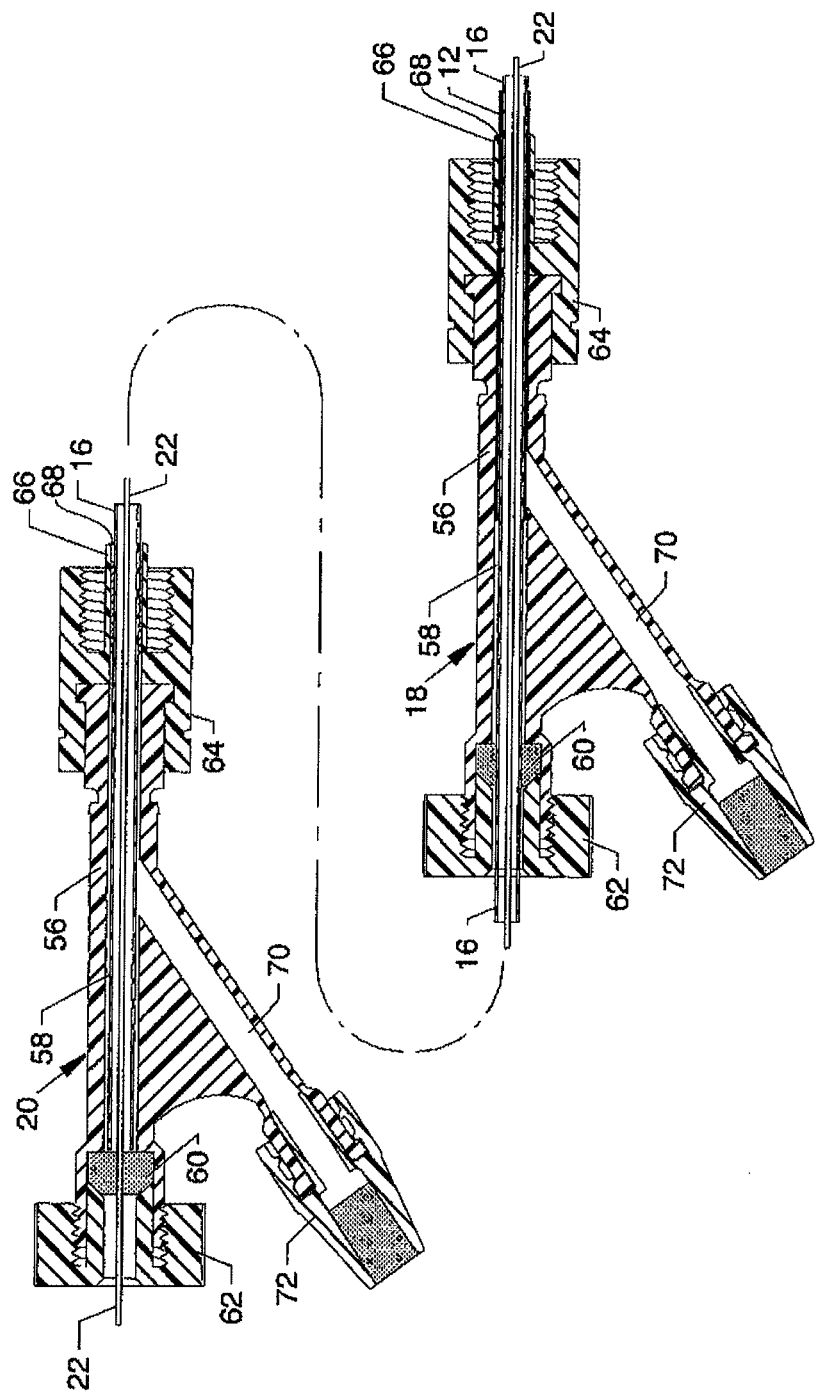
FIG. 5 is a segmented cross section view of the capture/delivery sheath operator and the capture sleeve operator.

FIG. 5 is a segmented cross section view of the capture/delivery sheath operator 18 and the capture sleeve operator 20, each in the faun of a manifold found commonly in the art. The capture/delivery sheath operator 18 and the capture sleeve operator 20 are used in a variable end-to-end alignment, such as shown in FIG. 1, and are used to telescopingly position the distally located components at the distal end using coaxially aligned tubular structures, the relationship of which is described with reference to FIG. 2. Briefly described, each operator includes a manifold body 56, a central passageway 58 extending along the manifold body 56, a seal 60, a hemostasis valve 62, a Luer connector 64, a tubular extension 66 (including a tubular passageway 68) extending through the Luer connector 64, a branch passageway 70 and a cap 72 which may be in the form of a Luer fitting.

The proximal end of the capture/delivery sheath 12 extends partially along the central passageway 58 of the capture/delivery sheath operator 18 and is positionally fixed therein by the use of an adhesive or another suitable method at the annular junction of the capture/delivery sheath 12 and the tubular extension 66 in the Luer connector 64 of the capture/delivery sheath operator 18. Generally, the capture/delivery sheath 12 can be positionably, telescopingly and variably aligned directly over, about and along portions of the capture sleeve positioning tube 16, over, about and along the connected capture sleeve 14, over, about and along the distal section of the guidewire 22, and over, about and along and the proximal filter 24 and the distal filter 26 which are located at the distal portion of the guidewire 22.

The proximal end of the capture sleeve positioning tube 16 extends partially within and along the central passageway 58 of the capture sleeve operator 20 and is fixed therein by the use of an adhesive or another suitable method at the annular junction of the capture sleeve positioning tube 16 and the tubular extension 66 in the Luer connector 64 of the capture sleeve operator 20. Additionally, the capture sleeve positioning tube 16 extends distally to enter the hemostasis valve 62, the seal 60, through the central passageway 58 of the capture/delivery sheath operator 18, and thence through the capture/delivery sheath 12 to finally connect to the distally located capture sleeve 14. The capture sleeve operator 20 can be used to slidingly position the capture sleeve positioning tube 16 (having the connected capture sleeve 14) along and within the capture/delivery sheath 12 in order to longitudinally position the capture sleeve 14 out of the influence of the capture/delivery sheath 12 or to return the capture sleeve 14 into the influence of the capture/delivery sheath 12. The seal 60 of the capture/delivery sheath operator 18 provides a slight pressure, which can easily be overcome, against the circumference of the capture sleeve positioning tube 16 in order to maintain the adjustable position of the capture sleeve positioning tube 16 with respect to the capture/delivery sheath operator 18 and to other associated telescopic components. Generally, as previously explained, the capture sleeve 14, which is connected to the capture sleeve positioning tube 16, can be positionably, telescopingly, and variably aligned directly over and about the guidewire 22 and the distal and proximal filters 24 and 26, respectively. Additionally, the seal 60 of the capture sleeve operator 20 provides a slight pressure which can be easily overcome against the circumference of the guidewire 22 in order to maintain the adjustable position of the guidewire 22 with respect to the capture sleeve operator 20 and to the other associated telescopic components.

Mode of Operation

The mode of operation of the intravascular guidewire filter system 10 for the filtering and removal of various sized pieces of organized embolic debris is now described with reference to FIGS. 6-9, as well as understood reference to previously described figures. In general, in this embodiment and in a closely related association with the alternative embodiments, one or more components may be preloaded prior to their use and are used in a telescopic fashion, whereby the capture/delivery sheath operator 18 and the capture sleeve operator 20 can be appropriately spaced and positioned longitudinally with respect to each other in order to change, affix, adjust or otherwise suitably influence the positional relationship of the distally located components, such as the capture/delivery sheath 12 and the capture sleeve 14 with respect to each other, as well as the closely associated and corresponding capture sleeve positioning tube 16. The guidewire 22, including the proximal filter 24 and the distal filter 26, is also positionable with respect to the components of the intravascular guidewire filter system 10 just referenced in this paragraph. The capture/delivery sheath operator 18, the capture sleeve operator 20 and the guidewire 22, including the attached proximal filter 24 and the distal filter 26 of this embodiment, can be operated independently one or more at a time in order to effect particular positional and functional relationships. The capture/delivery sheath operator 18 and the capture sleeve operator 20 associated with the capture/delivery sheath 12 and the capture sleeve 14 and associated positioning tubes, as well as the guidewire 22, can be operated individually or unitarily two or more at a time. In the alternative embodiments of the devices set forth in the present disclosure, the structure and/or use of the filters located on the guidewire 22, such as shown in use with the preferred embodiment, may be reoriented reconfigured, reversed, resized or otherwise changed or modified within the scope and teachings of the present disclosure to be used in lieu of the proximal filter 24 and/or the distal filter 26.

Figure 6:
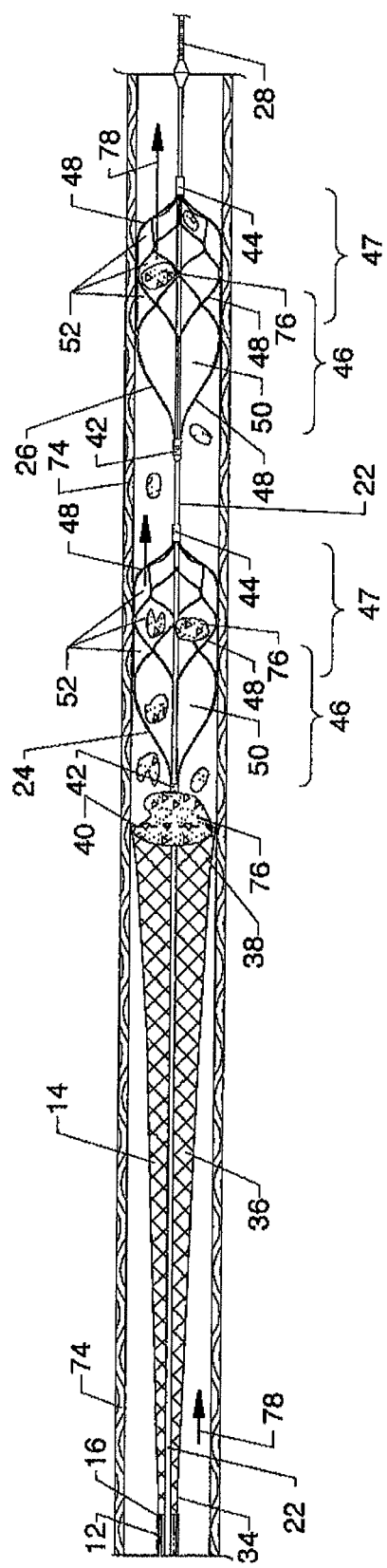
FIG. 6 is a view showing the proximal filter (in cutaway view) and the distal filter along the guidewire deployed and aligned in a blood vessel.

Use of the devices described in the present disclosure is initiated by insertion of the guidewire 22 and attached collapsed proximal filter 24 and distal filter 26 into the vasculature in cooperation with a smaller introducer sheath, such as known in the art, which is separate from the capture/delivery sheath 12. The distal end of the guidewire 22 and the proximal filter 24 and distal filter 26 are positioned through and beyond the embolic debris or area of treatment by use of the smaller introducer sheath, whereupon the smaller introducer sheath is removed in order to allow the automatic deployed expansion of the proximal filter 24 and the distal filter 26 which filters, preferably, intimately engage the inner circumference of a blood vessel 74 as shown in FIG. 6. The method of insertion into the vasculature of the guidewire 22 and attached collapsed proximal filter 24 and distal filter 26 in cooperation with a smaller introducer sheath, as set forth for this preferred embodiment, applies in general to one or more alternative embodiments on which, correspondingly, also include these or other automatically deployable, collapsible and expandable filters of various orientations, various features and various configurations. Interventional procedures or treatment, such as provided by, but not limited to, the use of an AngioJet® thrombectomy device and catheter, stenting or angioplasty could also be used at this point with protection against distally flowing embolic debris provided by the expanded proximal filter 24 and distal filter 26. Once the interventional procedure is complete, the physician could use fluoroscopy to verify that the proximal filter 24 and distal filter 26 were not occluded with embolic debris. Additionally, if there was an embolic thrombotic debris, an AngioJet® thrombectomy device and catheter could be advanced to treat any embolic debris proximal to the proximal filter 24 and the distal filter 26, as required.

Subsequent to the initial placement of the proximal filter 24 and the distal filter 26 and any interventional procedures, placement of stents, angioplasty or other treatments and trapping of the embolic debris, the capture/delivery sheath 12 including the capture sleeve 14 compressed and suitably located within the distal portion thereof, and also including the capture sleeve positioning tube 16, would engage and be delivered by simultaneous advancement distally over the guidewire 22 by distally directed positioning of the capture/delivery sheath operator 18 and the capture sleeve operator 20. Such delivery and advancement is continued until the capture sleeve 14 within the capture/delivery sheath 12 is in a position for suitable automatic expanded deployment to its memory shape proximal to the embolic debris trapped by the proximal filter 24 and the distal filter 26 by proximally directed positioning of the capture/delivery sheath 12 a short distance by manipulation of the capture/delivery sheath operator 18. The capture/delivery sheath 12, as thus distally positioned, is subsequently utilized and standing by for engagement over and about the distal filter 24 and the proximal filter 26 for capturing and removal of embolic thrombotic debris which is trapped by the proximal filter 24 and the distal filter 26, as later described in detail for this embodiment. With corresponding respect to this preferred embodiment and the alternative embodiments, delivery and positioning of the capture/delivery sheath 12 and the capture sleeve 14 is thus accomplished and such delivered components are standing by for the capture and removal of the embolic thrombotic debris which is trapped by automatically deployable, collapsible and expandable filters, such as the proximal filter 24 and the distal filter 26 of the preferred embodiment and filters of like orientation, various orientations, various features and various configurations of one or more alternative embodiments.

Thus, the initial placement of the guidewire 22, the attached proximal filter 24 and the distal filter 26, and the delivery and deployment of the capture sleeve 14, as well as the other associated structures have been described, the methods of which can generally be used with respect to both the preferred embodiment and the alternative embodiments. Capture and removal of entrapped embolic debris 76 is subsequently described with reference first to the preferred embodiment and with reference to the alternative embodiments wherein the general procedures are closely related or are the same.

In FIG. 6 and with respect to the preferred embodiment, a cutaway view is shown in partial cross section and partial cutaway view in the capture mode showing the proximal filter 24 (in cutaway view) and the distal filter 26 and the guidewire 22 deployed and aligned within a blood vessel 74 showing a large piece of embolic debris 76 located proximal to the proximal filter 24 being initially engaged by the flared distal section 38 of the capture sleeve 14. Other smaller pieces of embolic debris 76 are shown in the distally located filter end 47 of the proximal filter 24 which pieces have been deposited therein by passing through the openings 50 due to the force of blood flow as depicted by directional arrows 78. Also shown is embolic debris 76, which had not been engaged by the proximal filter 24, but which is engaged in the distally located filter end 47 of the distal filter 26. The capture sleeve 14, which has been expandingly deployed in the blood vessel 74 as previously described, is shown immediately proximal to the proximal filter 24. Each of the distal and proximal filters 26 and 24 is shown having engaged and trapped smaller embolic debris 76 of one shape or another.

Figure 7:
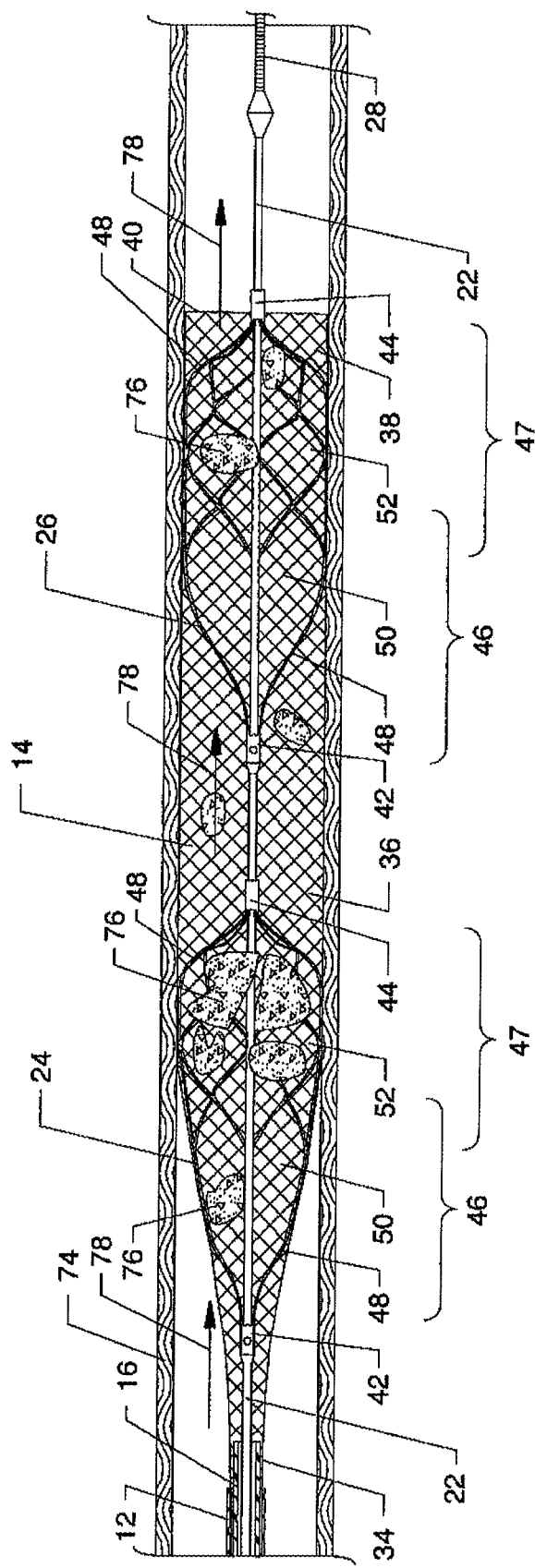
FIG. 7 is an illustration similar to FIG. 6 further showing the use of the capture sleeve in the capture mode in engagement over and about the proximal filter and the distal filter.

Engagement and entrapment of the embolic debris 76 can be accomplished either by the distal blood flow containing smaller pieces of embolic debris 76, as previously described, or by the manual forcible urging of the guidewire 22 and the connected proximal filter 24 and the distal filter 26 proximally to part, divide and macerate large pieces or collections of embolic debris 76 which are temporarily urged into and fixed in place in the capture sleeve 14 by contact caused by the proximal urging of the proximal filter 24. Some of the large pieces of embolic debris 76 can be parted, divided and macerated by forced contact with the strands 48 of the proximal filter 24 and can gain entry into the interior of the proximal filter 24 through the large openings 50 of the proximally located open end 46 during parting, dividing and macerating where entrapment is provided by the strands 48 at the small openings 52 in the distally located filter end 47, as shown in FIG. 7. Small particles of embolic debris 76 may pass directly through the large openings 50 for trapping by the strands 48 at the small openings 52 at the distally located filter end 47 of the proximal filter 24 without contacting the strands 48 of the large openings 50. To ensure more complete trapping and filtration, the embolic debris 76 which is not trapped by the proximal filter 24 can be trapped in the distal filter 26 in a similar manner just described. Preferably, blood flow as depicted by directed arrows 78 is monitored and entrapment of the embolic debris 76 within the proximal filter 24 and the distal filter 26 can be observed fluoroscopically or by other suitable methods in order to ensure blood flow through both the proximal filter 24 and the distal filter 26 during the filtering process.

FIG. 7 is an illustration similar to FIG. 6 further showing the use of the capture sleeve 14 in the capture mode by showing the engagement of the capture sleeve 14 over and about the proximal filter 24 and the distal filter 26, each of which has entrapped embolic debris 76 therein. Such engagement is accomplished by advancing the capture sleeve 14 distally toward and over the proximal filter 24 and the distal filter 26 by operation of the capture sleeve operator 20. The guidewire 22 can be cooperatively actuated proximally in order to intimately contact and pull and urge the large piece of embolic debris 76 into the capture sleeve 14 by impingement of the large piece of embolic debris 76 by the proximally directed proximal filter 24, through the flared distal section 38 and the annular edge 40 of the captive sleeve 14 and into the flared midsection 36, i.e., the confines of the capture sleeve 14. During such proximally directed urging of the large piece of embolic debris 76, the embolic debris 76 impinges upon the flared distal section 38 and the flared midsection 36 where the reduction of the flare of each capture sleeve section beneficially resists proximal movement of the impinging large piece of embolic debris 76. Such impingement and resistance to the movement temporarily fixes the position of the large piece of embolic debris 76, whereby the proximally urged strands 48 of the proximally directed proximal filter 24 forcibly part, divide and macerate the large piece of embolic debris 76 resulting in several smaller pieces, as shown, which can be subsequently trapped by the strands 48 of the small openings 52 of the distally located filter ends 47 or which can be forced through the strands 48 of the small openings 52 as smaller parted, divided and macerated pieces of embolic debris 76 which may then be trapped by the structure of the distal filter 26. Other smaller particles of embolic debris 76 can also be filteringly trapped by the distal filter ends 47 of each of the proximal and distal filters 24 and 26. Very small particles of embolic debris 76 which pass through the located filter ends 47 of the proximal filter 24 and the distal filter 26 may be of insignificant consequence and can pass downstream.

Figure 8:
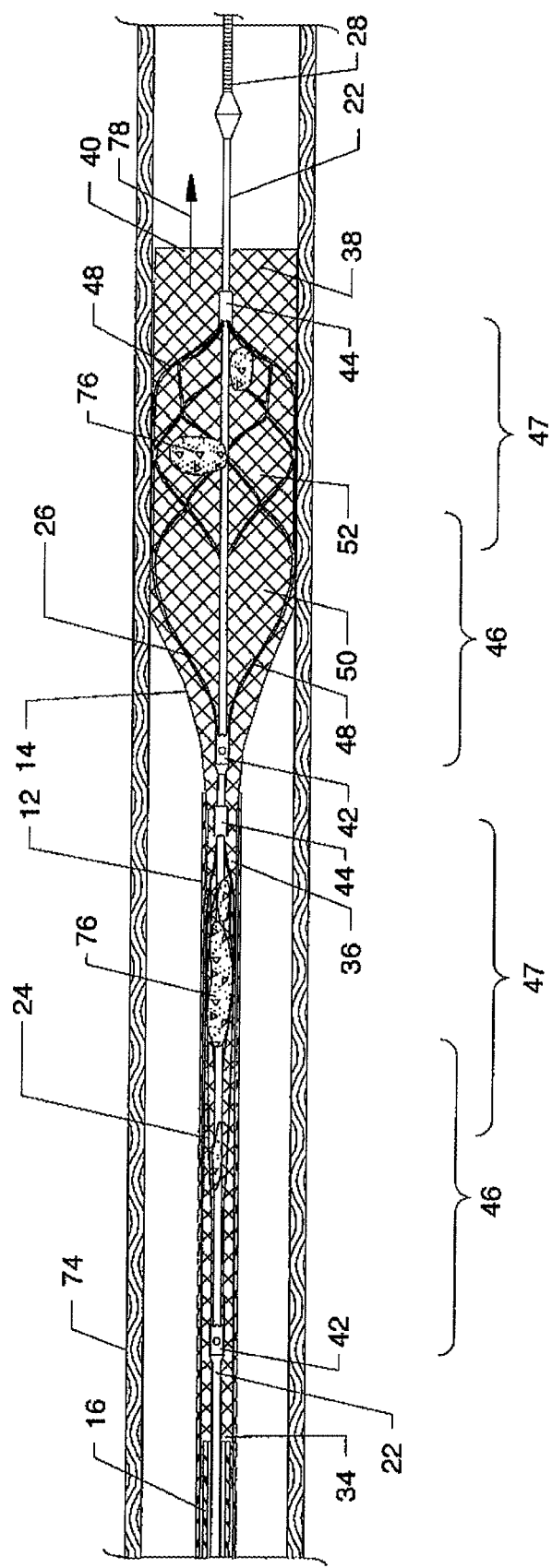
FIG. 8 is an illustration similar to FIG. 7 further showing the use of the capture sleeve and the capture/delivery sheath in the capture mode.

FIG. 8 is an illustration similar to FIG. 7 further showing the use of the capture sleeve 14 and the capture/delivery sheath 12 in the capture mode. Operation of the capture/delivery sheath operator 18 forces the capture/delivery sheath 12 distally, whereby the distal end of the capture/delivery sheath 12 is progressively positioned directly over and about the capture sleeve 14 and, simultaneously, is progressively and indirectly positioned over and about the proximal filter 24 which is coaxially aligned within the capture sleeve 14. Such distal progressive distal positioning of the capture/delivery sheath 12 forcibly compresses the capture sleeve 14, the underlying proximal filter 24 and the embolic debris 76 which has been captured within the proximal filter 24. During compression, the embolic debris 76 can also be elongated or may beneficially be further parted, divided and macerated into smaller pieces.

Figure 9:
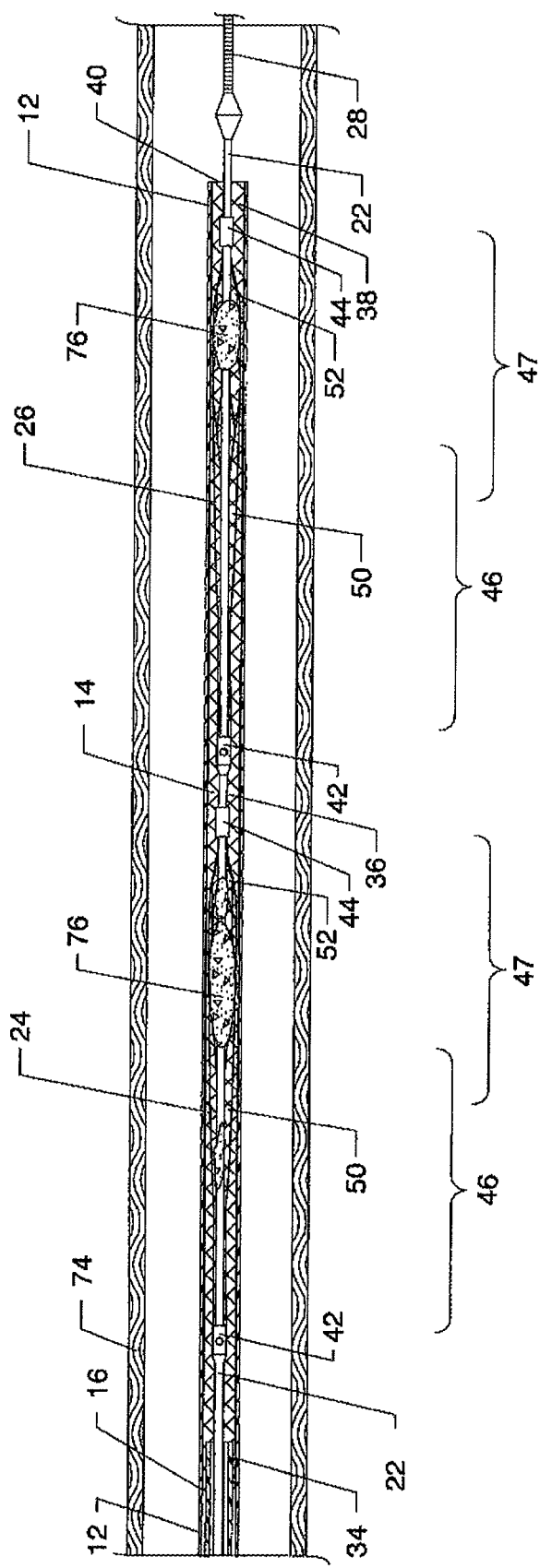
FIG. 9 is an illustration, similar to FIG. 8 further showing the use of the capture sleeve and the capture/delivery sheath in the capture mode.

FIG. 9 is an illustration similar to FIG. 8 further showing the use of the capture sleeve 14 and the capture/delivery sheath 12 in the capture mode. In this illustration, the capture/delivery sheath 12 is positioned further and fully in a distal direction to force complete compression of the capture sleeve 14 where the capture/delivery sheath 12 is in alignment directly over and about the distal portion of the capture sleeve 14 and simultaneously is indirectly and compressingly positioned over and about the distal filter 26 which is in coaxial alignment within the distal portion of the capture sleeve 14. Complete compression of the capture sleeve 14 indirectly over and about the proximal filter 24 and the embolic debris 76 captured therein and indirectly over and about the distal filter 26 and the embolic debris 76 captured therein and directly over and about the capture sleeve 14 provides a low profile structure of such components containing captured embolic debris 76. Components of such low profile structure containing captured embolic debris 76 may be readily withdrawn, preferably in simultaneous fashion, proximally through the capture/delivery sheath 12 where the capture sleeve positioning tube 16, the embolic debris laden capture sleeve 14, the guidewire 22 and the compressed embolic debris laden proximal filter 24 and distal filter 26 are withdrawn in a proximally directed removal from the capture/delivery sheath 12 by a proximal and manual directed unitary movement of the capture/delivery sheath operator 18, the capture sleeve operator 20 and attached capture sleeve positioning tube 16, and the guidewire 22. In the alternative, the capture sleeve positioning tube 16, the embolic debris laden capture sleeve 14, the guidewire 22 and proximal filter 24 and distal filter 26 and the capture/delivery sheath 12 may be entirely and unitarily withdrawn from the blood vessel 74 by the proximal and manual directed movement of the capture/delivery sheath operator 18, the capture sleeve operator 20 and the guidewire 22. Such removal is closely and generally related to or is the same for the later described alternative embodiments.

Figure 10:
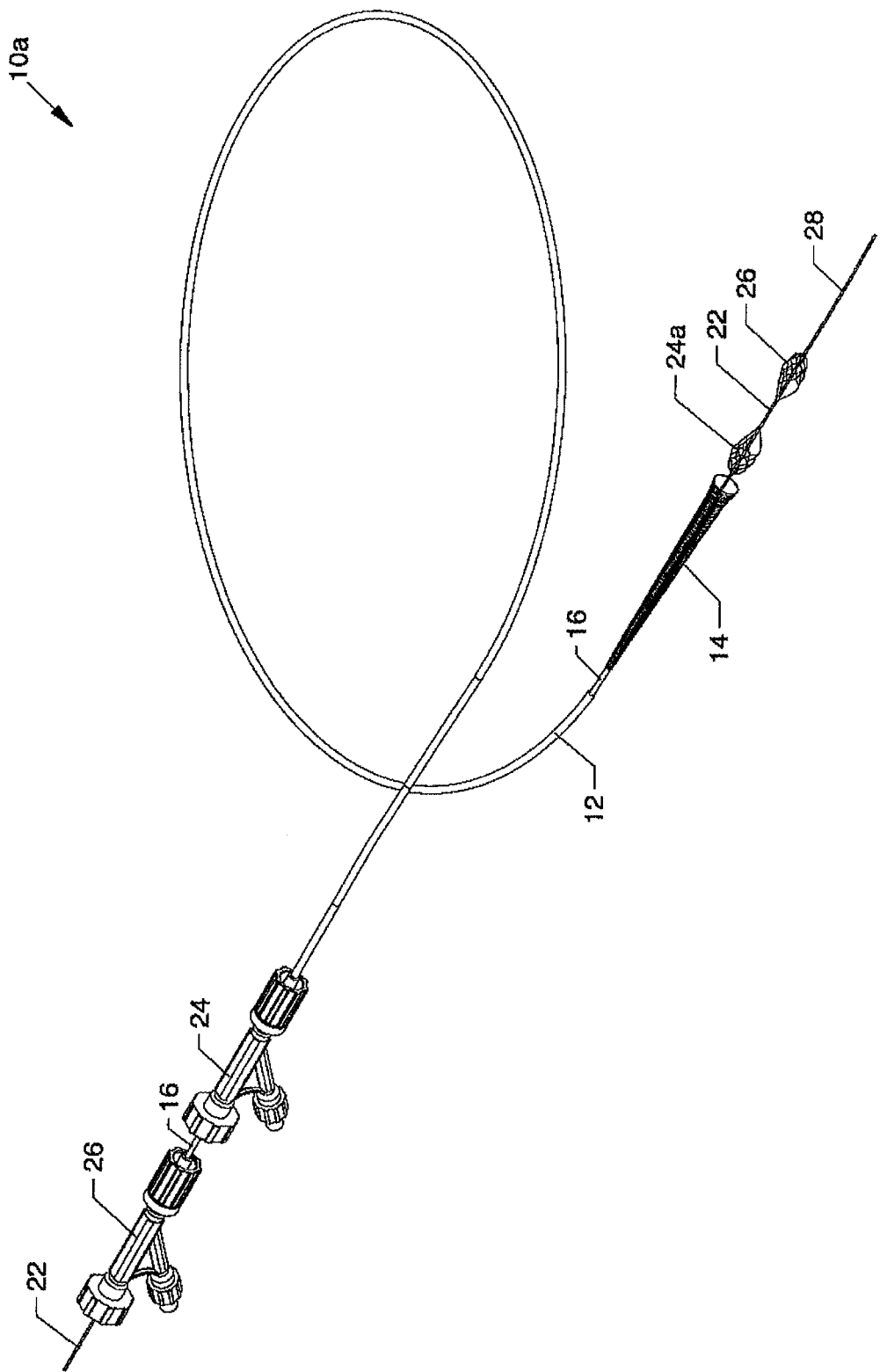
FIG. 10, a first alternative embodiment, is an isometric overview of the intravascular guidewire filter system for pulmonary embolism protection and embolism removal or maceration.

FIG. 10, a first alternative embodiment, is an isometric overview of the intravascular emboli capture and retrieval system for intravascular embolism protection and embolism removal or maceration, 10a. Generally, this alternative embodiment is useful in blood vessels of 8 mm or less to capture embolic debris although maceration of such debris is also associated therewith and is used in much the same manner as previously described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This first alternative embodiment is similar to the preferred embodiment of FIG. 1 with the exception of the arrangement, reorientation or modification of one or more filters and the use thereof. A flexible preformed memory shaped proximal filter 24a of this first alternative embodiment which can be deployed proximal to a large embolic debris 76 is used in lieu of the preformed memory shaped proximal filter 24 of the preferred embodiment and is located on the guidewire 22 and is generally of the same shape but with slightly modified features and is reversely oriented. Such reorientation provides for the use of a robust and close filter weave of the filter end 47 for proximally directed pulling of a large piece of organized embolic debris 76 or embolic debris collection by the proximal filter 24a. Also provided, in the alternative, is the ability to deploy the proximal filter 24a and the distal filter 26 such that the embolic debris 76 is located therebetween whereby the proximal filter 24a and the distal filter 26 could be alternately urged proximally and distally to cause an impingement of the strands 48 of the proximal filter 24a and the distal filter 26 with the embolic debris 76, as described later in detail.

Figure 11:
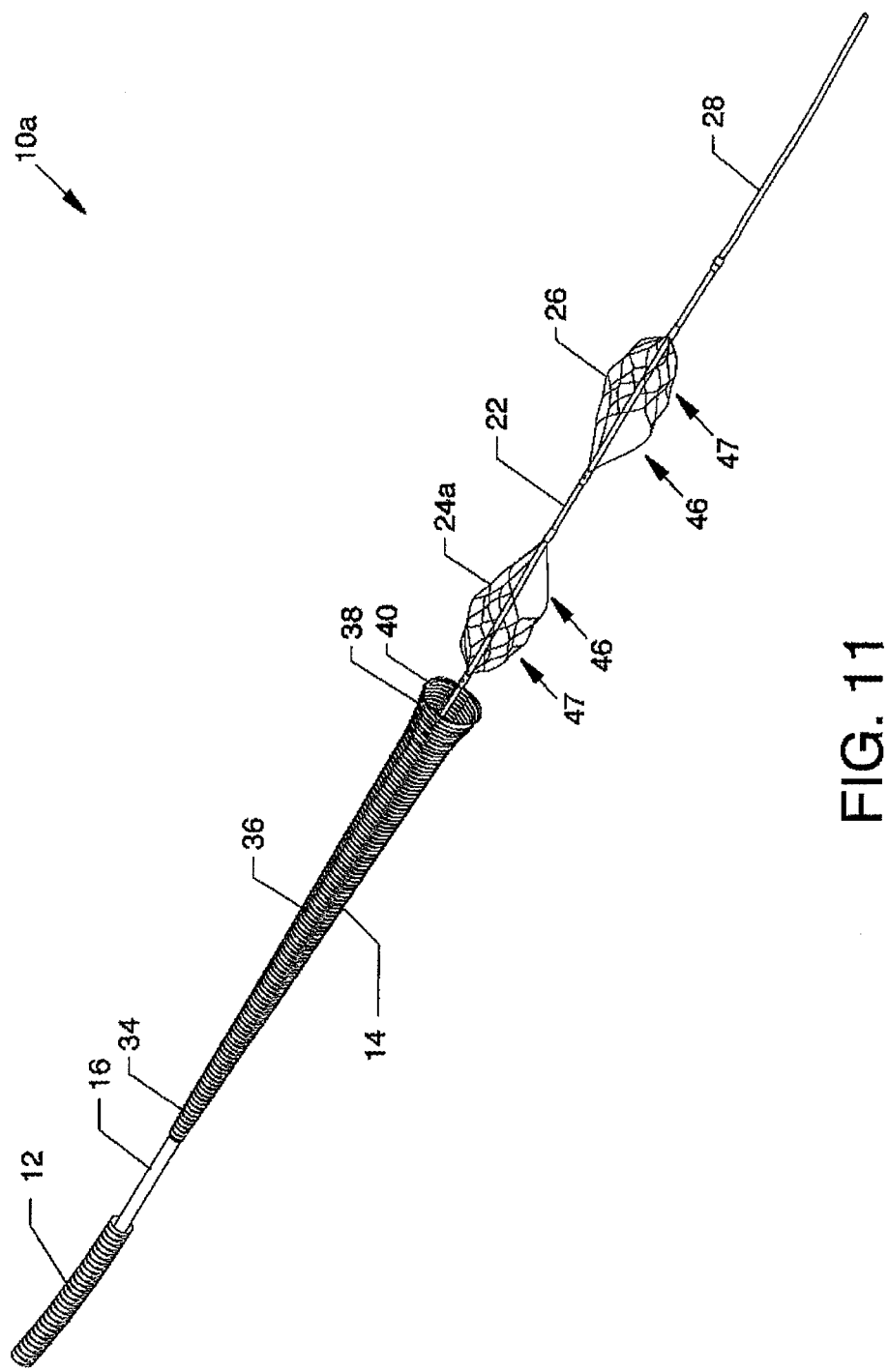
FIG. 11 is an illustration similar to FIG. 2 and is an isometric view of the components located at the distal region of a first alternative embodiment.

FIG. 11 is an illustration similar to FIG. 2 and is an isometric view of the components located at the distal region of the first alternative embodiment of the present disclosure. Shown, in particular, is the relationship of the proximal filter 24a to the capture sleeve 14 and to the distal filter 26.

Figure 12:
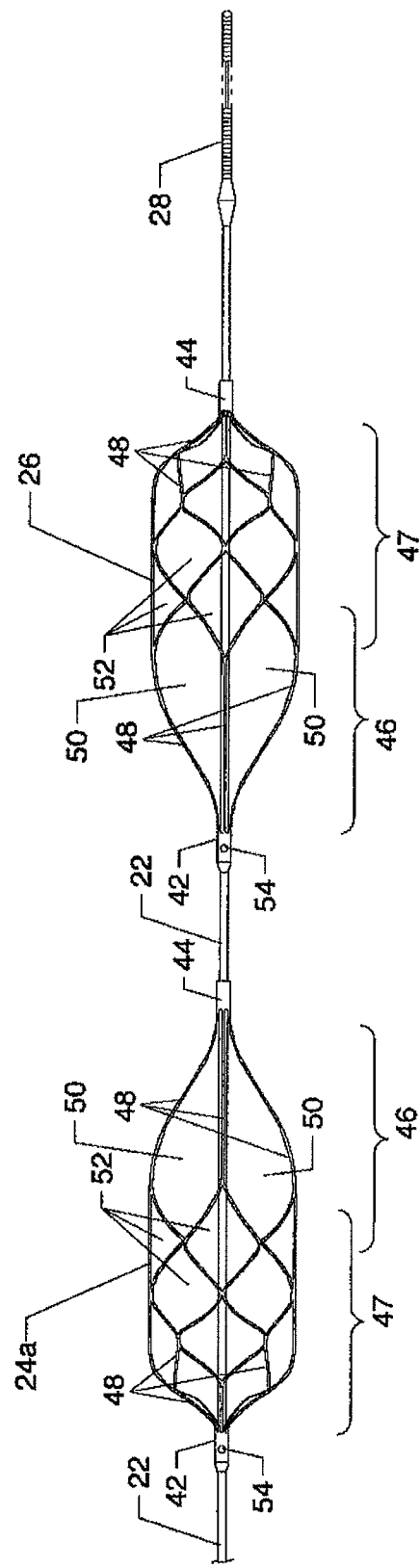
FIG. 12 is an illustration similar to FIG. 4 and is a side view of the distal end of a guidewire including a preformed memory shaped proximal filter and a preformed memory shaped distal filter.

FIG. 12 is an illustration similar to FIG. 4 and is a side view of the distal end of the guidewire 22 including the preformed memory shaped proximal filter 24a and the preformed memory shaped distal filter 26. The structure of the proximal filter 24a is similar to but differs slightly from the proximal filter 24 and the distal filter 26 of the preferred embodiment. More specifically, features of the proximal filter 24 including the strands 48, the large openings 50 and the small openings 52, are reoriented and reversed in order to form the proximal filter 24a which is located between the proximal tube 42 and the distal tube 44, as shown, whereby the open end 46 and the filter end 47 are also reoriented and reversed. The location of the proximal tube 42 and the distal tube 44 is unchanged. The distal tube 44 is aligned over and about the guidewire 22 and is in sliding engagement with the guidewire 22. The use of the fixed proximal tube 42 and the slideable distal tube 44 enables the proximal filter 24a and distal filter 26 to be flexibly and expandingly deployed and to be flexibly, compressingly and elongatingly collapsed along and about their longitudinal axis and along the guidewire 22, whereby a lower filter profile is provided.

Mode of Operation

The mode of operation of the first alternative embodiment of the intravascular guidewire filter system 10a for the filtering and removal of various sized pieces of organized embolic debris is now described with reference to FIGS. 13-15, as well as understood reference to previously described figures. The capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached proximal filter 24a and distal filter 26 as required during various delivery and capture phases, such as previously described with reference to the preferred embodiment.

Engagement and entrapment of smaller pieces of the embolic debris 76 in the distal filter 26 can be accomplished by the distal blood flow containing smaller pieces of embolic debris 76, as previously described. Engagement and entrapment of large embolic debris 76 can be accomplished by the judicious placement of the proximal filter 24a and the distal filter 26 with respect to the large embolic debris 76. In a first scenario and with respect to the large embolic debris 76, the guidewire 22 is deployed to position the proximal filter 24a distal to a large piece of embolic debris 76, and in a second scenario, the guidewire 22 is deployed to position the proximal filter 24a proximal to the large embolic debris 76 and the distal filter 26 is deployed distal to the large embolic debris 76 and used as described herein.

Figure 13:
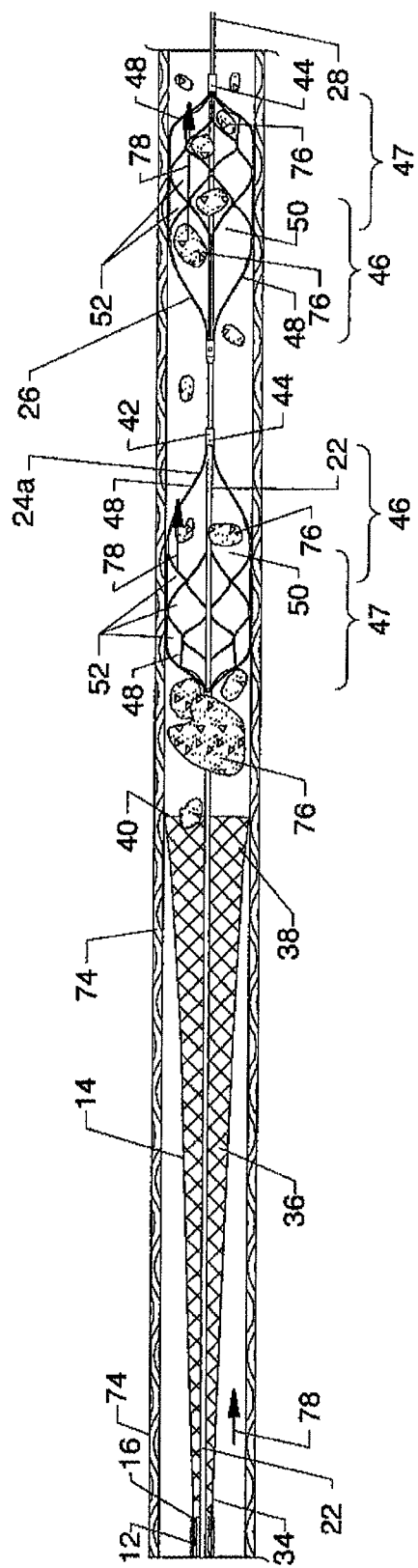
FIG. 13 is a cutaway view in partial cross section and partial cutaway view in the capture mode of the first alternative embodiment showing the proximal filter (in cutaway view), the distal filter and the guidewire deployed and aligned within a blood vessel.

In the first scenario, such as shown in FIG. 13 and with respect to the first alternative embodiment, a cutaway view is shown in partial cross section and partial cutaway view in the capture mode showing the proximal filter 24a (in cutaway view), the distal filter 26 and the guidewire 22 deployed and aligned within a blood vessel 74 showing a large piece of embolic debris 76 located proximal to the proximal filter 24a prior to initial engagement of the proximal and distal filters 24a and 26 by the flared distal section 38 of the capture sleeve 14. The capture sleeve 14 which has been expandingly deployed in the blood vessel 74, as previously described in the preferred embodiment, is shown immediately proximal to the proximal filter 24a. Manual positioning of the guidewire 22 in a proximal direction causes the deployed filter end 47 of the proximal filter 24a to engage and urge the large piece of embolic debris 76 proximally into the flared distal section 38 of the capture sleeve 14, the latter of which may be urged distally to cooperatively accommodate the large piece of embolic debris 76. The large piece of embolic debris 76 does not contact the strands 48 of the large openings 52 for parting, dividing and macerating, but instead encounters the relatively fine weave of the strands 48 at the filter end 47 located on the proximal filter 24a which filter end 47 wholly engages the large piece of embolic debris 76 with minimum, if any, parting, dividing or macerating. Also shown in the illustration is an embolic debris 76 of smaller size which had not been engaged by the proximal filter 24a, but which is engaged in the distally located filter end 47 of the distal filter 26. Each of the distal and proximal filters 26 and 24a is shown having engaged and trapped smaller embolic debris 76 of one shape or another.

Figure 14:
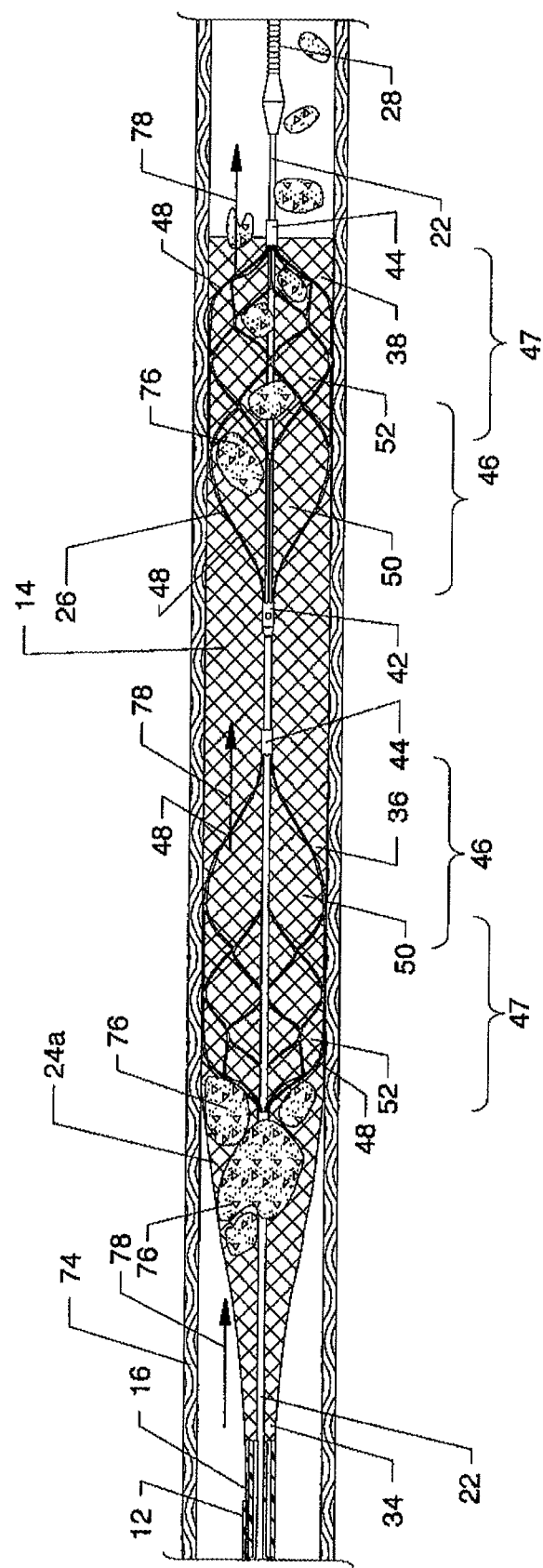
FIG. 14 is an illustration similar to FIG. 13 further showing the capture mode and demonstrating the engagement of the capture sleeve over and about the proximal filter, the distal filter, and large pieces of embolic debris.

FIG. 14 is an illustration similar to FIG. 13 further showing the capture mode and demonstrating the engagement of the capture sleeve 14 over and about the proximal filter 24a and the distal filter 26 and of a large piece of embolic debris 76, the latter of which has been urged into the interior of the capture sleeve 14. Operation of the capture sleeve operator 20 and the capture/delivery sheath operator 18 is used to position the capture sleeve 14 and the capture/delivery sheath 12, respectively, in concert with the movement of the guidewire 22 and the attached proximal filter 24a and distal filter 26 during various delivery and capture phases, such as previously described with reference to the preferred embodiment.

Figure 15:
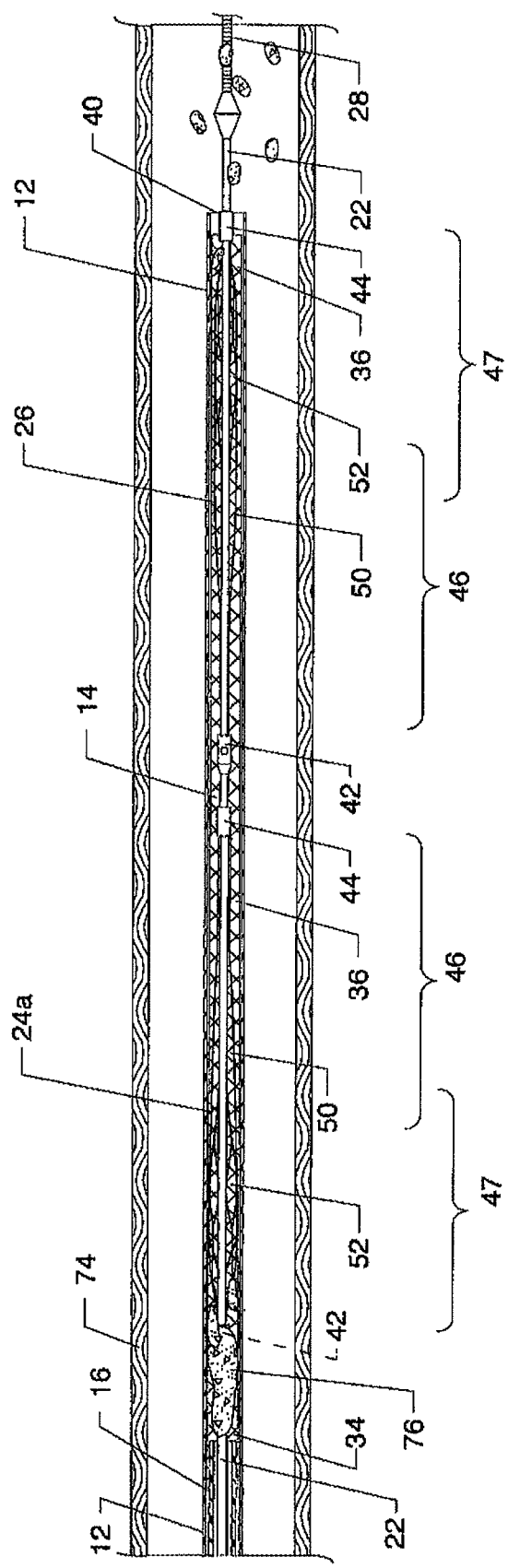
FIG. 15 is an illustration further showing and demonstrating the use of the capture sleeve and the capture/delivery sheath in the capture mode.

FIG. 15 is an illustration showing and demonstrating the use of the capture sleeve 14 and the capture/delivery sheath 12 in the capture mode. More specifically, collapsing of the proximal filter 24a and the distal filter 26 is assisted by engagement of the capture sleeve 14, the capture/delivery sheath 12, or both, in a manner as previously described in detail. In this illustration, the capture/delivery sheath 12 is positioned directly over and about the capture sleeve 14 in order to provide complete compression of the capture sleeve 14 and indirectly and compressingly over and about the proximal filter 24a and the embolic debris 76 captured therein and indirectly and compressingly over and about the distal filter 26 and any embolic debris 76 captured therein to enable a low profile structure of such components containing captured large or small embolic debris 76. Such a low profile structure of such components containing captured embolic debris 76 may be readily withdrawn, preferably in a manner and fashion as previously described with respect to the preferred embodiment.

Figure 16:
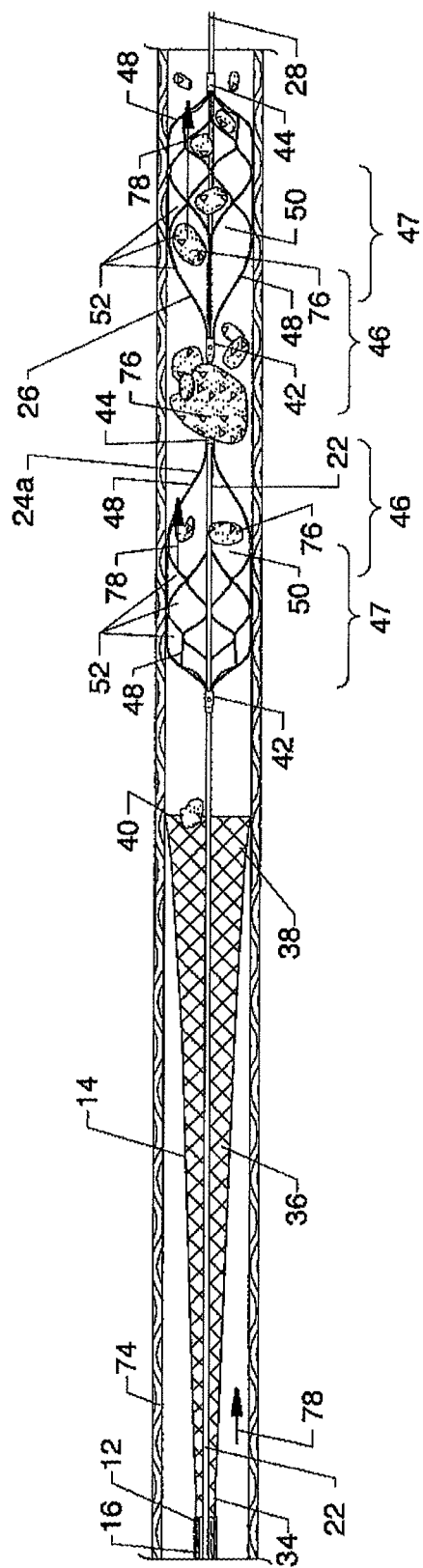
FIG. 16 shows the guidewire deployed to position an expanded proximal filter proximal to a large embolic debris with an expanded distal filter deployed and positioned distal to the large embolic debris.

In the second scenario, such as shown in FIG. 16, the guidewire 22 is deployed to expandingly position the proximal filter 24a proximal to the large embolic debris 76 and the distal filter 26 is deployed and expandingly positioned distal to the large embolic debris 76. The guidewire 22 is alternately positioned distally and proximally to cause the proximal filter 24a and the distal filter 26 to impinge opposing ends of the large embolic debris 76, whereupon urging of the guidewire 22 distally causes the engagement of the strands 48 at the open end 46 of the proximal filter 24a with the large embolic debris 76 which is parted, divided and macerated and which debris enters the large openings 50 for capture in the filter end 47 formed by the strands 48, and whereupon urging of the guidewire 22 proximally causes engagement of the strands 48 at the open end 46 of the distal filter 26 with the large embolic debris 76 which is parted, divided and macerated and which debris enters the large openings 50 for capture in the filter end 47 formed by the strands 48.

Figure 17:
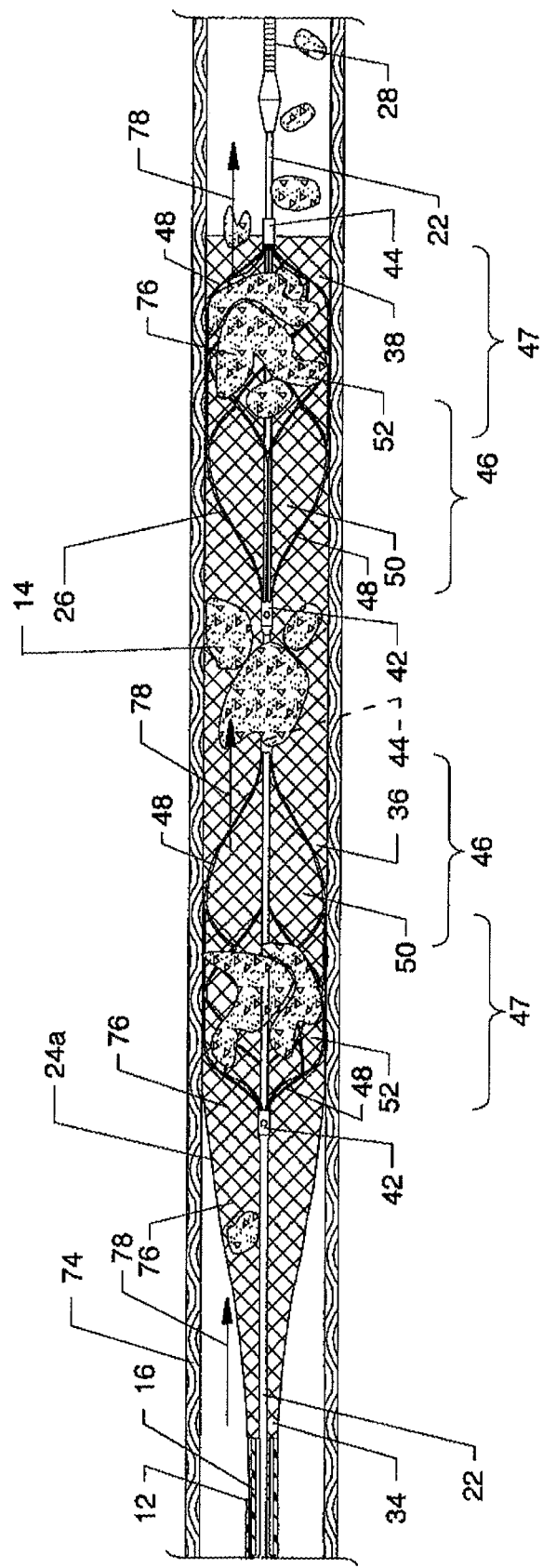
FIG. 17 is similar to FIG. 14 further showing the capture mode and demonstrating the engagement of the capture sleeve over and about the proximal filter and the distal filter and parts of one or more pieces of the large piece of embolic debris.

FIG. 17 is similar to FIG. 14 further showing the capture mode and demonstrating engagement of the capture sleeve 14 over and about the proximal filter 24a and the distal filter 26 and of parts of one or more pieces of the large embolic debris 76, the latter of which has been parted, divided and macerated and deposited into either or both proximal filter 24a and distal filter 26, such as described with reference to FIG. 16, and which await withdrawal of a low profile configuration wherein the capture/delivery sheath 12 and other components are utilized for compression and withdrawal of the capture sleeve 14, the proximal filter 24b, the distal filter 26 and the embolic debris 76 associated therewith in a manner as previously described and shown in FIG. 15.

Figure 18:
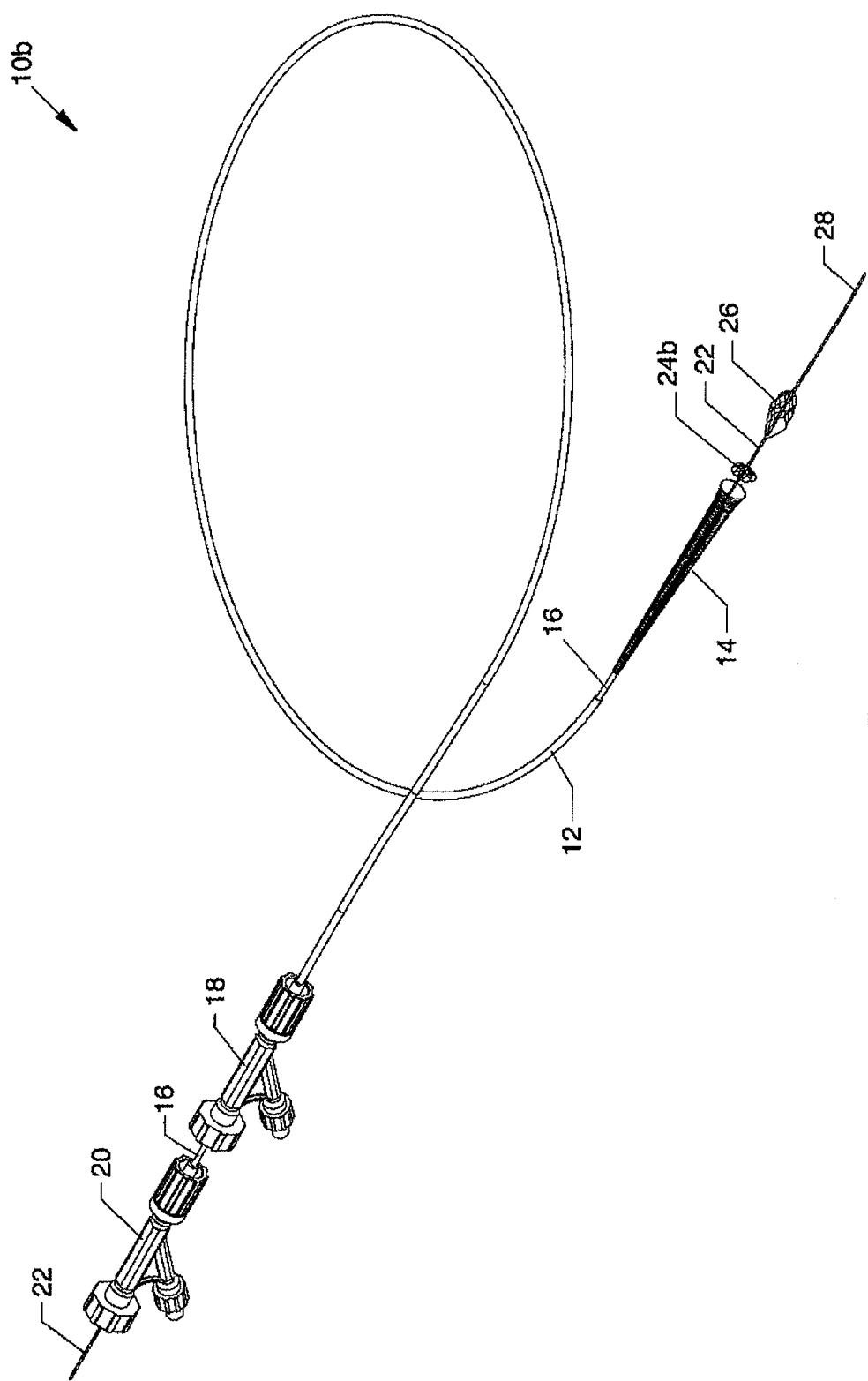
FIG. 18, a second alternative embodiment, is an isometric overview of the intravascular emboli capture. and retrieval system for intravascular embolism protection and embolism removal or maceration.

FIG. 18, a second alternative embodiment, is an isometric overview of the intravascular emboli capture and retrieval system for intravascular embolism protection and embolism removal or maceration, 10b. Generally, this alternative embodiment is useful in blood vessels of 8 mm or less to capture embolic debris, although maceration of such is also associated therewith and is used much in the same manner as described for use in the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This second alternative embodiment is similar to the preferred embodiment of FIG. 1 with the exception of the arrangement, reorientation or modification of one or more filters and use thereof. A flexible preformed memory shaped proximal filter 24b of this second alternative embodiment, which can be deployed distal to a large embolic debris 76, is used in lieu of the preformed memory shaped proximal filter 24 of the preferred embodiment and is located on the guidewire 22 and, in general, is of an alternate shape and configuration. The concave basket-like flexible preformed memory shaped proximal filter 24b is open in a proximal facing direction to present its concave shaped side to the blood flow and to a proximally located large piece of embolic debris 76. The proximal filter 24b provides a robust and suitable filter weave for pulling a large piece of organized embolic debris 76 or embolic debris collection in a proximal direction.

Figure 19:
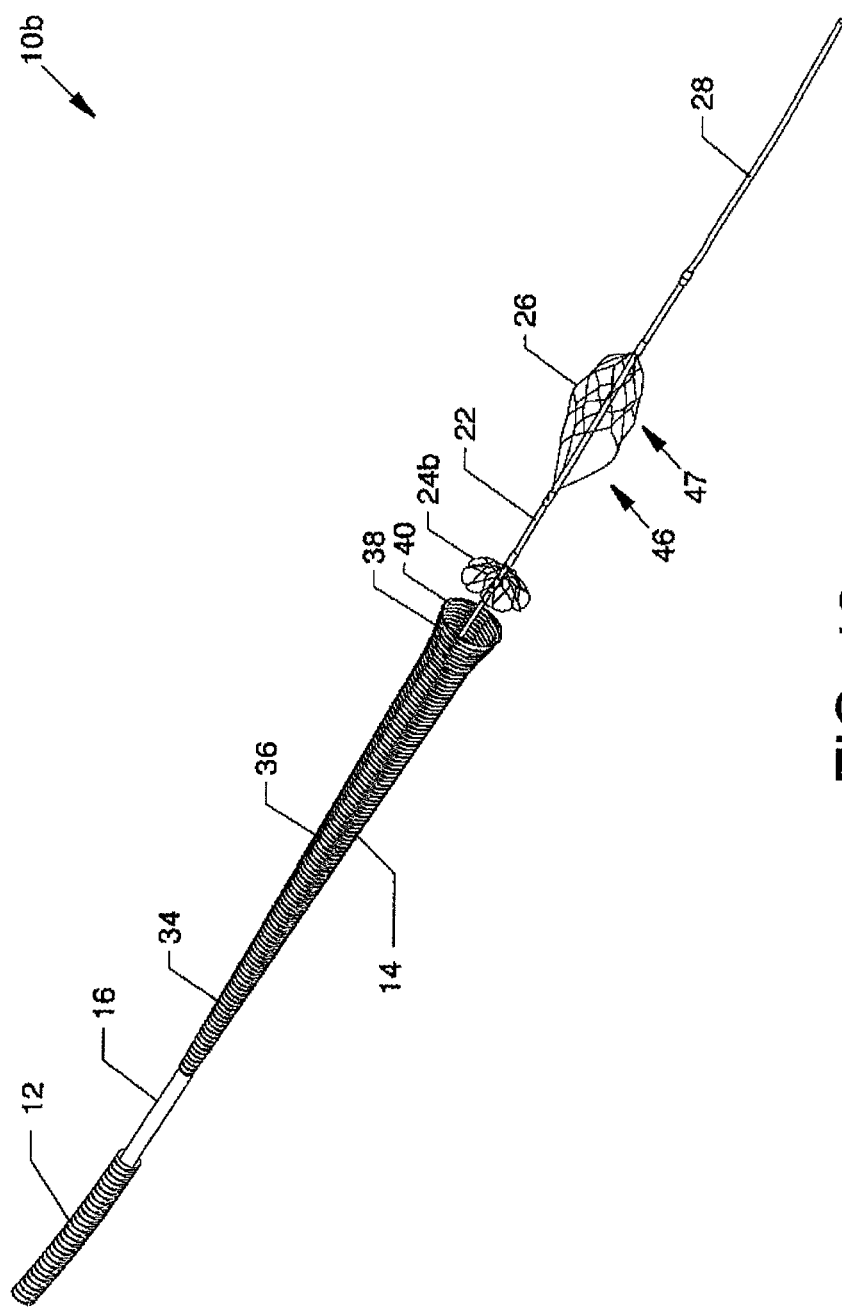
FIG. 19 is an illustration similar to FIG. 2 and is an isometric view of the guidewire filter components located at the distal region of a second alternative embodiment.

FIG. 19 is an illustration similar to FIG. 2 and is an isometric view of the components located at the distal region of this second alternative embodiment of the present disclosure. Shown in particular is the relationship of the proximal filter 24b to the capture sleeve 14 and to the distal filter 26.

Figure 20:
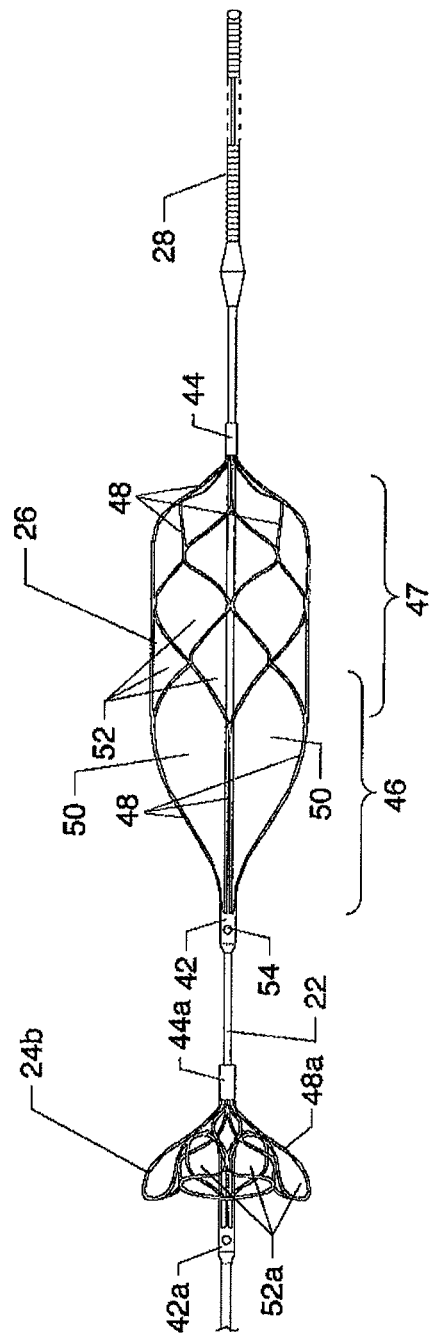
FIG. 20 is a full view illustration corresponding to FIG. 4 and is a side view of the distal end of the guidewire including the preformed memory shaped proximal filter and the preformed memory shaped distal filter.

FIG. 20 is a full view illustration corresponding to FIG. 4 and is a side view of the distal end of the guidewire 22 including the preformed memory shaped proximal filter 24b and the preformed memory shaped distal filter 26. The structure of the proximal filter 24b is related to that of the distal filter 26 but does not include large openings 50. Features of the proximal filter 24b include strands 48a which form small openings 52a corresponding for the most part to the small openings 52 of the distal filter 26 which openings are arranged and located between the proximal tube 42a and the distal tube 44a. The proximal tube 42a secures over and about the guidewire 22 in the same fashion as prescribed for the attachment of the proximal tube 42 of the preferred embodiment. The distal tube 44a is aligned over and about the guidewire 22 and is slidingly engaged therewith. The use of the fixed proximal tube 42a and the slideable distal tube 44a enables the proximal filter 24b to be flexibly and expandingly deployed and to be flexibly, compressingly, reversibly and elongatingly collapsed along and about the guidewire 22 whereby a lower filter profile is provided in order to facilitate removal.

Mode of Operation

The mode of operation of this second alternative embodiment of the intravascular guidewire filter system 10b for the filtering and removal of various sized pieces of organized embolic debris is now described with reference to FIGS. 21-25, as well as understood reference to previously described figures. Operation of the capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached proximal filter 24b and distal filter 26 as required during various delivery and capture phases, such as previously described with reference to the preferred embodiment.

Engagement and entrapment of smaller pieces of the embolic debris 76 in the distal filter 26 can be accomplished by the distal blood flow containing smaller pieces of embolic debris 76, as previously described. Engagement and entrapment of large embolic debris 76 can be accomplished by the judicious placement of the proximal filter 24b and the distal filter 26 with respect to the large embolic debris 76. With respect to the large embolic debris 76, the guidewire 22 is deployed to position the proximal filter 24b distal to a large piece of embolic debris 76, as shown in FIG. 21 and used as described herein.

Figure 21:
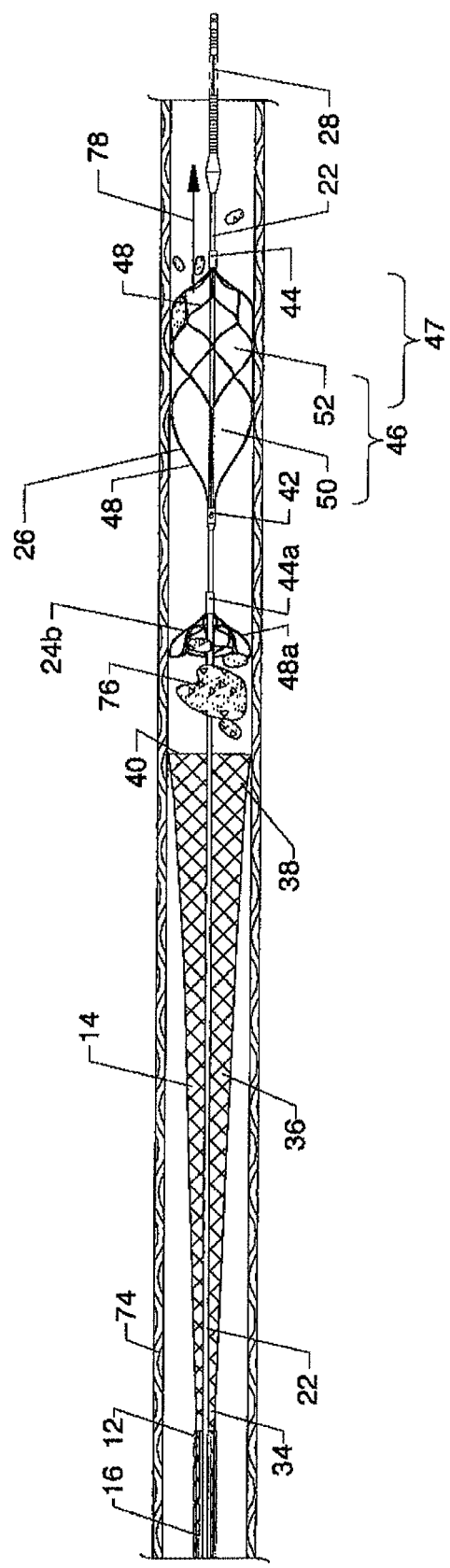
FIG. 21 is a cutaway view shown in partial cross section and partial cutaway view in the capture mode of the second alternative embodiment showing the proximal filter (in cutaway view), the distal filter and the guidewire deployed and aligned within a blood vessel.

As shown in FIG. 21 and with respect to this second alternative embodiment, a cutaway view is shown in partial cross section and partial cutaway view in the capture mode showing the proximal filter 24b (in cutaway view), the distal filter 26 and the guidewire 22 deployed and aligned within a blood vessel 74 showing a large piece of embolic debris 76 located proximal to the proximal filter 24b prior to an initial engagement of the filters by the flared distal section 38 of the capture sleeve 14. The capture sleeve 14 which has been expandingly deployed in the blood vessel 74, as previously described in the preferred embodiment, is shown immediately proximal to the proximal filter 24b and a short distance from the distal filter 26. Manual positioning of the guidewire 22 in a proximal direction causes the deployed proximal filter 24b to engage and urge the large piece of embolic debris 76 proximally to enter into the flared distal section 38 of the capture sleeve 14, the latter of which may be urged distally to cooperatingly accommodate the large piece of embolic debris 76. The large piece of embolic debris 76 encounters the filtering weave of the strands 48a located in the proximal filter 24b which weave initially and wholly engages the large piece of embolic debris 76 with minimum, if any, parting, dividing or macerating thereof. Also shown in the illustration is embolic debris 76 of smaller size which had not been engaged by the proximal filter 24b but which is engaged in the distally located filter end 47 of the distal filter 26.

Figure 22:
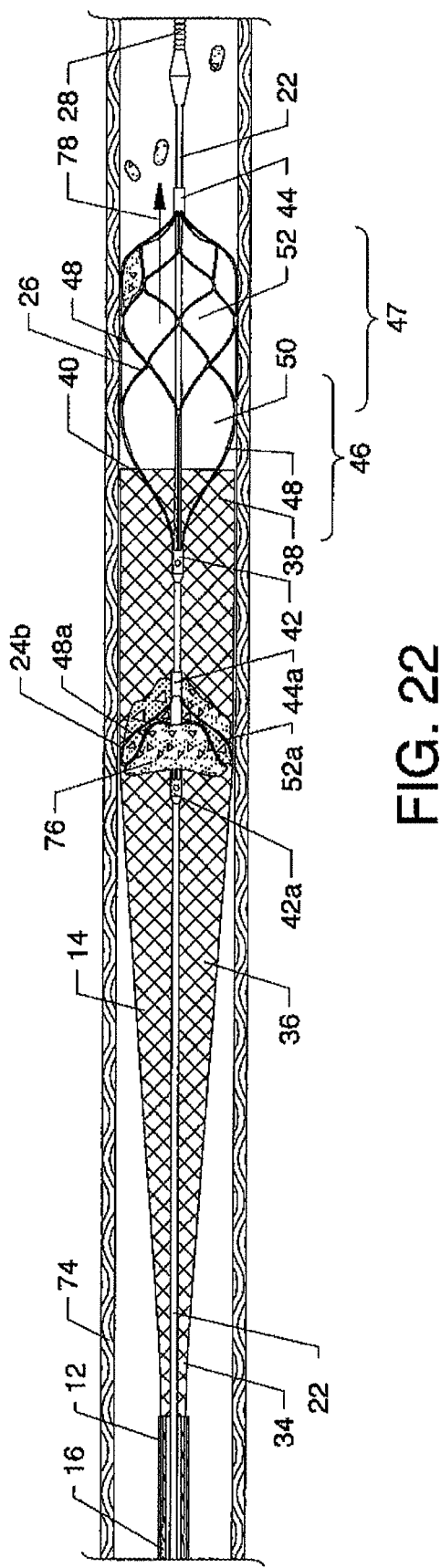
FIG. 22 is an illustration similar to FIG. 21 further showing the capture mode and demonstrating the engagement of the uncompressed capture sleeve over and about the proximal filter, over and about the proximal end of the distal filter, and over and about a large piece of embolic debris.

FIG. 22 is an illustration similar to FIG. 21 further showing the capture mode and demonstrating the engagement of the uncompressed capture sleeve 14 over and about the proximal filter 24b, over and about the proximal end of the distal filter 26 and over and about the large piece of embolic debris 76, the latter of which has been urged into the interior of the capture sleeve 14 and engaged therein by action of the proximally directed guidewire 22 and proximal filter 24b. Such engagement may be assistingly accomplished by advancing the capture sleeve 14 distally toward and over the proximal filter 24b and the distal filter 26 by operation of the capture sleeve operator 20 in order to position the flared distal section 38 and the annular edge 40 of the captive sleeve 14 in close proximity to the proximal filter 24b and the large piece of embolic debris 76, as shown in FIG. 21. The guidewire 22 is then actuated proximally in order to intimately contact, pull and urge the large piece of embolic debris 76 into the capture sleeve 14 as shown by the impingement of the large piece of embolic debris 76 by the proximally directed proximal filter 24b through the flared distal section 38 and the annular edge 40 of the capture sleeve 14 and into the flared midsection 36, i.e., the confines of the capture sleeve 14. During such proximally directed urging of the large piece of embolic debris 76, it can progressively impinge upon the flared distal section 38 and the flared midsection 36 of the capture sleeve 14 where the reduction of the flare of each section beneficially resists proximal movement of the impinging large piece of embolic debris 76. Such impingement and resistance to movement temporarily and wedgingly fixes the position of the large piece of embolic debris 76, whereby the proximally urged strands 48a of the proximally directed proximal filter 24b can then forcibly part, divide and macerate the large piece of embolic debris 76, as now shown in FIG. 22, resulting in several smaller pieces as shown in FIG. 23.

Figure 23:
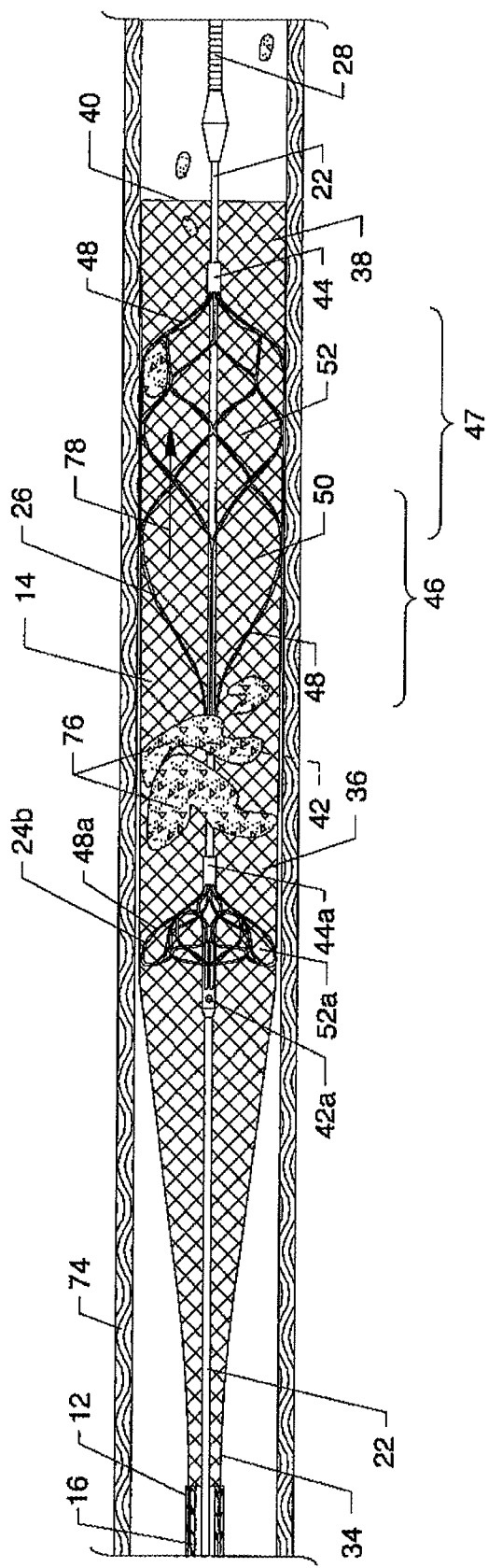
FIG. 23 is an illustration similar to FIG. 22 further showing the capture mode and demonstrating the full engagement of the uncompressed capture sleeve over and about the proximal filter, the distal filter and pieces of the large piece of embolic debris.
Figure 24:
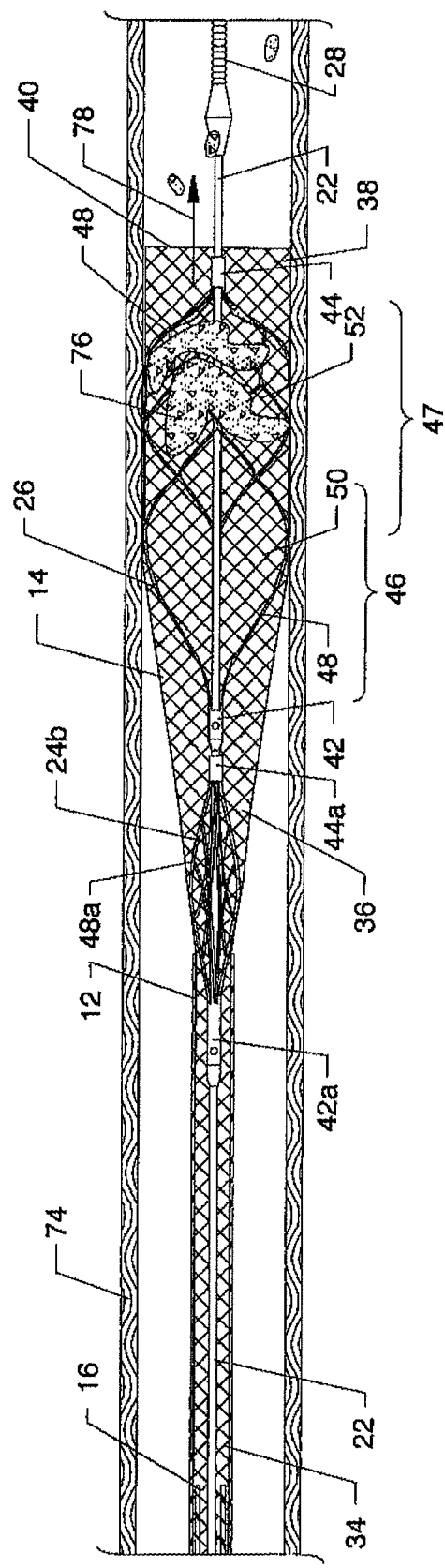
FIG. 24 is an illustration similar to FIG. 23 but where the distal filter is shown in cross section view further showing the capture mode and demonstrating the distal positioning of the capture/delivery sheath over and about capture sleeve.

FIG. 23 is an illustration similar to FIG. 22 further showing the capture mode and demonstrating full engagement of the uncompressed capture sleeve 14 over and about the proximal filter 24b, the distal filter 26 and pieces of the large piece of embolic debris 76, the latter of which have been forcibly parted, divided and macerated by passage through the strands 48a of the proximal filter 24b and subsequently contained in the interior of the capture sleeve 14. These smaller pieces of embolic debris 76 can be urged distally by blood flow or by proximal movement of the distal filter 26 to impinge upon or be impinged by the strands 48 of the large openings 50 to enter the large openings 50 of the distal filter 26. Subsequent trapping of such processed embolic debris 76 is provided by the strands 48 comprising the small openings 52 at the distally located filter end 47 of the distal filter 26, as shown in FIG. 24. Very small particles of embolic debris 76, which pass through the distally located filter end 47 of the distal filter 26, may be of insignificant consequence and can pass downstream.

FIG. 24 is an illustration similar to FIG. 23, but where the distal filter 26 is shown in cross section view further showing the capture mode and demonstrating the distal positioning of the capture/delivery sheath 12 further over and about the capture sleeve 14 in order to compress the flared midsection 36 of the capture sleeve 14 and to compress the underlying coaxially aligned proximal filter 24b. The positioning of the distal end of the capture/delivery sheath 12 over and about the proximal tube 42a and the proximal portion of the strands 48a causes the concave feature of the proximal filter 24a to refonningly elongate. The parted, divided and macerated embolic debris 76 is shown entrapped within the filter end 47 of the distal filter 26.

Figure 25:
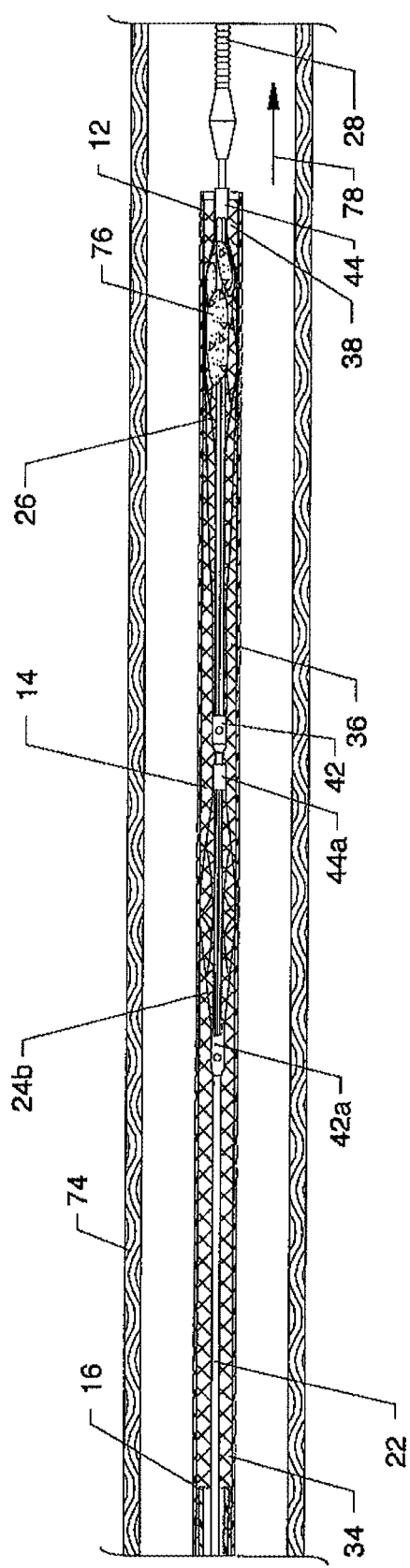
FIG. 25 is an illustration of the second alternative embodiment showing and demonstrating the use of the capture/delivery sheath in the full capture mode.

FIG. 25 is an illustration showing and demonstrating the use of the capture/delivery sheath 12 in a full capture mode. More specifically, collapsing of the proximal filter 24b and distal filter 26 is assisted by the full compressed engagement of the capture sleeve 14, full compressed engagement of the capture/delivery sheath 12, or both, in a manner as previously described in detail. In this illustration, the capture/delivery sheath 12 is directly and compressingly positioned over and about the entire capture sleeve 14 in order to provide complete compression thereof. Furthermore, the capture/delivery sheath 12 is indirectly and compressingly positioned over and about the coaxially aligned proximal filter 24b and any embolic debris 76 captured therein, indirectly and is compressingly positioned over and about the distal filter 26 and any embolic debris 76 captured therein in order to provide a compressed low profile structure of such components containing captured large or small embolic debris 76. Such a low profile structure of such components containing captured embolic debris 76 may be readily withdrawn, preferably in a manner and fashion as previously described with respect to the preferred embodiment.

Figure 26:
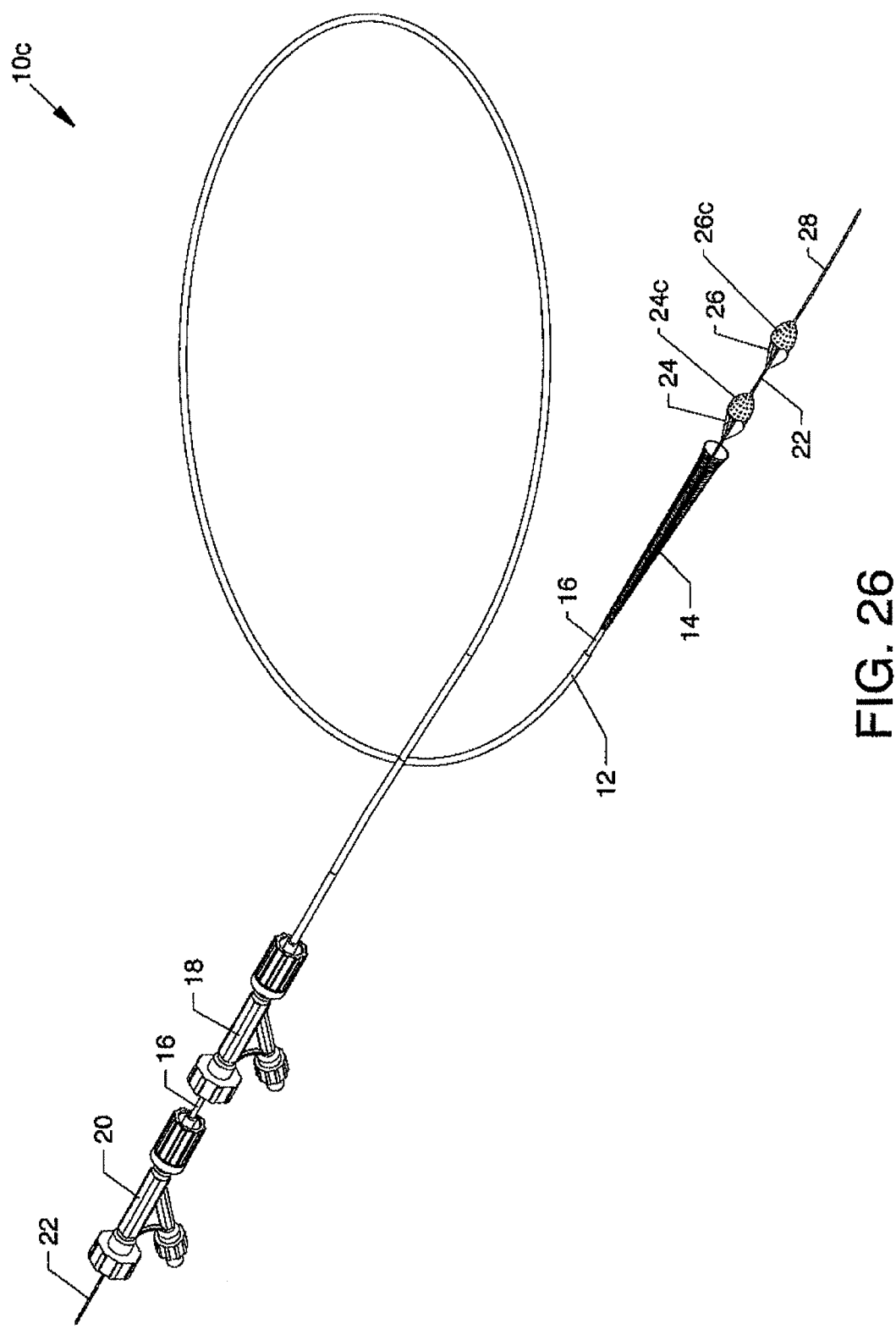
FIG. 26, a third alternative embodiment, is an isometric overview of the intravascular emboli capture and retrieval system for intravascular embolism protection and embolism removal or maceration.
Figure 27:
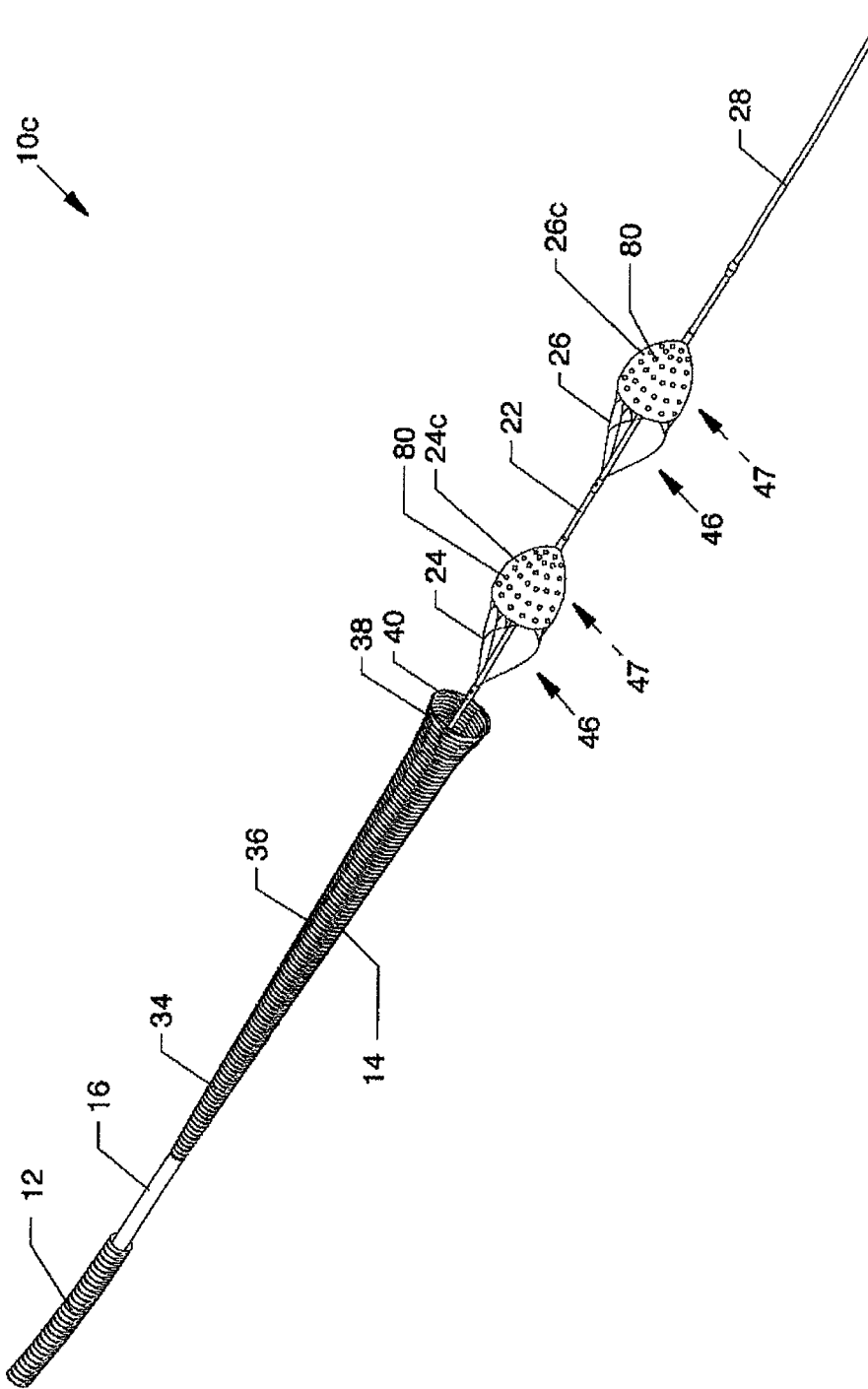
FIG. 27 is an illustration similar to FIG. 2 and is an isometric view of the guidewire filter components located at the distal region of a third alternative embodiment.

FIG. 26, a third alternative embodiment, is an isometric overview of the intravascular emboli capture and retrieval system for intravascular embolism protection and embolism removal or maceration, 10c. Generally, this alternative embodiment is useful in blood vessels of 8 mm or less to capture embolic debris, although maceration of such debris is also associated therewith and is used in much the same manner as described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This third alternative embodiment is similar to the preferred embodiment of FIG. 1 with the exception of the addition, arrangement, reorientation or modification of one or more filters and use thereof. As shown in FIG. 27, similarly constructed flexible proximal and distal fine filters 24c and 26c having a plurality of small orifices 80 and having generally the same shape and profile as the filter ends 47 are aligned and attached over and about filter ends 47 of the proximal filter 24 and the distal filter 26, respectively, in order to provide for a fine filtration and in order to allow for blood passage therethrough. Preferably, the proximal and distal fine filters 24c and 26c include a preformed memory shape.

FIG. 27 is an illustration similar to FIG. 2 and is an isometric view of the components located at the distal region of this third alternative embodiment of the present disclosure. Shown in particular is the addition of proximal and distal fine filters 24c and 26c over and about filter ends 47 of the proximal filter 24 and the distal filter 26.

Figure 28:
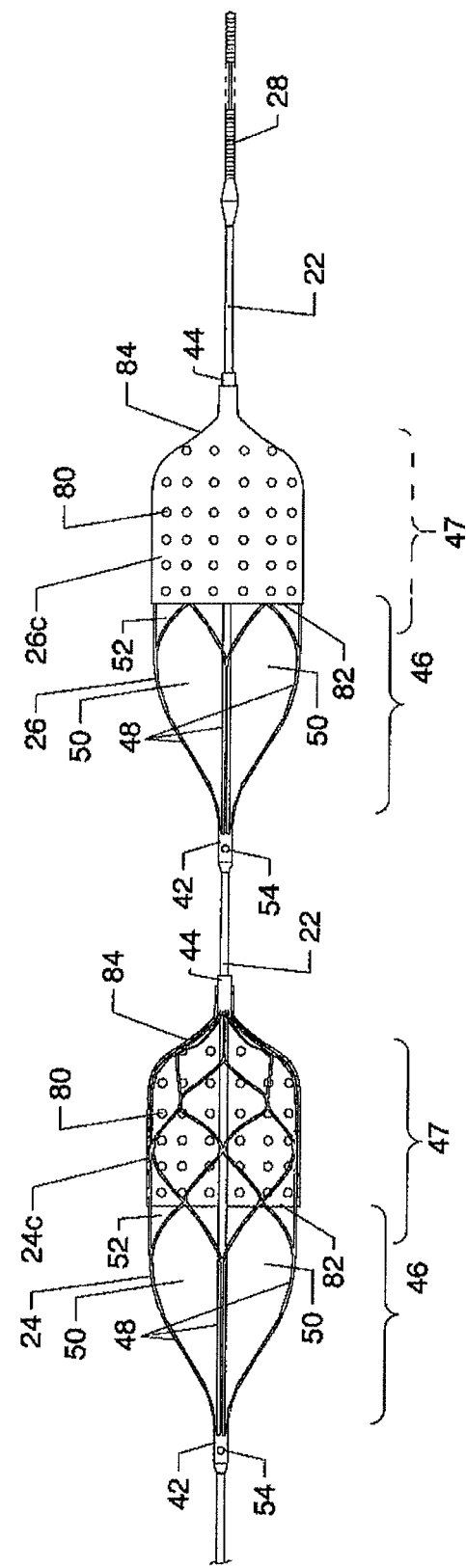
FIG. 28 is an illustration similar to FIG. 4 and is a side view of the distal end of the guidewire including the preformed memory shaped proximal filter, a preformed memory shaped distal filter and an overlying preformed memory shaped proximal fine filter and an overlying preformed memory shaped distal fine filter, respectively.
Figure 29:
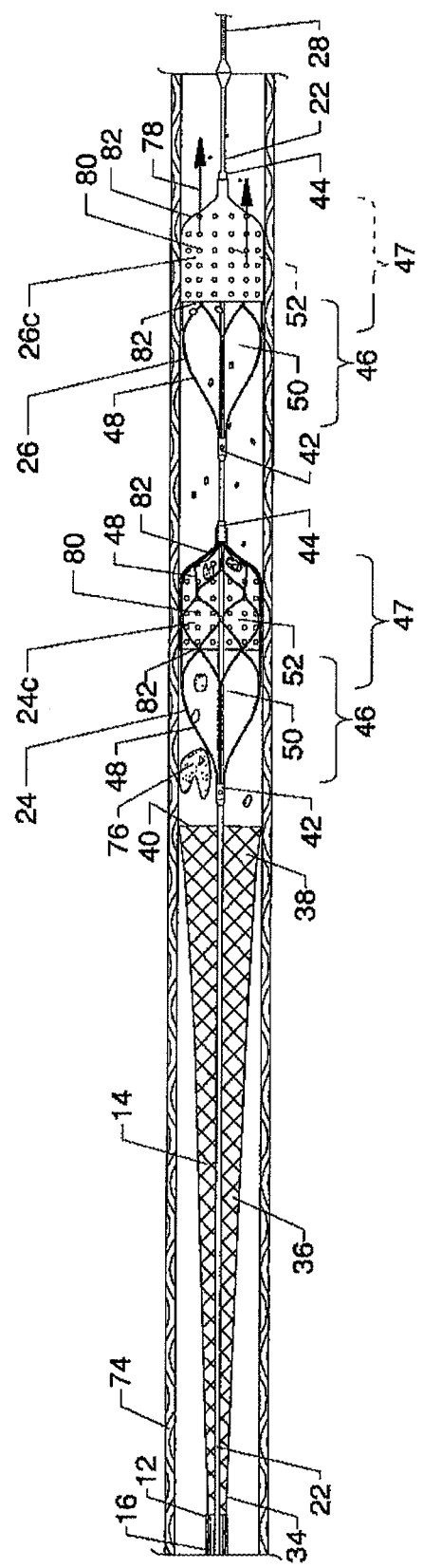
FIG. 29 is a cutaway view in partial cross section and partial cutaway view in the capture mode of the third alternative embodiment showing the proximal filter, the proximal fine filter (in cutaway view) overlying the proximal filter, the distal filter and the distal fine filter overlying the distal filter and the guidewire deployed and aligned within a blood vessel.
Figure 30:
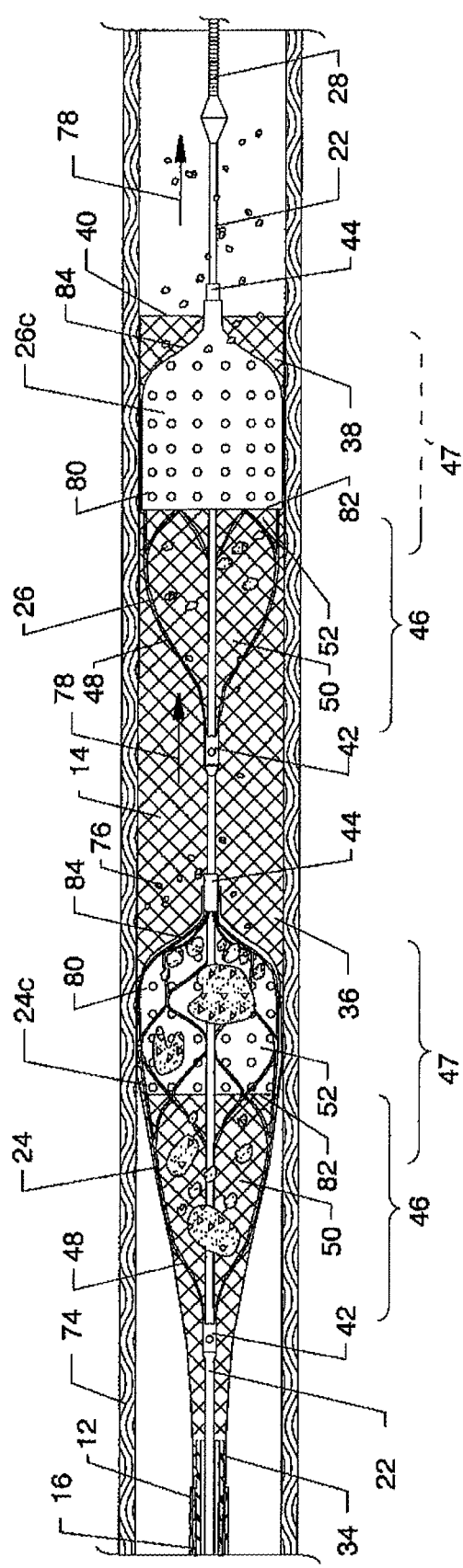
FIG. 30 is an illustration further showing the capture mode and demonstrating the full engagement of the uncompressed capture sleeve over and about the proximal filter, the overlying proximal fine filter, the distal filter, the overlying distal fine filter pieces of embolic debris and the guidewire.

FIG. 28 is an illustration similar to FIG. 4 and is a side view of the distal end of the guidewire 22 including the preformed memory shaped proximal 10 filter 24, the preformed memory shaped distal filter 26 and the overlying preformed memory shaped proximal fine filter 24c and overlying preformed memory shaped distal fine filter 26c, respectively. The shape of the proximal fine filter 24c and distal fine filter 26c resembles a short tube having an open proximal end 82 and a tapered distal end 84 where the proximal fine filter 24c and the distal fine filter 26c end. 15 Each fine filter includes a plurality of small filter orifices 80 distributed along and about the structure thereof whereby each fine filter allows for blood and small and insignificantly sized particles of embolic debris 76 to pass therethrough but traps larger pieces of embolic debris 76. The taper of the tapered distal ends 84 decreases to a suitable size in order to be secured over and about the distal tubes 44 and which 20 tapered distal ends 84 are attached to the distal tubes 44 at the ends of the proximal filter 24 and the distal filter 26. The bodies and the open proximal end 82 of the proximal fine filter 24c and distal fine filter 26c are not directly secured to the proximal filter 24 and distal filter 26 but maintain a close intimate relationship to the shape of the filter ends 47 whereby both fine filters can expand generally to the same 25 diameter size and shape as the filter ends. In FIGS. 28-30, proximal fine filter 24c is shown in cutaway view as an example to fully demonstrate its relation to proximal filter 24. The use of the fixed proximal tube 42 and the slideable distal tube 44 enables the proximal filter 24 and the distal filter 26 with the overlying attached proximal fine filter 24c and overlying attached distal fine filter 26c, respectively, to be flexibly and expandingly deployed and to be flexibly, compres singly, and elongatingly collapsed along and about the guidewire 22 whereby, in the latter condition, a lower filter profile is provided in order to facilitate their removal.

Mode of Operation

The mode of operation of the third alternative embodiment of the intravascular guidewire filter system 10c for the filtering and removal of various sized pieces of organized embolic debris is now described with reference to FIGS. 29-32, as well as understood reference to previously described figures to provide for fine filtration and to allow for blood passage therethrough. Operation of 10 the capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached proximal filter 24, the overlying proximal fine filter 24c, the distal filter 26 and the overlying distal fine 15 filter 26c as required during various delivery and capture phases, such as previously described with reference to the preferred embodiment.

Engagement and entrapment of various pieces of the embolic debris 76, as previously described, with further and more complete fine filtration of embolic debris 76 is provided by this third alternative embodiment. Engagement and 20 entrapment of embolic debris 76 of various sizes can be accomplished by the judicious placement of the proximal filter 24 and the overlying proximal fine filter 24c and the distal filter 26 and the overlying proximal fine filter 24c. The guidewire 22 is deployed to position the proximal filter 24 and the overlying proximal fine filter 24c distal to or at a location where fine filtration is desired and then used as 25 described herein. Distal blood flow containing various sized pieces of embolic debris 76 are first encountered by the strands 48 of the large openings 50 of the proximal filter 24 to be forcibly parted, divided and macerated as previously described and thence are further urged into the combined closely associated filter end 47 and its overlying more restrictive proximal fine filter 24c. The size of the small filter orifices 80 is smaller than that of the underlying small openings 52 and therefore provides for better and more complete fine filtration than that filtration provided by the small openings 52.

As shown in FIG. 29 and with respect to this third alternate embodiment, a cutaway view is shown in partial cross section and partial cutaway view in the capture mode, the proximal filter 24, the proximal fine filter 24c (in cutaway view) overlying the proximal filter 24, the distal filter 26 and the distal fine filter 26c overlying the distal filter 26 and the guidewire 22 are deployed and aligned within a blood vessel 74 having various sized pieces of embolic debris 76 therein and located proximal and distal to the proximal filter 24 and proximal fine filter 24c. This illustration also shows the position of the flared distal section 38 of the capture sleeve 14 prior to its initial engagement with the proximal and distal filters. The capture sleeve 14, which has been expandingly deployed in the blood vessel 74 as previously described in the preferred embodiment, is shown immediately proximal to the proximal filter 24 and overlying the proximal fine filter 24c and a short distance from the distal filter 26 and overlying the distal fine filter 26c.

FIG. 30 is an illustration further showing the capture mode and demonstrating the full engagement of the uncompressed capture sleeve 14 over and about the proximal filter 24, the overlying proximal fine filter 24c, the distal filter 26, the overlying the distal fine filter 26c and pieces of embolic debris 76 some of which have been forcibly parted, divided and macerated by passage through the strands 48 of the proximal filter 24, entered through the large openings 50 and which have been captured within the proximal filter 24 and overlying the proximal fine filter 24c, as well as engagement over and about some particles of embolic debris 76 which are contained in or which are transiting the interior of the capture sleeve 14 to be further captured by the distal filter 26 and overlying distal fine filter 26c. Such engagement of the uncompressed capture sleeve 14 over and about the proximal filter 24, the overlying proximal fine filter 24c, the distal filter 26, the overlying distal fine filter 26c and pieces of embolic debris 76 may be accomplished by first advancing the capture sleeve 14 distally toward and over the proximal filter 24 and the overlying proximal fine filter 24c, the distal filter 26, and the overlying distal fine filter 26c by operation of the capture sleeve operator 20 in order to first position the flared distal section 38 and the annular edge 40 of the capture sleeve 14 in close proximity to the proximal filter 24 and overlying the proximal fine filter 24c and the pieces of embolic debris 76, such as shown in FIG. 29. The guidewire 22 can be cooperatively actuated proximally in order to urge any large pieces of embolic debris 76 into the capture sleeve 14 by impingement of the embolic debris 76 with the proximally directed proximal filter 24, thereby providing for an embolic debris entry through the flared distal section 38 and the annular edge 40 of the capture sleeve 14 and into the flared midsection 36, i.e., into the confines of the capture sleeve 14 and thence by the action of forcibly parting, dividing and maceration into the proximal filter 24 and the proximal fine filter 24c. Subsequent trapping of such processed embolic debris 76 can be provided by the distal filter 26 and the distal fine filter 26c the latter of which could include filter orifices 80 with a small radius. Very small fine particles of embolic debris 76 which pass through the proximal filter 24, the proximal fine filter 24c, the distal filter 26 and the distal fine filter 26c may be of insignificant consequence and can pass downstream.

Figure 31:
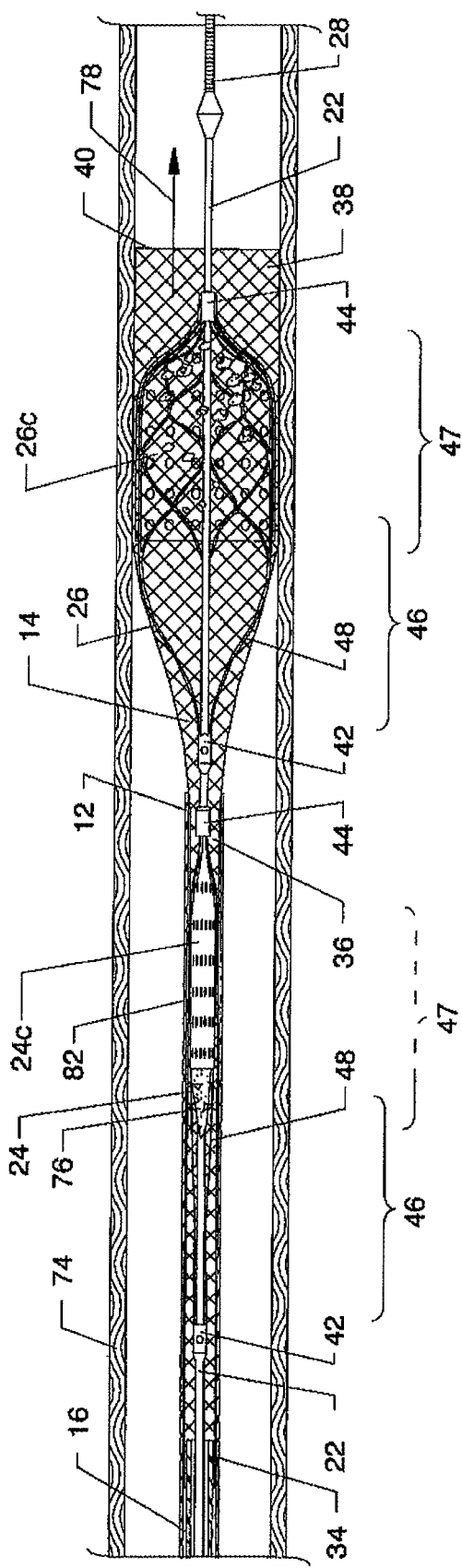
FIG. 31 is an illustration similar to FIG. 30 but where the distal filter and distal fine filter are shown in cross section view and where the proximal filter and proximal fine filter are shown in full view further showing the capture mode.

FIG. 31 is an illustration similar to FIG. 30, but where the distal filter 26 and distal fine filter 26c are shown in cross section view and where the proximal filter 24 and proximal fine filter 24c are shown in full view further showing the capture mode and demonstrating the distal positioning of the capture/delivery sheath 12 further over and about the capture sleeve 14 in order to compress the flared midsection 36 of the capture sleeve 14 and in order to compress the underlying coaxially aligned proximal filter 24 and underlying proximal fine filter 24c. Parted, divided and macerated embolic debris 76 is shown engaging the filter end 47 of the distal filter 26. The parted, divided and macerated embolic debris 76 is shown extending from the confines of the proximal fine filter 24c and the proximal filter 24 and extending into the open end 46 of the proximal filter 24.

Figure 32:
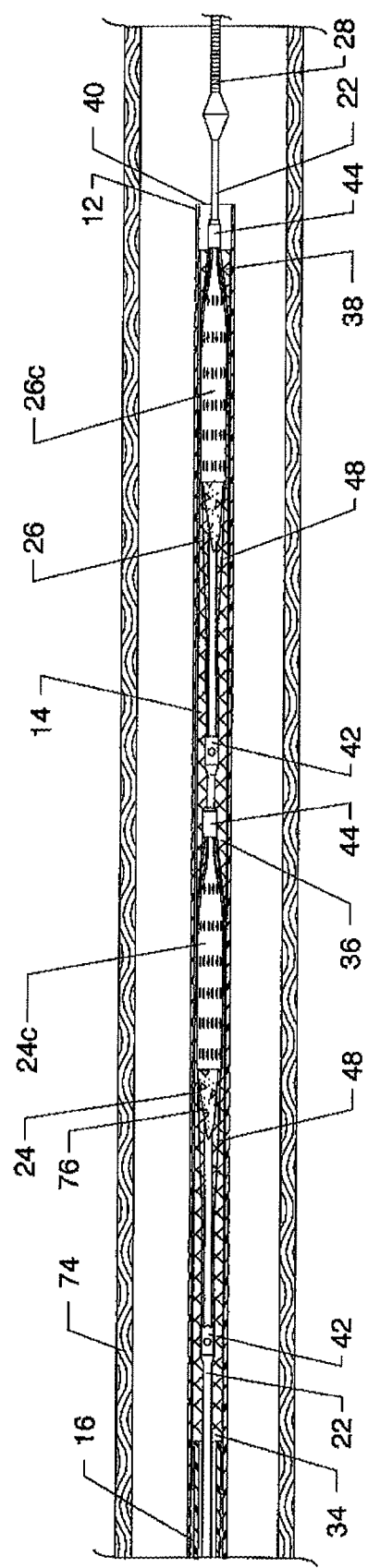
FIG. 32 is an illustration showing and demonstrating the use of the capture/delivery sheath in the full capture mode.

FIG. 32 is an illustration showing and demonstrating the use of the capture/delivery sheath 12 in the full capture mode. More specifically, collapsing of the proximal filter 24 and the underlying proximal fine filter 24c and distal filter 26 and the underlying distal fine filter 26c is assisted by the full compressed engagement 5 of the capture sleeve 14, full compressed engagement of the capture/delivery sheath 12, or both, in a manner as previously described in detail. In this illustration, the capture/delivery sheath 12 is directly and compressingly positioned over and about the capture sleeve 14 in order to provide for the complete compression of the capture sleeve 14 and is indirectly and compressingly positioned over and about the 10 coaxially aligned proximal filter 24 and the underlying proximal fine filter 24c, indirectly and compressingly positioned over and about the distal filter 26 and the distal fine filter 26c and any embolic debris 76 captured therein resulting in a compressed low profile structure of such components containing captured large or small embolic debris 76. Such a low profile structure of such components containing 15 captured embolic debris 76 may be readily withdrawn, preferably in a manner and fashion as previously described with respect to the preferred embodiment. In the alternative to the proximal fine filter 24c and the distal fine filter 26d, the filter ends 47 could be of a very fine weave which would allow the capture of very small particles of embolic debris but which would still allow passage of a sufficient amount 20 of blood flow therethrough.

Figure 33:
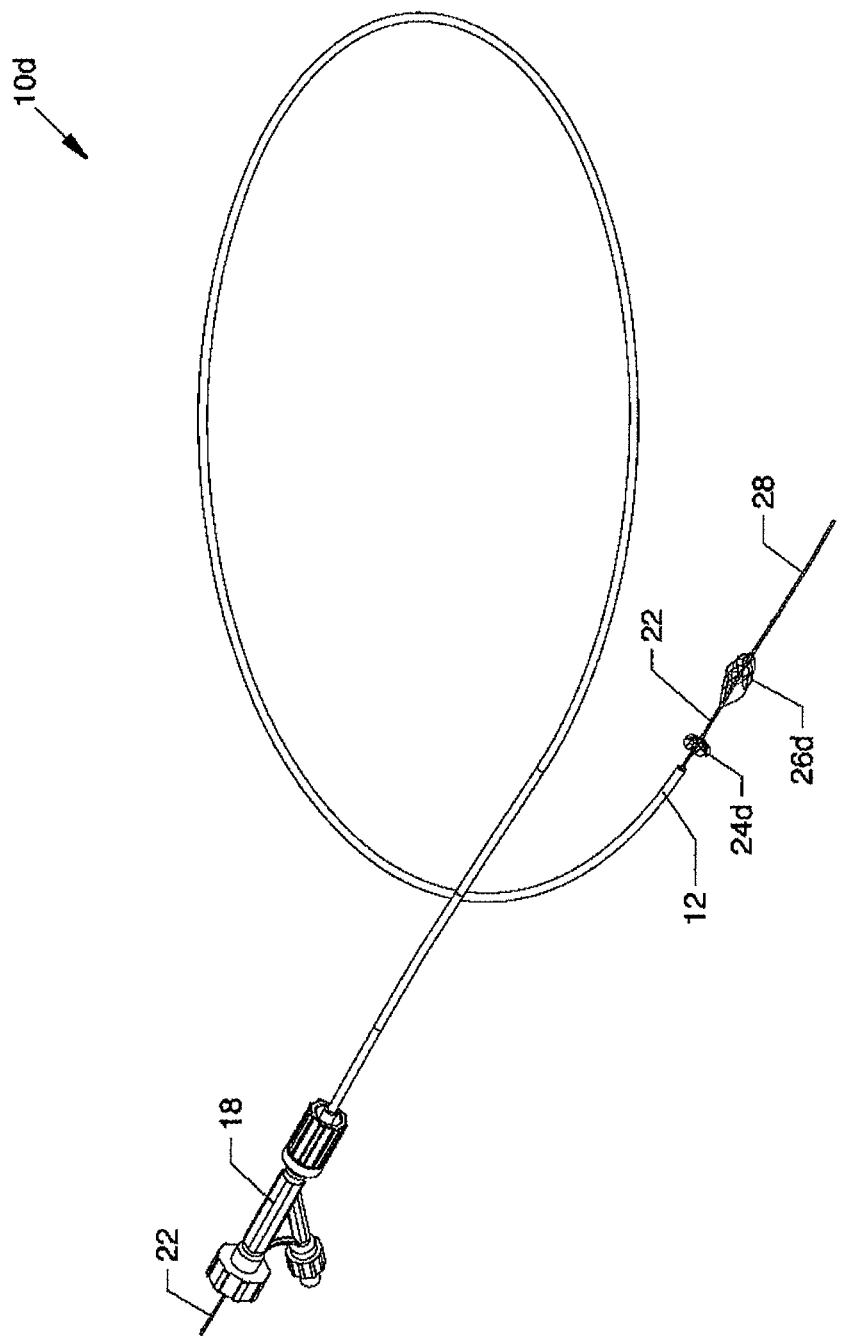
FIG. 33, a fourth alternative embodiment, resembles the second alternative embodiment and is an isometric illustration of the intravascular emboli capture and retrieval system for intravascular embolism protection and embolism removal or maceration.

FIG. 33 is a fourth alternative embodiment that resembles the second alternative embodiment and is an isometric illustration of the intravascular emboli capture and retrieval system for intravascular embolism protection and embolism removal or maceration, 10d. Generally, this alternative embodiment is 25 useful in blood vessels of 18 mm to 34 mm to part, divide and macerate large embolic debris or the removal of embolic debris 76 such as may be used by an AngioJet® thrombectomy device and catheter and does not include a capture sleeve 14, a capture sleeve operator 20 or a capture sleeve positioning tube 16 such as used and shown in the previous embodiments. Many components are constructed in a fashion similar to the preceding embodiments but are of an increased size in order to be used in femoral or other larger vessels. The proximal filter 24d is constructed using the same structure, principles and teachings of the proximal filter 24b but can be sized from 18 mm to 34 mm and the distal filter 26d is constructed using the same structure, principles and teachings of the distal filter 26 but can be sized from 18 mm to 34 mm. For purposes of example and demonstration, the capture/delivery sheath 12 can be sized at 3 mm. As can be appreciated by those of skill in the art, two or more preformed memory shaped filters can be utilized in configurations consistent with the scope of the present disclosure.

Figure 34:
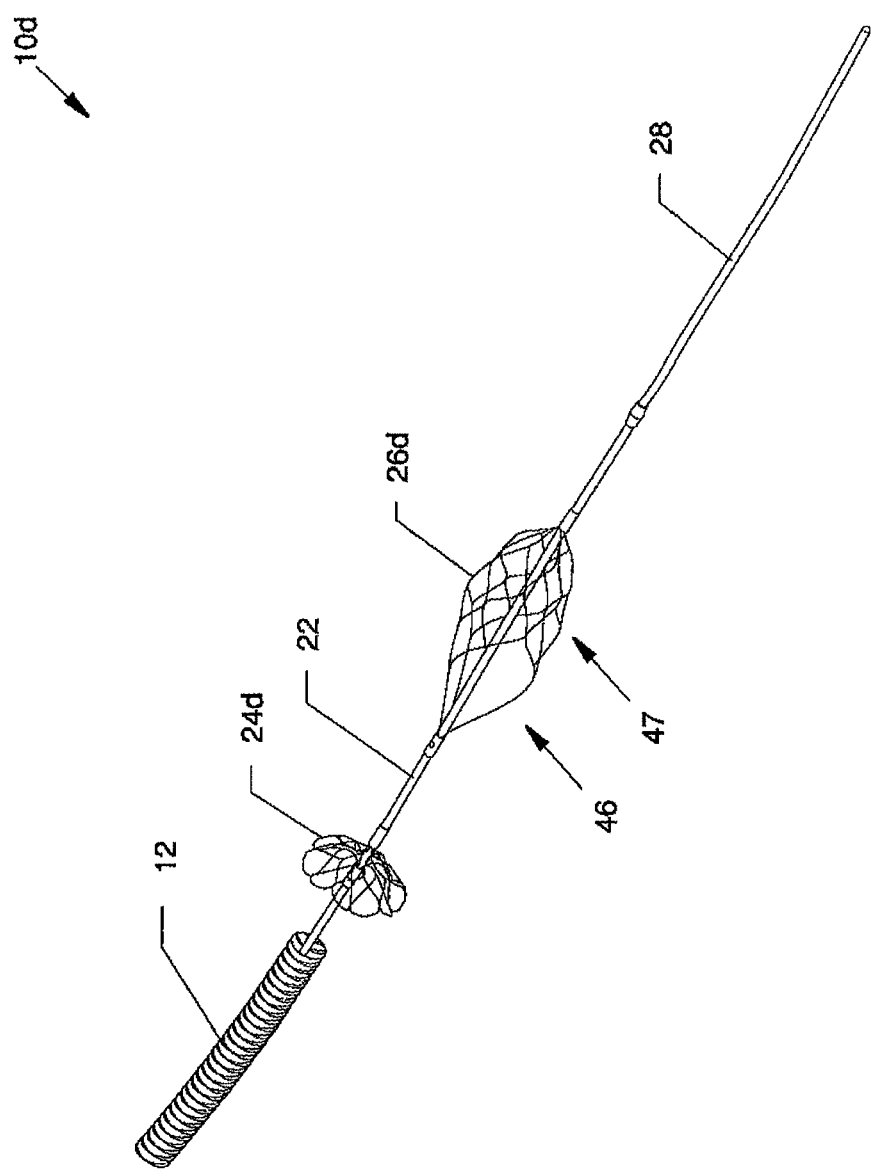
FIG. 34 is an illustration similar to FIG. 2 and is an isometric view of the components located at the distal region of this fourth alternative embodiment.

FIG. 34 is an illustration similar to FIG. 2 and is an isometric view of the components located at the distal region of this fourth alternative embodiment of the disclosure. Shown in particular is the relationship of the proximal filter 24d and the distal filter 26d to each other and to the distal end of the capture/delivery sheath 12.

Mode of Operation

The mode of operation includes expandingly deploying the proximal filter 24d and the distal filter 26d through and distal to a large embolic debris 76 and then using one or more operational modes. One mode is used to remove embolic debris 76 by the use of an AngioJet® thrombectomy device and catheter and another mode is used to part, divide and macerate the large embolic debris 76 into smaller manageable pieces. The modes of operation of this fourth alternative embodiment of the intravascular guidewire filter system 10d for the filtering and removal of various sized pieces of organized embolic debris is now described with reference to FIGS. 35 and 36, as well as understood reference to previously described figures. A larger sheath, as known in the art, is used to insert the flexible guidewire 22 and the proximal filter 24d and the distal filter 26d into the vasculature. Operation of the capture/delivery sheath operator 18 positions the capture/delivery sheath 12 in cooperating operation with the flexible guidewire 22 and the attached proximal filter 24d and distal filter 26d, as required. Engagement and treatment of large embolic debris 76 can be accomplished by the judicious placement of the proximal filter 24d and the distal filter 26d with respect to the large embolic debris 76.

Figure 35:
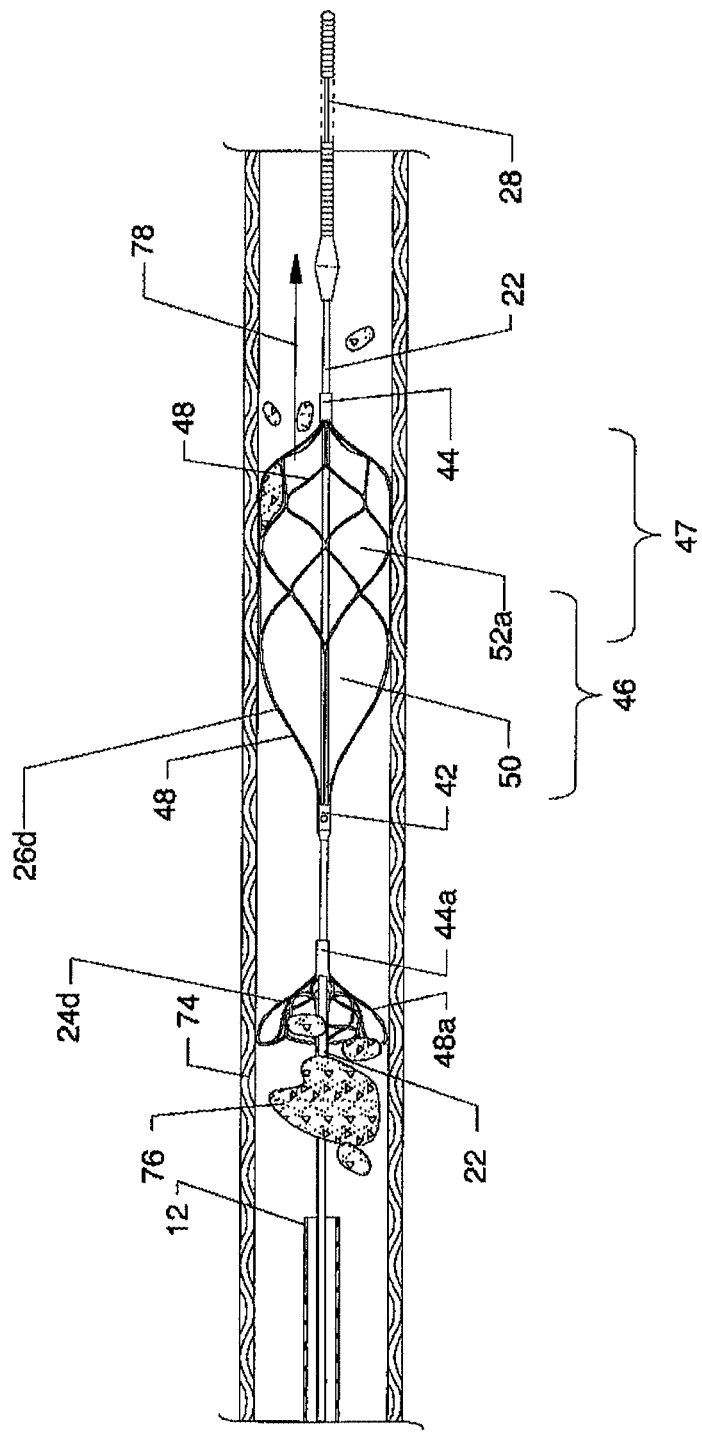
FIG. 35 is a cutaway view shown in partial cross section and partial cutaway view in the capture mode showing the proximal filter (in cutaway view), the distal filter, and the guidewire deployed and aligned in a blood vessel.

As shown in FIG. 35 and with respect to this fourth alternative embodiment, a cutaway view is shown in partial cross section and partial cutaway view in the capture mode showing the proximal filter 24d (in cutaway view), the distal filter 26d, and the guidewire 22 deployed and aligned in a blood vessel 74 and further showing a large piece of embolic debris 76 engaging the proximal filter 24d. The large piece of embolic debris 76 encounters the filtering weave of the strands 48a located on the proximal filter 24d which initially and wholly engages the large piece of embolic debris 76 with minimum, if any, parting, dividing or macerating. The capture/delivery sheath 12 can be retracted and then removed from about the guidewire 22 and an AngioJet® thrombectomy device and catheter can be engaged over and about the guidewire 22 and utilized to macerate and remove the embolic debris 76 which is in intimate contact with the proximal filter 24d.

Figure 36:
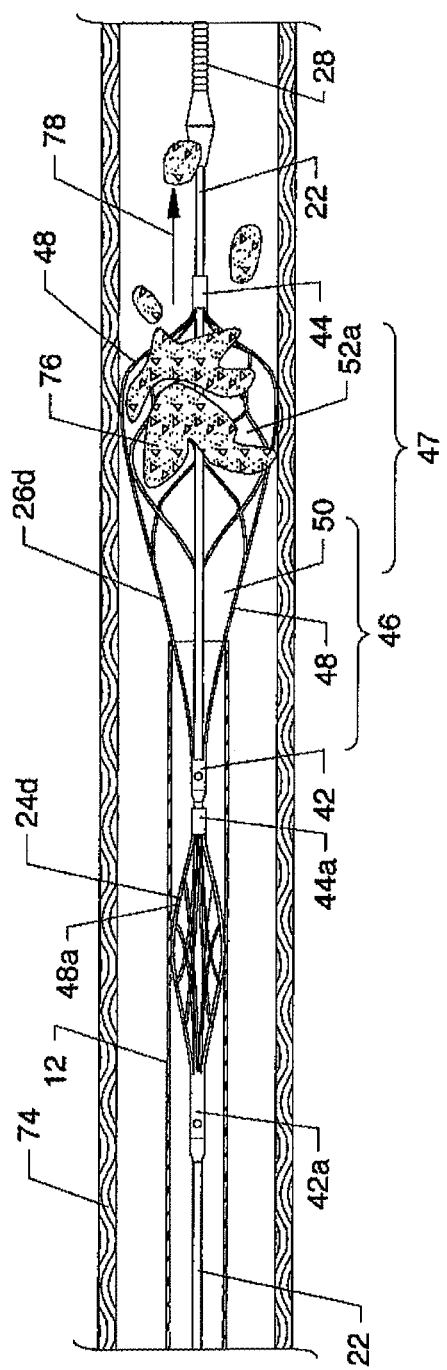
FIG. 36 is an illustration showing yet another operational mode but where the distal filter is shown in cross section view further showing the capture mode and demonstrating the full compression of the proximal filter.

FIG. 36 is an illustration showing yet another operational mode of the fourth alternative embodiment, but where the distal filter 26d is shown in cross section view and further showing the capture mode and demonstrating the full compression of the proximal filter 24d which is shown having been positioned proximally to be contained within the capture/delivery sheath 12, the latter of which is again positioned over and about the guidewire 22. Also shown is an embolic debris 76 which has been urged along the blood vessel 74 and along the exterior of the capture/delivery sheath 12 and which has entered the open end 46 of the distal filter 26d. The further distally directed positioning of the distal end of the capture/delivery sheath 12 over and about the distal filter 26d and the strands 48 causes the elongation and compression of the distal filter 26d. Such compression causes the parting, division and maceration of the embolic debris 76 engaging the open end 46 and the filter end 47 of the distal filter 26d as the distal filter 26d is retrieved into the capture/delivery sheath 12.

The capture/delivery sheath 12 is progressively, directly, compres singly, and distally positioned over and about the distal filter 26d and engaged with the embolic debris 76 in order to progressively part, divide and macerate the embolic debris 76 and force its passage through the small openings 52a in the form of relatively small pieces which can be carried downstream as urged by bloodflow. Finally, the capture/delivery sheath 12 fully compresses the distal filter 26d to a minimum profile, such as suggested with reference to FIG. 25. Such a low profile structure of such components may be readily withdrawn, preferably in the general manner and fashion as previously described with respect to the preferred embodiment. In the alternative, a guidewire 22 having either a proximal filter 24d or a distal filter 26d can be used to part, divide and macerate the large embolic debris 76 in the manner as described herein.

Figure 37:
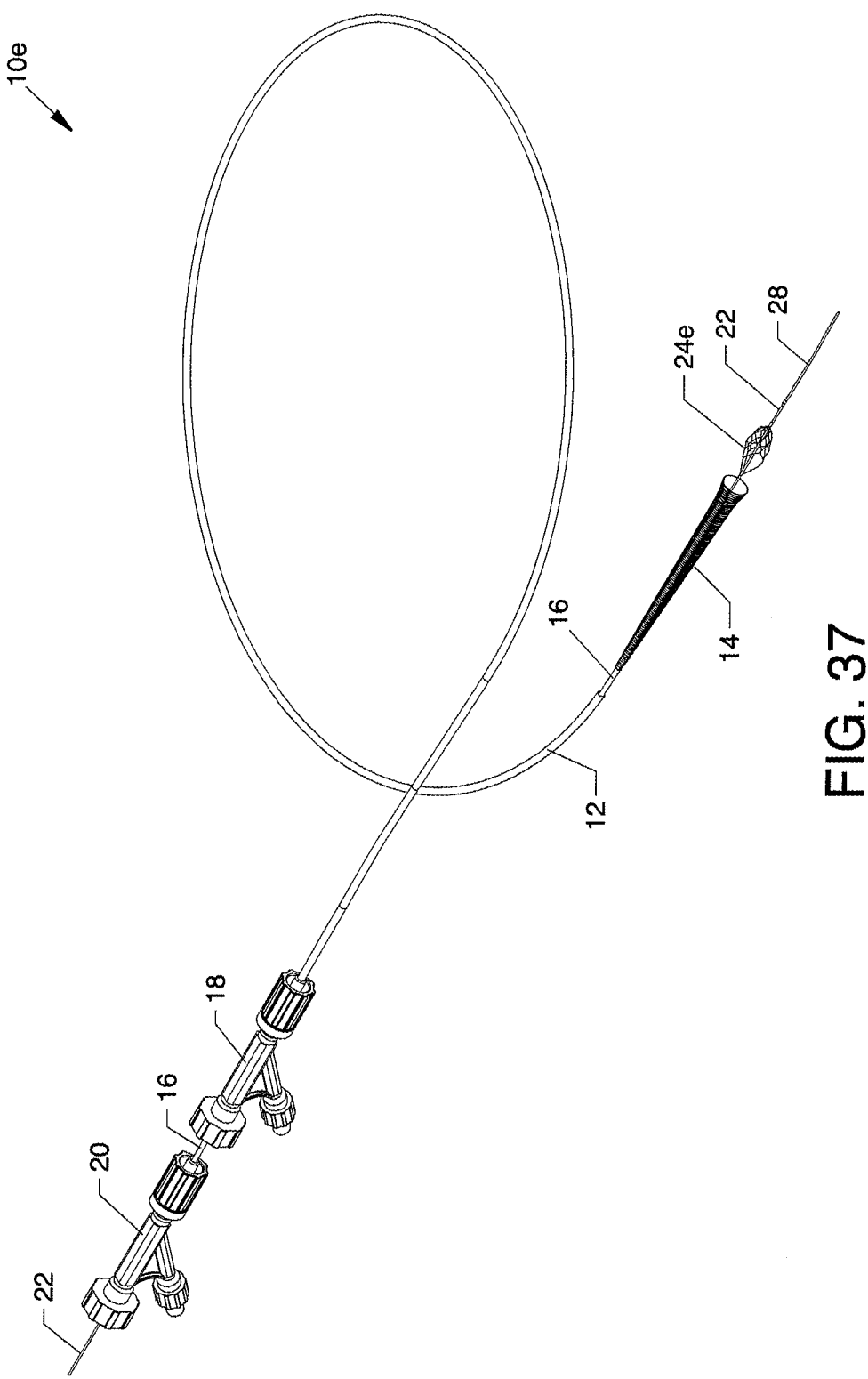
FIG. 37, a fifth alternative embodiment, is an isometric overview of the intravascular emboli capture and retrieval system for intravascular embolism protection and embolism removal or maceration.

FIG. 37, a fifth alternative embodiment, is an isometric overview of the intravascular embolic capture and retrieval system for intravascular embolism protection and embolism removal, 10e. Generally, this alternative embodiment is useful in blood vessels of 8 mm or less to capture embolic debris although maceration of such debris is also associated therewith and is used in a closely related manner as previously described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This fifth alternative embodiment is similar to and closely related to the preferred embodiment of FIG. 1 but instead of the proximal filter 24 and the distal filter 26 only one similarly constructed filter 24e which is not designated as distal or proximal is used. The flexible preformed memory shaped filter 24e of this fifth alternative embodiment which can be deployed distal to large embolic debris 76 is used in lieu of the preformed memory shaped distal filter 26 and the preformed memory shape proximal filter 24 of the preferred embodiment and is located on the guidewire 22 including the same shape and the same characteristics. As can be appreciated by those of skill in the art, one or more preformed memory shaped filters can be utilized in configurations consistent with the scope of the present disclosure.

Figure 38:
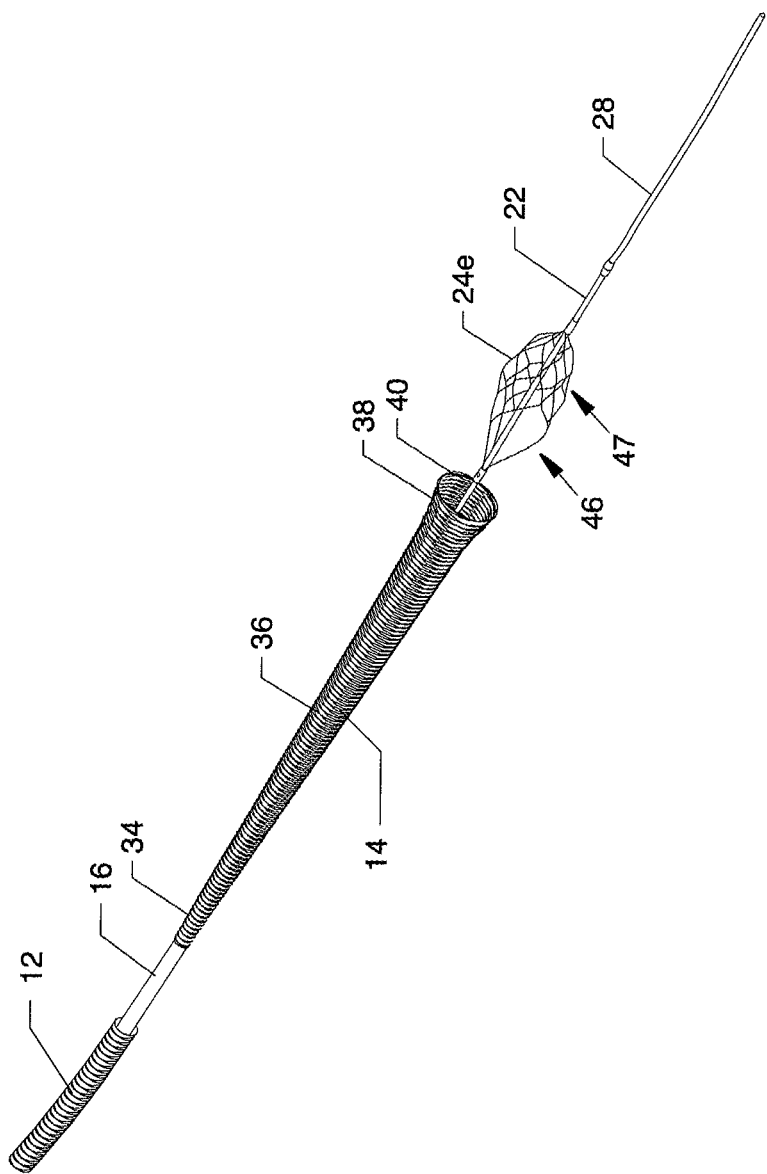
FIG. 38 is an illustration similar to FIG. 2 and is an isometric view of the components located at the distal region of the fifth alternative embodiment.

FIG. 38 is an illustration similar to FIG. 2 and is an isometric view of the components located at the distal region of the fifth alternative embodiment of the present disclosure. Shown, in particular, is the relationship of the filter 24e to the capture sleeve 14.

Mode of Operation

The mode of operation of the fifth alternative embodiment of the intravascular guidewire filter system 10e for the filtering and removal of various sized pieces of organized embolic debris is now described with reference to FIGS. 39-42 as well as understood reference to previously described figures. The capture sleeve operator 20 and the capture/delivery sheath operator 18, used singly or together, are operated to position the capture sleeve 14 and the capture/delivery sheath 12, respectively, in cooperating operation including the movement or nonmovement of the guidewire 22 and the attached filter 24e as required during various delivery and capture phases, such as previously described with reference to the preferred embodiment. Engagement and entrapment of the large embolic debris 76 can be accomplished by the judicious placement of the filter 24e with respect to the large embolic debris 76. With respect to the large embolic debris 76, the guidewire 22 is deployed to position the filter 24e distal to the large piece of embolic debris 76 and used as described herein.

Figure 39:
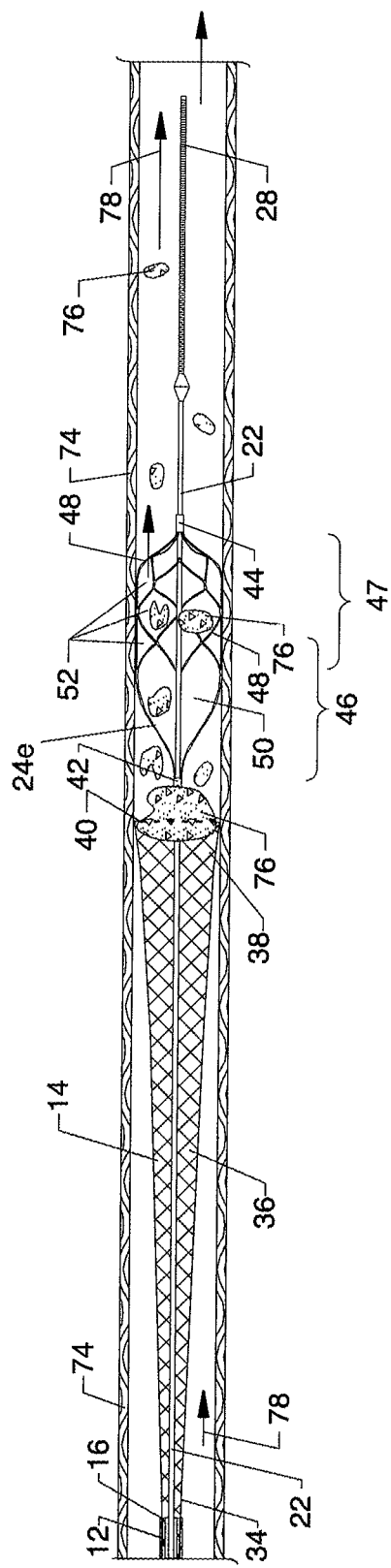
FIG. 39 is a cutaway view is shown in partial cross section and partial cutaway view in the capture mode.

As shown in FIG. 39 and with respect to the fifth alternative embodiment, a cutaway view is shown in partial cross section and partial cutaway view in the capture mode showing the filter 24e (in cutaway view) and the guidewire 22 deployed and aligned within a blood vessel 74 showing a large piece of embolic debris 76 located proximal to the filter 24e just prior to initial engagement of the filter 24e and during initial engagement of the embolic debris 76 by the flared distal section 38 of the capture sleeve 14. The capture sleeve 14 which has been expandingly deployed in the blood vessel 74, as previously described in the preferred embodiment, is shown immediately proximal to the filter 24e. Manual positioning of the guidewire 22 in a proximal direction first causes the open end 46 and then causes the deployed filter end 47 of the filter 24e to engage and urge the large piece of embolic debris 76 proximally into the flared distal section 38 of the capture sleeve 14, the latter of which may be urged distally to cooperatively accommodate the large piece of embolic debris 76.

Figure 40:
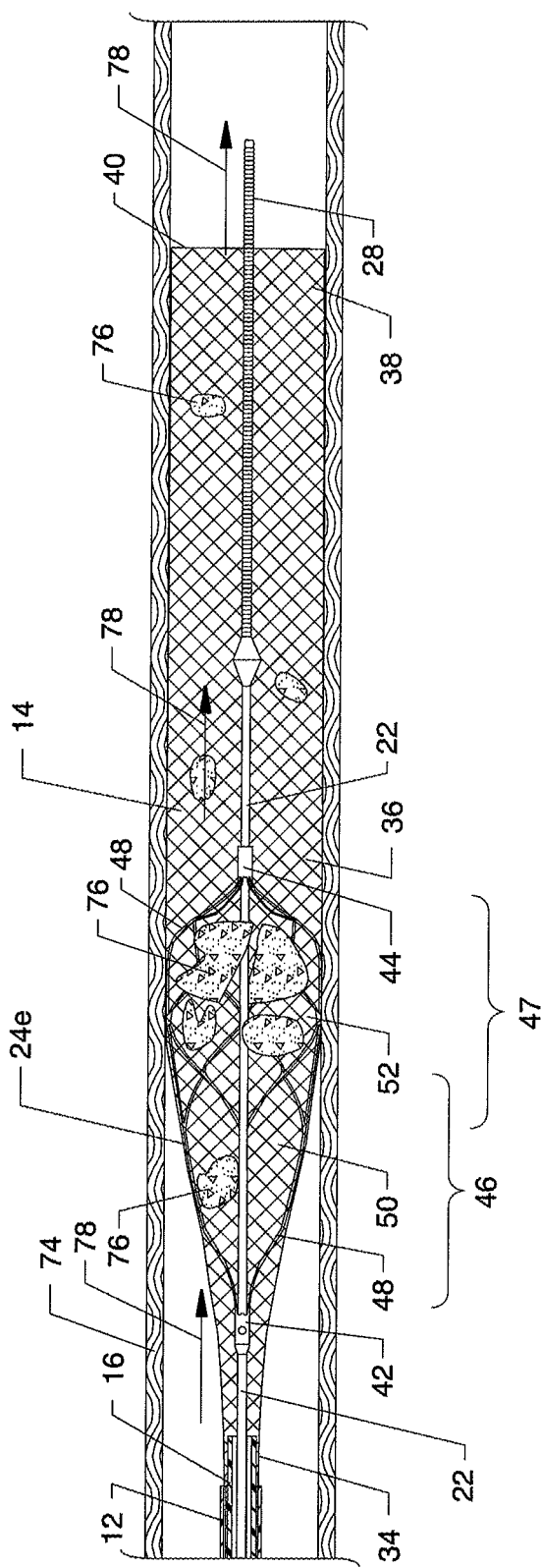
FIG. 40 is an illustration similar to FIG. 6 further showing the use of the capture sleeve in the capture mode by showing the engagement of the capture sleeve over and about the filter which has entrapped embolic debris therein.

Engagement and entrapment of embolic debris 76 can be accomplished either by the distal blood flow containing smaller pieces of embolic debris 76 into the proximal filter 24 and/or the distal filter 26, as previously described, or by the manual forcible urging of the guidewire 22 and the connected filter 24e proximally to forcibly and robustly engage, part, divide and macerate large pieces or collections of embolic debris 76 which can be temporarily urged into and temporarily fixed in place for parting in the capture sleeve 14 by contact caused by the proximal urging of the filter 24e. Some of the large pieces of embolic debris 76 can be engaged, parted, divided and macerated by blood flow induced forced contact with the strands 48 of the filter 24e and can gain entry into the interior of the filter 24e through the large openings 50 of the proximally located open end 46 during parting, dividing and macerating where entrapment is provided by the strands 48 at the small openings 52 in the distally located filter end 47 as shown in FIG. 40. Small particles of embolic debris 76 may pass directly through the large openings 50 for 2 trapping by the strands 48 at the small openings 52 at the distally located filter end 47 of the filter 24e without contacting the strands 48 of the large openings 50. Very small particles of embolic debris 76 which pass through the located filter ends 47 of the filter 24e may be of insignificant consequence and can pass downstream.

FIG. 40 is an illustration similar to FIG. 6 further showing the use of the capture sleeve 14 in the capture mode by showing the engagement of the capture sleeve 14 over and about the filter 24e which has entrapped embolic debris 76 therein. Such engagement is accomplished by advancing the capture sleeve 14 distally toward and over the filter 24e by operation of the capture sleeve operator 20. The guidewire 22 can be cooperatively actuated proximally in order to cause intimate contacting and pulling and urging the large piece of embolic debris 76 into the capture sleeve 14 by impingement of the embolic debris 76 by the features of the proximally directed filter 24e, and thence through the flared distal section 38 and the annular edge 40 of the captive sleeve 14 and into the flared midsection 36, i.e., the confines of the capture sleeve 14.

Figure 41:
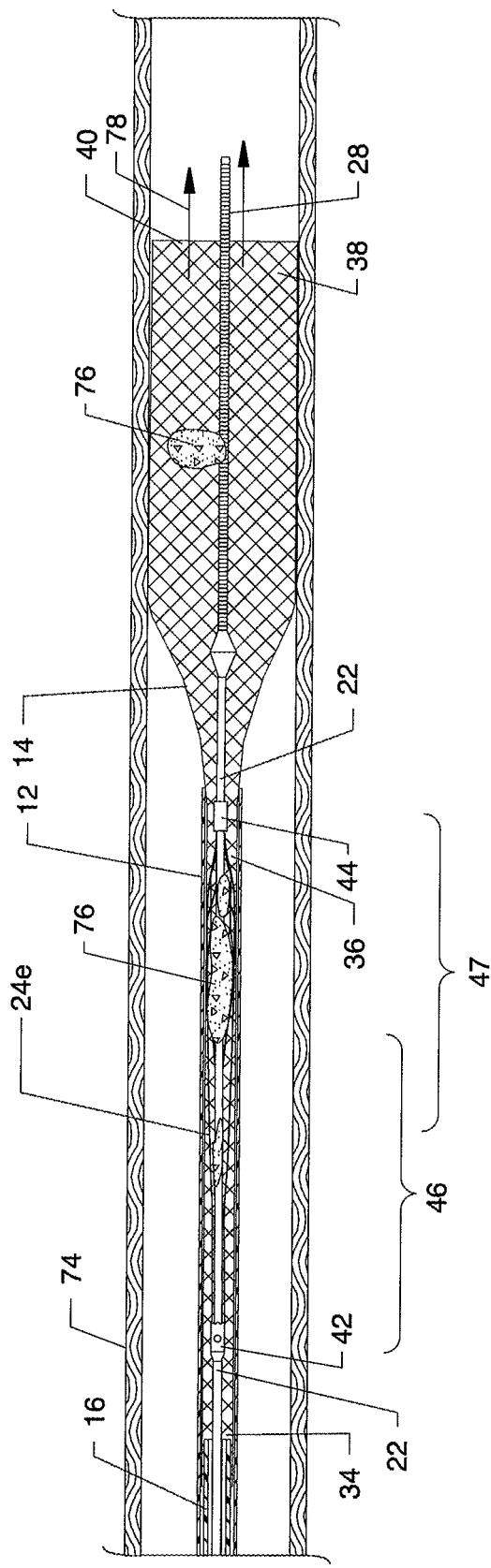
FIG. 41 is an illustration similar to FIG. 7 further showing the use of the capture sleeve and the capture/delivery sheath in the capture mode.

FIG. 41 is an illustration similar to FIG. 7 further showing the use of the capture sleeve 14 and the capture/delivery sheath 12 in the capture mode. Operation of the capture/delivery sheath operator 18 distally forces the capture/delivery sheath 12 distally, whereby the distal end of the capture/delivery sheath 12 is progressively positioned directly over and about the capture sleeve 14 and, simultaneously, is progressively and indirectly positioned over and about the filter 24e which is coaxially aligned within the capture sleeve 14. Such distal progressive distal positioning of the capture/delivery sheath 12 forcibly compresses the capture sleeve 14, the underlying filter 24e and the embolic debris 76 which has been captured within the filter 24e. During compression, the embolic debris 76 can also be elongated or may beneficially be further parted, divided and macerated into smaller pieces.

Figure 42:
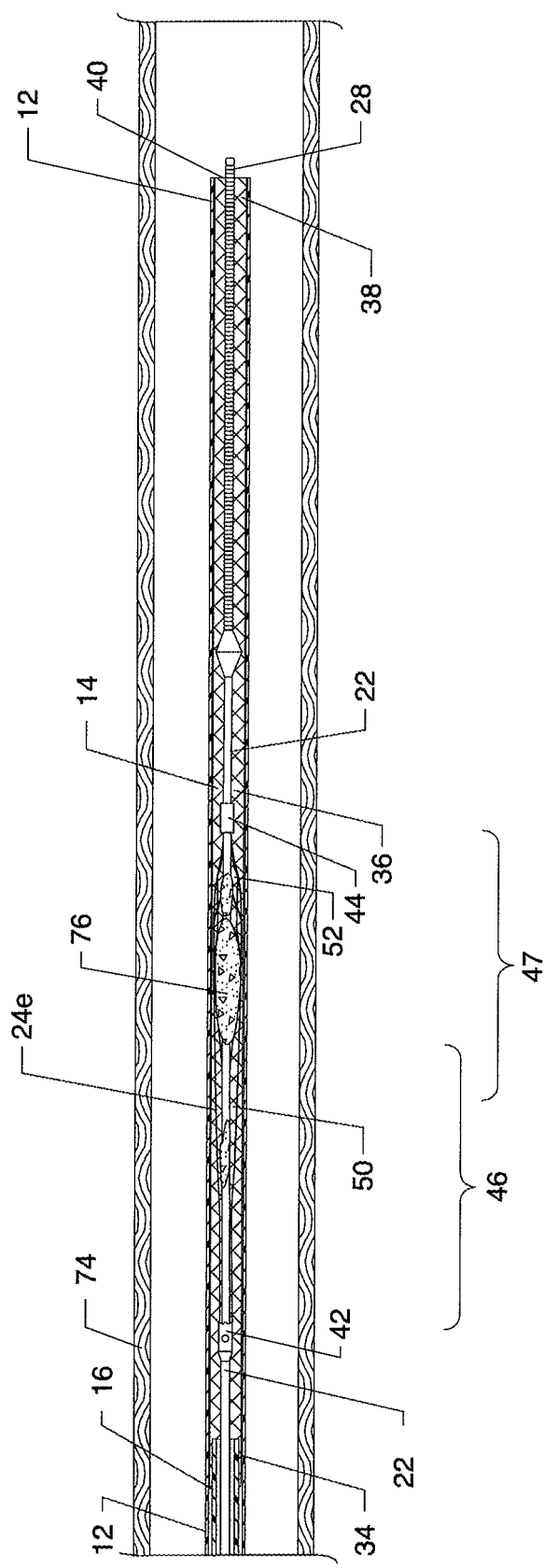
FIG. 42 is an illustration similar to FIG. 8 further showing the use of the capture sleeve and the capture/delivery sheath in the capture mode.

FIG. 42 is an illustration similar to FIG. 8 further showing the use of the capture sleeve 14 and the capture/delivery sheath 12 in the capture mode. In this illustration, the capture/delivery sheath 12 is positioned further and fully in a distal direction to force complete compression of the capture sleeve 14 where the capture/delivery sheath 12 is also in alignment directly over and about the distal portion of the capture sleeve 14 and simultaneously is indirectly and compressingly positioned over and about the filter 24e which is in coaxial alignment within the capture sleeve 14. Complete compression of the capture sleeve 14 indirectly over and about the filter 24e and the embolic debris 76 captured therein provides a low profile structure of such components containing captured embolic debris 76. Components of such low profile structure containing captured embolic debris 76 may be readily withdrawn, preferably in simultaneous fashion, proximally through the capture/delivery sheath 12 where the capture sleeve positioning tube 16, the embolic debris laden capture sleeve 14, the guidewire 22 and the compressed embolic debris laden filter 24e can be withdrawn in a proximally directed removal from the capture/delivery sheath 12 by a proximal and manual directed unitary movement of the capture/delivery sheath operator 18, the capture sleeve operator 20 and attached capture sleeve positioning tube 16, and the guidewire 22. In the alternative, the capture sleeve positioning tube 16, the embolic debris laden capture sleeve 14, the guidewire 22 and filter 24e and the capture/delivery sheath 12 may be entirely and unitarily withdrawn from the blood vessel 74 by the proximal and manually directed movement of the capture/delivery sheath operator 18, the capture sleeve operator 20 and the guidewire 22.

Figure 43:
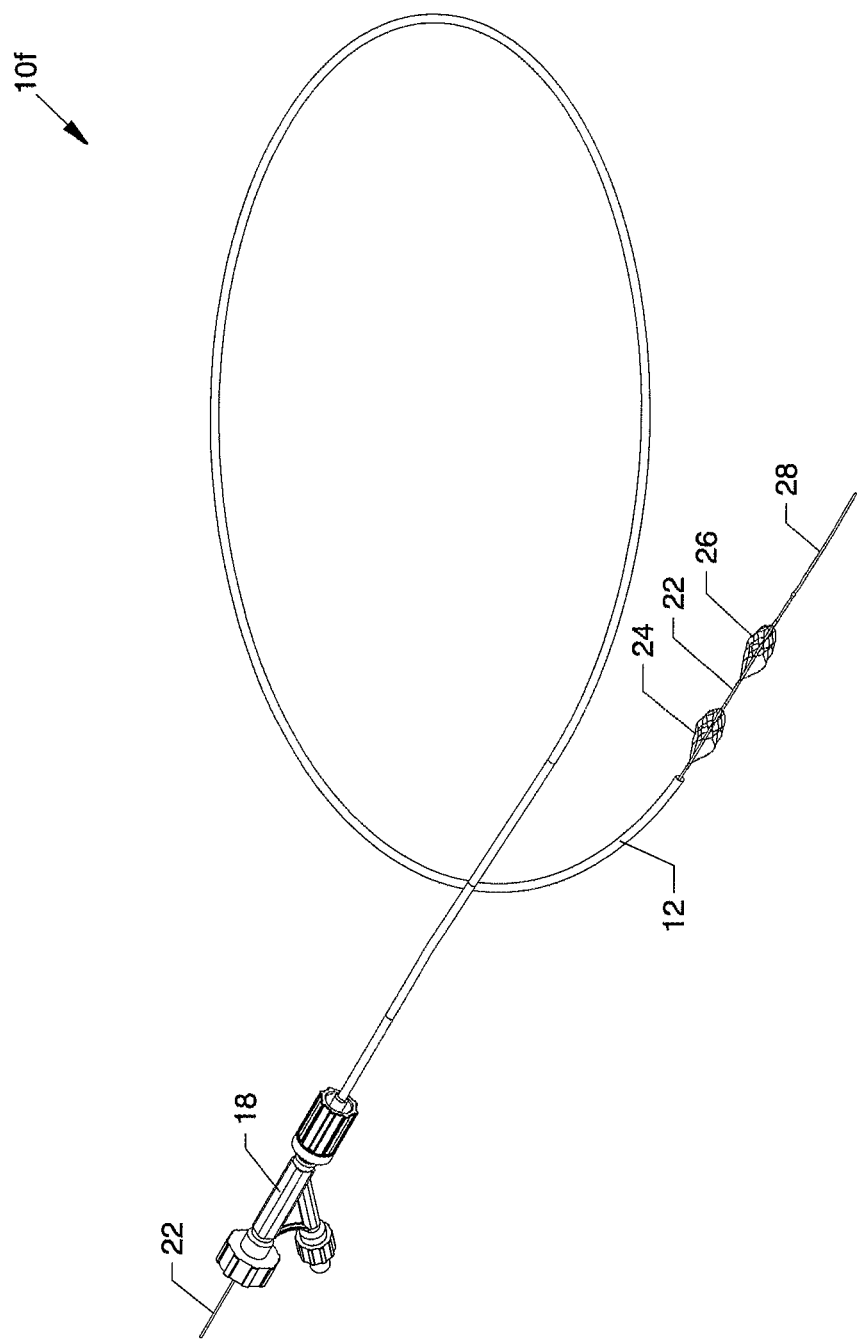
FIG. 43, a sixth alternative embodiment, is an isometric overview of the intravascular emboli capture and retrieval system for intravascular embolism protection and embolism removal or maceration.

FIG. 43, a sixth alternative embodiment, is an isometric overview of the intravascular emboli capture and retrieval system for intravascular embolism protection and embolism removal or maceration, 10f. Generally, this alternative embodiment is useful in blood vessels of 8 mm or less to capture embolic debris although maceration of such debris is also associated therewith and is used in a closely related manner as previously described for the preferred embodiment. For vessels of larger than 8 mm in size, appropriate modifications to the sizing of the components of this embodiment, as known to those of skill in the art, are able to be freely substituted in order to capture or macerate emboli as dictated by each individual patient and scenario. This sixth alternative embodiment is similar to and closely related to the preferred embodiment of FIG. 1 and the use thereof but does not use the capture sleeve 14. As can be appreciated by those of skill in the art, two or more preformed memory shaped filters can be utilized in configurations consistent with the scope of the present disclosure.

Figure 44:
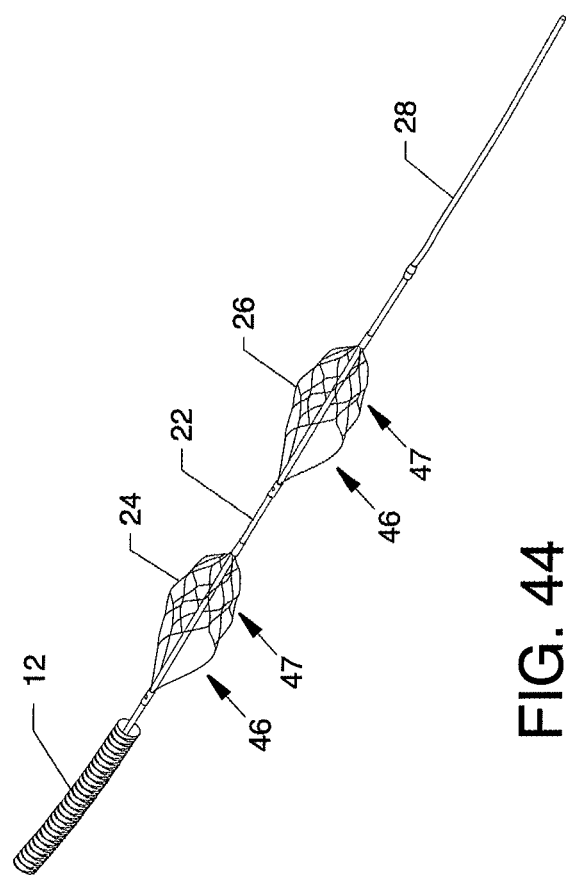
FIG. 44 is an illustration similar to FIG. 2 and is an an isometric view of the components located at the distal region of the sixth alternative embodiment of the present invention.

FIG. 44 is an illustration similar to FIG. 2 and is an isometric view of the components located at the distal region of the sixth alternative embodiment of the present disclosure. Shown, in particular, is the relationship of the proximal filter 24 and the distal filter 26 to the capture delivery sheath 12.

Mode of Operation

The mode of operation of the sixth alternative embodiment of the intravascular guidewire filter system 10f for the filtering and removal of various sized pieces of organized embolic debris is now described with reference to FIGS. 45-48, as well as understood reference to previously described figures. The capture/delivery sheath operator 18 is operated to position the capture/delivery sheath 12 preferably in cooperative operation including the movement or nonmovement of the guidewire 22 and the attached proximal filter 24 and distal filter 26 as required during various delivery and capture phases, such as previously described with reference to the preferred embodiment. Engagement and entrapment of the large embolic debris 76 can be accomplished by the judicious placement of the proximal filter 24 with respect to the large embolic debris 76. With respect to the large embolic debris 76, the guidewire 22 is deployed to position the proximal filter 24 distal to the large piece of embolic debris 76 and used as described herein.

Figure 45:
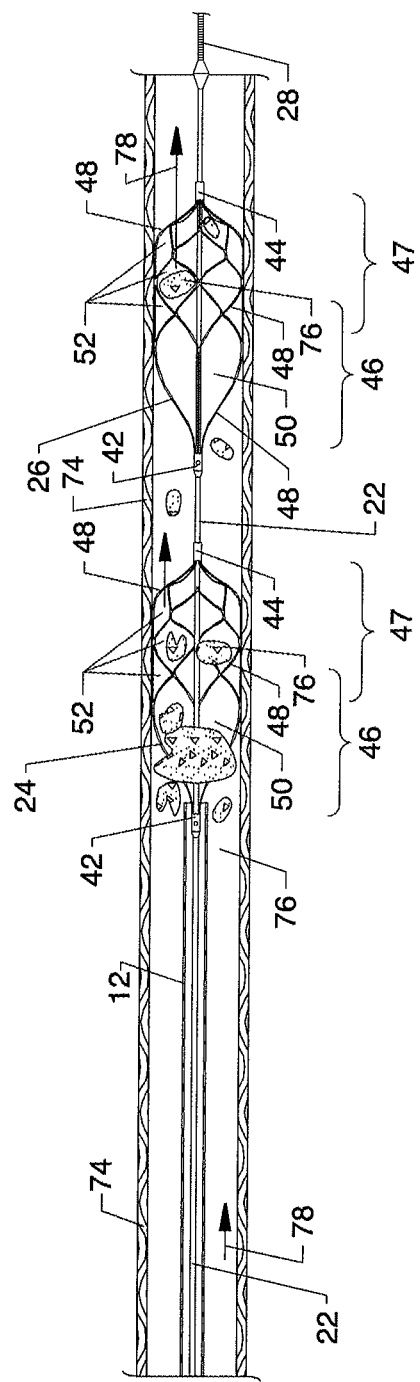
FIG. 45 is a cutaway view of the sixth alternative embodiment shown in partial cross section and partial cutaway view.

As shown in FIG. 45 and with respect to the sixth alternative embodiment, a cutaway view is shown in partial cross section and partial cutaway view in the capture mode showing the proximal filter 24 (in cutaway view), the distal filter 26 and the guidewire 22 deployed and aligned within a blood vessel 74 showing a large piece of embolic debris 76 in initial engagement with the proximal filter 24.

Figure 46:
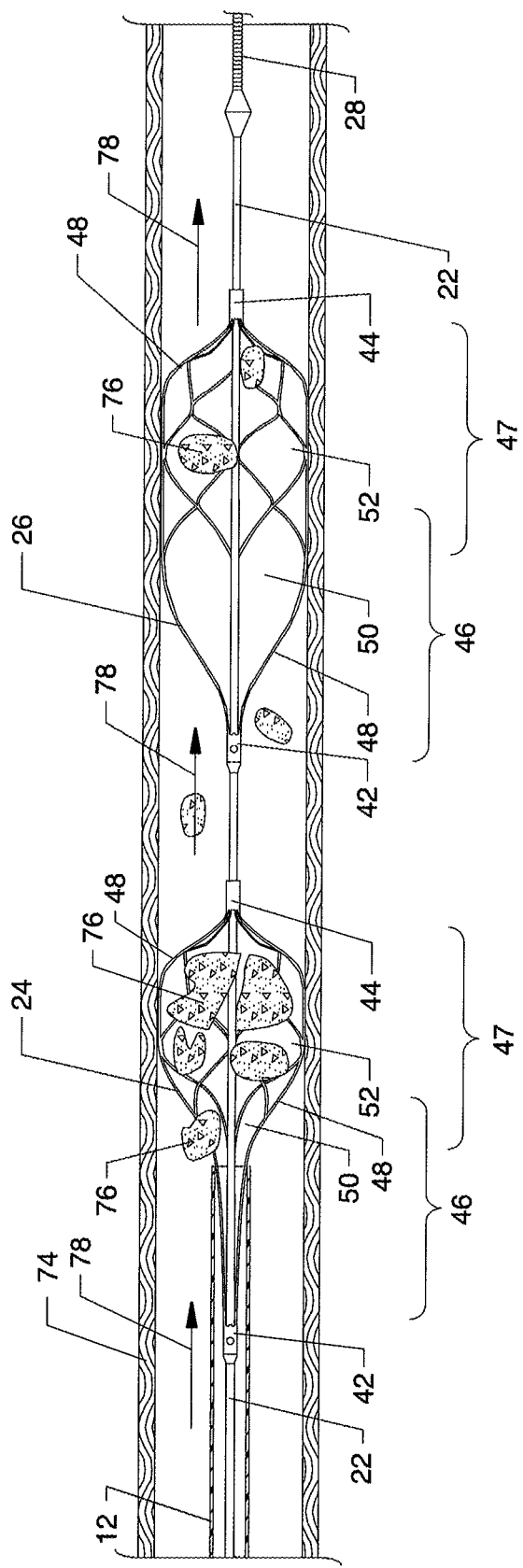
FIG. 46 is an illustration similar to FIG. 6 further showing the initial engagement of the capture/delivery sheath over and about the open end of the proximal filter, shown partially collapsed which has embolic debris entrapped therein.
Figure 47:
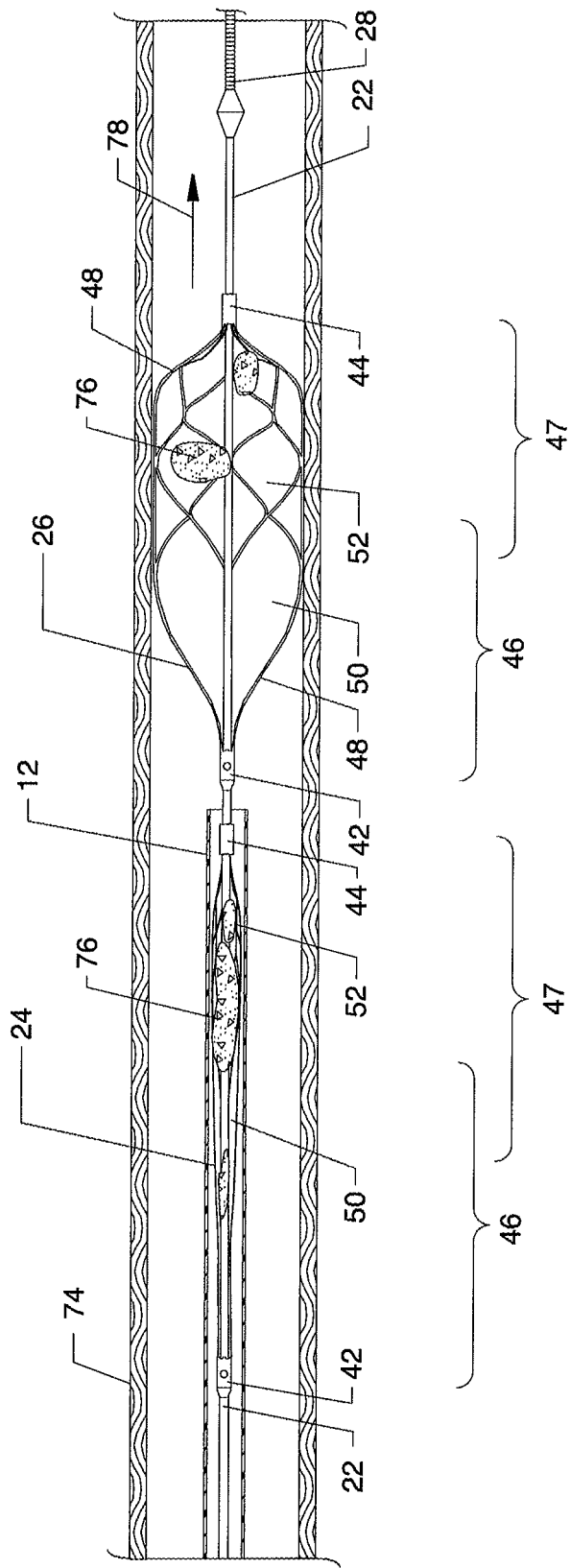
FIG. 47 is an illustration similar to FIG. 7 further showing the use of the capture/delivery sheath in the capture mode.

Engagement and entrapment of the embolic debris 76 can be accomplished either by the distal blood flow containing smaller pieces of embolic debris 76 into the proximal filter 24 and/or the distal filter 26 as previously described, or by the manual forcible urging of the guidewire 22 and the connected proximal filter 24 and the distal filter 26 proximally to forcibly and robustly engage, part, divide and macerate large pieces or collections of embolic debris 76 as described in FIG. 46. Some of the large pieces of embolic debris 76 which can be engaged, parted, divided and macerated by blood flow induced and forced contact with the strands 48 of the proximal filter 24 and can gain entry into the interior of the proximal filter 24 through the large openings 50 of the proximally located open end 46 during such engagement, parting, dividing and macerating where entrapment is provided by the strands 48 at the small openings 52 in the distally located filter end 47 as shown in FIG. 47. Small particles of embolic debris 76 may pass directly through the large openings 50 for trapping by the strands 48 at the small openings 52 at the distally located filter end 47 of the proximal filter 24 without contacting the strands 48 of the large openings 50. Very small particles of embolic debris 76 which pass through the located filter ends 47 of the proximal filter 24 (and the distal filter 26) may be of insignificant consequence and can pass downstream.

FIG. 46 is an illustration similar to FIG. 6 further showing the initial engagement of the capture/delivery sheath 12 over and about the open end 46 of the proximal filter 24, shown partially collapsed which has embolic debris 76 entrapped therein. Such engagement is accomplished by advancing the capture/delivery sheath 12 distally toward and over the proximal filter 24 and then the distal filter 26 by operation of the capture/delivery sheath operator 18 in order to forcibly collapse the proximal filter 24 and then the distal filter 26 over and about any embolic debris which may be located within the open end 46 or the filter end 47 of the proximal filter 24 and then the open end 46 or the filter end 47 of the distal filter 26. The guidewire 22 can be cooperatively actuated proximally in order to assist in intimate contacting and collapsing of the proximal filter 24 and the distal filter 26 in order to accomplish destruction or reforming of the embolic debris 76 where the strands 48 forcibly and robustly engage, part, divide and macerate embolic debris 76 by impingement of the embolic debris 76 by the features of the proximal filter 24 and the distal filter 26.

FIG. 47 is an illustration similar to FIG. 7 further showing the use of the capture/delivery sheath 12 in the capture mode. Operation of the capture/delivery sheath operator 18 forces the capture/delivery sheath 12 distally whereby the distal end of the capture/delivery sheath 12 is progressively positioned directly over and about the proximal filter 24. Such distal progressive distal positioning of the capture/delivery sheath 12 forcibly compresses the underlying proximal filter 24 and the embolic debris 76 which has been captured within the proximal filter 24. During compression, the embolic debris 76 can also be elongated or may beneficially be further parted, divided and macerated into smaller pieces.

Figure 48:
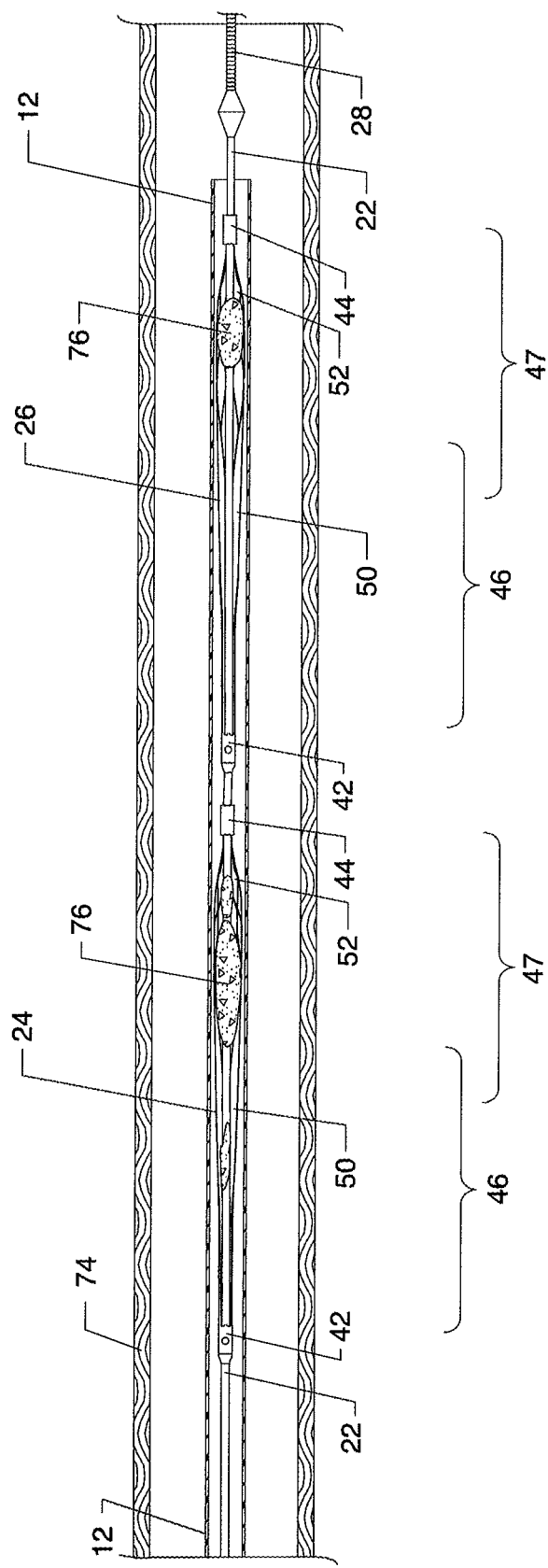
FIG. 48 is an illustration similar to FIG. 8 further showing the use of the capture/delivery sheath in the capture mode.

FIG. 48 is an illustration similar to FIG. 8 further showing the use of the capture/delivery sheath 12 in the capture mode. In this illustration, the capture/delivery sheath 12 is positioned further and fully in a distal direction where the capture/delivery sheath 12 is also in alignment directly over and about and compressingly positioned over and about the distal filter 26. Complete compression of the proximal filter 24 and the embolic debris 76 captured therein and the distal filter 26 and the embolic debris 76 captured therein provides a low profile structure of such components containing captured embolic debris 76. Components of such low profile structure containing captured embolic debris 76 may be readily withdrawn proximally through the capture/delivery sheath 12 where the guidewire 22 and the compressed embolic debris laden proximal filter 24 and distal filter 26 can be withdrawn in a proximally directed removal from the capture/delivery sheath 12 by a proximal and manual directed movement of the guidewire 22 and the attached and compressed proximal filter 24 and distal filter 26. In the alternative, the guidewire 22, the proximal filter 24, the distal filter 26 and the capture/delivery sheath 12 may be entirely and unitarily withdrawn from the blood vessel 74 by the proximal and manually directed unitary movement of the capture/delivery sheath operator 18 and the guidewire 22.

Various modifications can be made to the devices set forth in the present disclosure without departing from the apparent scope thereof.

It is claimed:

1. An intravascular guidewire filter system comprising:
a manifold having a central elongated tubular body, said central elongated tubular body having a proximal end and a distal end;
an elongated flexible delivery tube having a proximal end and a distal end, said proximal end of said elongated flexible delivery tube being fixed within said distal end of said central elongated tubular body;
an apertured seal within said proximal end of said central elongated tubular body;
a guidewire having a proximal end and a distal end, said guidewire extending through said apertured seal, through said elongated tubular body, and through said elongated flexible delivery tube;
a flexible preformed memory shaped distal filter configured to capture debris between deployed distal filter strands spaced from the guidewire;
a flexible preformed memory shaped proximal filter configured to capture debris between deployed proximal filter strands spaced from the guidewire;
wherein each of said proximal and distal filters has a proximal tube surrounding and attached to said guidewire and to said proximal end of each of said filters and a distal tube attached to said distal end of each of said filters and surrounding and slideable along said guidewire; and
a capture sleeve slidably coupled along the guidewire and coupled with the distal end of the elongated flexible delivery tube, the capture sleeve includes a capture configuration and a compressing configuration:
in the capture configuration the capture sleeve tapers from an annular open edge toward the proximal end of the guide wire, the capture sleeve is configured to receive the proximal and distal filters having the respective deployed distal and proximal filter strands; and in the compressing configuration the capture sleeve is compressed relative to the capture configuration, and the compressed capture sleeve collapses the respective distal and proximal filter strands of the distal and proximal filters and the captured debris to the guidewire.

2. The intravascular guidewire filter system of claim 1, wherein said proximal filter has a concave basket shaped configuration having a concave shaped side, said proximal filter has said concave shaped side facing in a proximal direction and said distal filter has an angulated circumferential configuration.

3. The intravascular guidewire filter system of claim 1, wherein said flexible preformed memory shaped proximal filter has a concave basket shaped configuration having a concave shaped side, said proximal filter has said concave shaped side facing in a proximal direction and said flexible preformed memory shaped distal filter has an angulated circumferential configuration.

4. The intravascular guidewire filter system of claim 1, wherein each of said flexible preformed memory shaped proximal and distal filters is made from multiple strands of nitinol.

5. The intravascular guidewire filter system of claim 1, wherein the capture sleeve includes a woven mesh.

6. The intravascular guidewire filter system of claim 1, wherein the taper of the capture sleeve includes a flared distal section proximate the annular open edge, and the flared distal section includes a relatively greater taper than the remainder of the capture sleeve.

7. The intravascular guidewire filter system of claim 1 comprising a capture sheath slidably coupled along the capture sleeve, and the capture sheath is configured to surround the capture sleeve and transition the capture sleeve from the capture configuration to the compressing configuration.

8. The intravascular guidewire filter system of claim 1, wherein in the compressing configuration the respective distal and proximal filter strands are positioned along the guidewire.

9. The intravascular guidewire filter system of claim 1, wherein in the compressing configuration the respective distal and proximal filter strands are aligned with the guidewire.

10. The intravascular guidewire filter system of claim 1, wherein in the compressing configuration the proximal filter is entirely received within the capture sleeve as the compressed capture sleeve collapses the proximal filter, and
the distal filter is entirely received within the capture sleeve as the compressed capture sleeve collapses the distal filter.

11. An intravascular guidewire filter system comprising:
a manifold having a central elongated tubular body, said central elongated tubular body having a proximal end and a distal end;
an elongated flexible delivery tube having a proximal end and distal end, said proximal end of said elongated flexible delivery tube being fixed within said distal end of said central elongated tubular body;
an apertured seal within said proximal end of said central elongated tubular body;
a guidewire having a proximal end and a distal end, said guidewire extending through said apertured seal, through said elongated tubular body, and through said elongated flexible delivery tube;

two or more flexible preformed memory shaped filters configured to capture debris between deployed filter strands of the respective filters spaced from the guidewire;

wherein each of said two or more preformed memory shaped filters has a proximal tube surrounding and attached to said guidewire and to said proximal end of each of said filters and distal tube attached to said distal end of each of said filters and surrounding and slideable along said guidewire; and a capture sleeve slidably coupled along guide wire and coupled with the distal end of the elongated flexible delivery tube, the capture sleeve includes a capture configuration and a compressing configuration:

in the capture configuration the capture sleeve is configured to receive the preformed memory shaped filters having the respective deployed filter strands with debris therein; and in the compressing configuration the capture sleeve is compressed relative to the capture configuration and collapses the respective filter strands to the guidewire, and one or more of the compressed capture sleeve or the collapsed filter strands compresses the captured debris to the guidewire.

12. The intravascular guidewire filter system of claim 11, wherein the capture sleeve includes a woven mesh.

13. The intravascular guidewire filter system of claim 11, wherein the capture sleeve includes a flared distal section proximate the annular open edge, and the flared distal section includes a relatively greater taper than the remainder of the capture sleeve.

14. The intravascular guidewire filter system of claim 11 comprising a capture sheath slidably coupled along the capture sleeve, and the capture sheath is configured to surround the capture sleeve and transition the capture sleeve from the capture configuration to the compressing configuration.

15. The intravascular guidewire filter system of claim 11, wherein in the compressing configuration the respective filter strands are collapsed to a position along the guidewire.

16. The intravascular guidewire filter system of claim 11, wherein in the compressing configuration the respective filter strands are collapsed into alignment with the guidewire.

17. The intravascular guidewire filter system of claim 11, wherein the two or more flexible preformed memory shaped filters include at least first and second filters, and in the compressing configuration the first filter is entirely received within the capture sleeve as the compressed capture sleeve collapses the proximal filter, and the second filter is entirely received within the capture sleeve as the compressed capture sleeve collapses the second filter.

18. The intravascular guidewire filter system of claim 11, wherein the capture sleeve is tapered from an annular open edge toward the proximal end of the guidewire.

* * * * *